United States Patent
Aso et al.

(10) Patent No.: US 8,378,338 B2
(45) Date of Patent: Feb. 19, 2013

(54) CONJUGATED COMPOUND, NITROGENATED CONDENSED-RING COMPOUND, NITROGENATED CONDENSED-RING POLYMER, ORGANIC THIN FILM, AND ORGANIC THIN FILM ELEMENT

(75) Inventors: Yoshio Aso, Suita (JP); Yutaka Ie, Suita (JP); Makoto Okabe, Suita (JP); Masashi Nitani, Suita (JP); Masato Ueda, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 167 days.

(21) Appl. No.: 12/745,481

(22) PCT Filed: Nov. 27, 2008

(86) PCT No.: PCT/JP2008/071520
§ 371 (c)(1),
(2), (4) Date: May 28, 2010

(87) PCT Pub. No.: WO2009/069687
PCT Pub. Date: Jun. 4, 2009

(65) Prior Publication Data
US 2010/0301314 A1 Dec. 2, 2010

(30) Foreign Application Priority Data

Nov. 30, 2007 (JP) .................. P2007-311381
Feb. 13, 2008 (JP) .................. P2008-031972
Aug. 28, 2008 (JP) .................. P2008-220031

(51) Int. Cl.
*H01L 29/08* (2006.01)
(52) U.S. Cl. ............... 257/40; 313/504; 438/99
(58) Field of Classification Search ........... 257/40; 313/504; 438/99
See application file for complete search history.

(56) References Cited

U.S. PATENT DOCUMENTS 5,093,432 A    3/1992 Bierschenk et al.
6,249,369 B1 * 6/2001 Theiste et al. ............... 359/265
(Continued)

FOREIGN PATENT DOCUMENTS

CN  101001901 A   7/2007
DE  112006002392 T5  10/2008
(Continued)

OTHER PUBLICATIONS

Gan Wenjun, et al., "Effect of Molecular Weight on Reaction-Induced Phase Separation of Epoxy Resin Modified with Fluorocarbon Chain Terminated Polyetherimide", Science in China Series B: Chemistry, 2005, pp. 560-566, vol. 48, No. 6.

(Continued)

*Primary Examiner* — Jarrett Stark
*Assistant Examiner* — Caleb Henry
(74) *Attorney, Agent, or Firm* — Sughrue Mion, PLLC

(57) ABSTRACT

According to the first invention group there are provided conjugated compounds having two or more groups represented by the following formula (I) or the following formula (II):

[Chemical Formula 1]

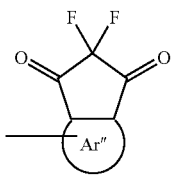 (II)

wherein one of Ar and Ar' represents a C6 or greater divalent aromatic hydrocarbon group and the other represents a C4 or greater divalent heterocyclic group, wherein the groups each may have a substituent, with the proviso that the groups as a whole contain no fluorine atoms, $R^1$ and $R^2$ each independently represent a hydrogen atom, a halogen atom or a monovalent group, and Ar" represents a trivalent aromatic hydrocarbon or trivalent heterocyclic group; when the conjugated compound has two or more groups represented by formula (I), the portion excluding these groups contain no fluorine atoms.

According to the second group of the present invention there are provided nitrogen-containing fused-ring compounds represented by the following formula (α-I):

[Chemical Formula 2]

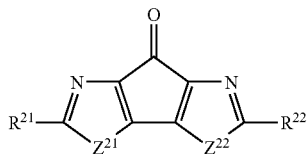 (α-I)

in formula (α-I), $R^{21}$ and $R^{22}$ each independently represent a hydrogen atom, a halogen atom or an optionally substituted monovalent group, and $Z^{21}$ and $Z^{22}$ each independently represent any one of the groups represented by the following formulas (α-i)-(α-ix);

[Chemical Formula 3]

 (α-i)

 (α-ii)

 (α-iii)

 (α-iv)

 (α-v)

 (α-vi)

 (α-vii)

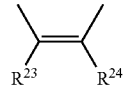 (α-viii)

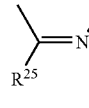 (α-ix)

wherein $R^{23}$, $R^{24}$, $R^{25}$ and $R^{26}$ each independently represent a hydrogen atom, a halogen atom or a monovalent group, and $R^{23}$ and $R^{24}$ may bond together to form a ring, the left side and the right side of the group represented by formula (α-viii) may be interchanged.

19 Claims, 14 Drawing Sheets

U.S. PATENT DOCUMENTS

| | | | |
|---|---|---|---|
| 7,524,567 B2* | 4/2009 | Park et al. | 428/690 |
| 2004/0072989 A1* | 4/2004 | Son et al. | 528/397 |
| 2004/0183068 A1 | 9/2004 | Ong et al. | |
| 2004/0186266 A1 | 9/2004 | Jiang et al. | |
| 2004/0230021 A1 | 11/2004 | Giles et al. | |
| 2005/0239994 A1 | 10/2005 | Litt et al. | |
| 2005/0276981 A1 | 12/2005 | Ong et al. | |
| 2006/0094859 A1 | 5/2006 | Marrcco, III et al. | |
| 2006/0110623 A1 | 5/2006 | Funahashi et al. | |
| 2006/0166038 A1* | 7/2006 | Park et al. | 428/690 |
| 2006/0186401 A1* | 8/2006 | Marks et al. | 257/40 |
| 2006/0237695 A1 | 10/2006 | Williams et al. | |
| 2007/0176541 A1* | 8/2007 | Son et al. | 313/504 |
| 2007/0237982 A1 | 10/2007 | Inoue et al. | |
| 2007/0252139 A1 | 11/2007 | McKiernan et al. | |
| 2008/0048181 A1 | 2/2008 | Tanaka et al. | |
| 2009/0256475 A1* | 10/2009 | Nakatani et al. | 313/504 |

FOREIGN PATENT DOCUMENTS

| | | |
|---|---|---|
| EP | 1 279 689 A2 | 1/2003 |
| EP | 1 477 504 A1 | 11/2004 |
| EP | 1 627 891 A1 | 2/2006 |
| EP | 1 776 404 B1 | 1/2008 |
| EP | 2123690 A1 | 11/2009 |
| JP | 5-110069 A | 4/1993 |
| JP | 6-135869 A | 5/1994 |
| JP | 2001-247498 A | 9/2001 |
| JP | 2004-006476 A | 1/2004 |
| JP | 2004-107257 A | 4/2004 |
| JP | 2004-339516 A | 12/2004 |
| JP | 2005-235923 | 9/2005 |
| JP | 2006-013483 A | 1/2006 |
| JP | 2007-116115 A | 5/2007 |
| JP | 2007-197359 A | 8/2007 |
| JP | 2008-509266 T | 3/2008 |
| KR | 10-2007-0051265 A | 5/2007 |
| WO | 90/05308 A1 | 5/1990 |
| WO | 03/010778 A | 2/2003 |
| WO | 2005/122278 A1 | 12/2005 |
| WO | 2006/015862 A1 | 2/2006 |
| WO | 2006/098121 A1 | 9/2006 |
| WO | 2007/029547 A1 | 3/2007 |
| WO | 2007/050049 A1 | 5/2007 |
| WO | 2007/068326 A1 | 6/2007 |
| WO | 2008/108405 A1 | 9/2008 |
| WO | 2008/111461 A1 | 9/2008 |

OTHER PUBLICATIONS

Hajime Irikawa, et al., "Formation and Structures of Dimeric Compounds from an (E)-5,5'-Diphenyl-2,2',3,3'-Tetrahydro-3,3'-Bipyrrolylidene-2,2'-Dione", Bulletin of the Chemical Society of Japan, 2001, pp. 555-559, vol. 74, No. 3.

Yoshiaki Nakano, et al., "Synthesis and Intramolecular Magnetic Interaction of Triphenylamine Derivatives with Nitronyl Nitroxide Radicals", Polyhedron, 2005, pp. 2141-2147, vol. 24 (16-17).

Josemon Jacob, et al., "Ladder-Type Pentaphenylenes and Their Polymers: Efficient Blue-Light Emitters and Electron-Accepting Meterials via a Common Intermediate," J. Am. Chem. Soc., 2004, vol. No. 126, pp. 6987-6995.

Paolo Coppo, et al., "New routes to poly(4,4-dialkylcyclopentadithiophene-2,6-diyls)," J. Mater. Chem., 2002, vol. 12, pp. 2597-2599.

Yutaka IE, et al, "Synthesis, Properties, and Structures of Difluoromethylene-bridged Coplanar p-Terphenyl and Its Aryl-capped Derivatives for Electron-transporting Materials," Chemistry Letters, vol. 36, No. 11, 2007, pp. 1326-1327.

Yutaka IE, et al., "Electronegative Oligothiophenes Based on Difluorodioxocyclopentene-Annelated Thiophenes: Synthesis, Properties, and n-Type FET Performances", Organic Letters, 2008, vol. 10, No. 5, pp. 833-836.

Yutaka IE, et al., "Perfluoroalkyl-annelated conjugated systems toward n-tpe organic semiconductors", Pure Appl. Chem., 2008, vol. 80, No. 3, pp. 589-597.

Paul A. Keller, et al., "Oxidative coupling of indoles using thallium(III) trifluoroacetate", Tetrahedrom, 2008, vol. 64, pp. 7787-7795.

V.G. Nenajdenko, et al., "Synthesis of aminoalkylpyrazoles and -isoxazoles from cyclic beta-(trifluoroacetyl) enamines", Russian Chemical Bulletin, International Edition, Feb. 2007, vol. 56, No. 2, pp. 336-344.

Office Action issued Feb. 15, 2012 in U.S. Appl. No. 12/530,435 to Yutaka Ie.

Extended European Search Report issued Feb. 13, 2012, in European Patent Application No. 08853653.7.

Extended European Search Report issued Aug. 2, 2012 in European Patent Application No. 08721388.0.

Office Action issued Sep. 10, 2012 in European Patent Application No. 08 853 653.7 to Sumitomo Chemical Co., Ltd.

Extended European Search Report issued Oct. 5, 2012 in European Patent Application No. 12176179.5 to Sumitomo Chemical Co., Ltd.

Mlochowski J et al, "Electrophilic Substitution in the Azafluorenone Systems—Bromination of Azafluorenoneshelektrophile Substitution in Azafluorenonsystemen—Bromierung Von Azafluorenonen", Journal Fuer Praktische Chemie, Leipzig, DE, vol. 322, No. 6, Jan. 1, 1980, pp. 971-980, XP009033764.

Szulc Z et al, "Synthesis of Potential Interferon Inducers and DNA Intercalators. Part I. Derivatives of 1, 8-Diazafluorene—The Novel Analogues of Tilorone", Heterocycles, Elsevier Science Publishers B.V. Amsterdam, NL, vol. 22, No. 1, Jan. 1, 1984, pp. 73-78, XP000926459.

Gusak K N et al, "Oxidation of 4,7-phenanthroline derivatives", Russian Journal of Organic Chemistry,Nauka/Interperiodica, MO, vol. 40, No. 9, Sep. 1, 2004, pp. 1322-1328, XP019301794.

* cited by examiner

CONJUGATED COMPOUND, NITROGENATED CONDENSED-RING COMPOUND, NITROGENATED CONDENSED-RING POLYMER, ORGANIC THIN FILM, AND ORGANIC THIN FILM ELEMENT

CROSS REFERENCE TO RELATED APPLICATIONS

This application is a National Stage of International Application No. PCT/JP2008/071520 filed Nov. 27, 2008, and claims priority under 35 U.S.C. §119 to Japanese Patent Application Nos. 2007-311381, 2008-031972 and 2008-220031 filed Nov. 30, 2007, Feb. 13, 2008 and Aug. 28, 2008, respectively, the contents of all of which are incorporated herein by reference in their entirety.

TECHNICAL FIELD

The present invention relates to a conjugated compound, a nitrogen-containing fused-ring compound, a nitrogen-containing fused-ring polymer, an organic thin film, and an organic thin film device.

BACKGROUND ART

A variety of conjugated compounds have been developed as organic n-type semiconductors, for use as materials in organic thin film devices such as organic transistors, organic solar cells and optical sensors. Specific examples include compounds with fluoroalkyl groups introduced into oligothiophenes (Patent documents 1-4).

Thin films containing organic materials with electron transport or hole transport properties have potential applications in organic thin-film devices including organic thin-film transistors, organic solar cells, optical sensors and the like, and because organic n-type semiconductors (that exhibit electron transport properties) are harder to obtain than organic p-type semiconductors (that exhibit hole transport properties), a great deal of research is being centered on developing organic n-type semiconductors.

In recent years, much research has been conducted on compounds having thiophene rings, fluoroalkyl groups introduced into which, with increased electron acceptability of π-conjugated compounds, as electron transport materials for organic n-type semiconductors and the like (Patent document 1).

On the other hand, several polythiophenes having crosslinked structures are also being studied in order to improve planarity in the molecular structure (Patent document 5).

[Patent document 1] U.S. Patent Application Publication No. 2004/186266
[Patent document 2] U.S. Patent Application Publication No. 2004/183068
[Patent document 3] International Patent Publication No. WO2003/010778
[Patent document 4] European Patent Application Publication No. 1279689
[Patent document 5] Japanese Unexamined Patent Application Publication No. 2004-339516

DISCLOSURE OF THE INVENTION

Problems to be Solved by the Invention

The compounds described in Patent documents 1-4, however, cannot be utilized as organic n-type semiconductors with satisfactory electron transport properties.

The performance of even the known materials described in Patent documents 1 and 5, as organic n-type semiconductors, is not sufficient, and organic n-type semiconductors with further improved electron transport properties are desired.

It is therefore an object of the present invention to provide novel compounds and novel polymers that can be used as organic n-type semiconductors with excellent electron transport properties. It is another object of the present invention to provide organic thin films containing the novel compounds and/or novel polymers and organic thin-film devices comprising the organic thin films.

Means for Solving the Problems

The first invention group will be explained first.
In order to achieve the object stated above, the present invention provides a conjugated compound having two or more groups represented by the following formula (I) or the following formula (II).

[Chemical Formula 1]

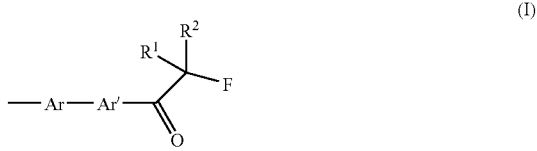

One of Ar and Ar' represents a C6 or greater divalent aromatic hydrocarbon group and the other represents a C4 or greater divalent heterocyclic group, wherein the groups each may have a substituent, with the proviso that the groups as a whole contain no fluorine atoms, $R^1$ and $R^2$ each independently represent a hydrogen atom, a halogen atom or a monovalent group, and Ar" represents a trivalent aromatic hydrocarbon or trivalent heterocyclic group, which may have a substituent. However, when the conjugated compound has two or more groups represented by formula (I), the portion excluding these groups contain no fluorine atoms.

A conjugated compound with such a backbone has an excellent packing property between molecules, and can exhibit a sufficiently low LUMO due to introduction of the α-fluoroketone structure (—C(=O)—C(F)<). The conjugated compound is therefore sufficiently suitable as an n-type semiconductor with excellent electron injection and electron transport properties. Such compounds are also chemically stable and have excellent solubility in solvents, and therefore by allowing thin films to form using the conjugated compounds, the organic thin-film devices with excellent performance can be produced.

The present invention provides organic thin films comprising the aforementioned conjugated compounds. The present invention further provides organic thin-film devices, organic thin-film transistors, organic solar cells and optical sensors comprising the organic thin films.

Because such organic thin films, organic thin-film devices, organic thin-film transistors, organic solar cells and optical sensors have sufficiently low LUMO and are formed using conjugated compounds of the present invention exhibiting excellent charge transport properties as mentioned above, it is possible to achieve excellent performance.

The second invention group will now be explained.

In order to achieve the object stated above, the present invention further provides nitrogen-containing fused-ring compounds represented by the following formula (α-I).

[Chemical Formula 2]

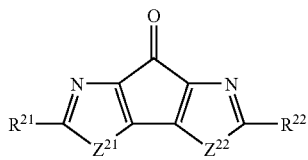

(α-I)

In formula (α-I), $R^{21}$ and $R^{22}$ each independently represent a hydrogen atom, a halogen atom or an optionally substituted monovalent group, and $Z^{21}$ and $Z^{22}$ each independently represent any one of the groups represented by the following formulas (α-i)-(α-ix).

[Chemical Formula 3]

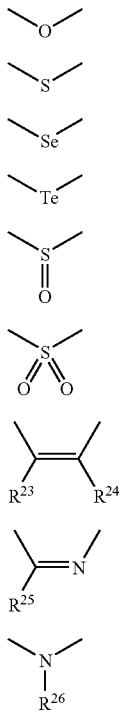

(α-i)
(α-ii)
(α-iii)
(α-iv)
(α-v)
(α-vi)
(α-vii)
(α-viii)
(α-ix)

In the formulas, $R^{23}$, $R^{23}$, $R^{25}$ and $R^{26}$ each independently represents a hydrogen atom, a halogen atom or a monovalent group, and $R^{23}$ and $R^{24}$ may bond together to form a ring. The left side and the right side of the group represented by formula (α-viii) may be interchanged.

The present invention still further provides a nitrogen-containing fused-ring polymer having a repeating unit represented by the following formula (α-II).

[Chemical Formula 4]

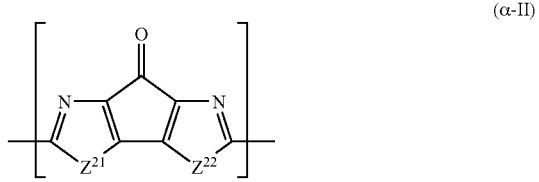

(α-II)

In formula (α-II), $Z^{21}$ and $Z^{22}$ each independently represent any one of the groups represented by the following formulas (α-i)-(α-ix).

[Chemical Formula 5]

(α-i)
(α-ii)
(α-iii)
(α-iv)
(α-v)
(α-vi)
(α-vii)
(α-viii)
(α-ix)

In the formulas, $R^{23}$, $R^{24}$, $R^{25}$ and $R^{26}$ each independently represents a hydrogen atom, a halogen atom or a monovalent group, and $R^{23}$ and $R^{24}$ may bond together to form a ring. The left side and the right side of the group represented by formula (α-viii) may be interchanged.

Nitrogen-containing fused-ring compounds and nitrogen-containing fused-ring polymers comprising such a backbone have satisfactory π-conjugated planarity between the rings and can exhibit a sufficiently low LUMO due to introduction of the nitrogen-containing fused rings, and can therefore be used as organic n-type semiconductors with excellent electron transport properties. Such nitrogen-containing fused-ring compounds and nitrogen-containing fused-ring polymers are also chemically stable and have excellent solubility in organic solvents, and therefore by allowing thin films to form using them, the organic thin-film devices with excellent performance can be produced.

The nitrogen-containing fused-ring compounds and nitrogen-containing fused-ring polymers of the present invention are also environmentally stable and have excellent solubility in organic solvents, and can therefore be used to form thin films to allow production of organic thin-film devices with stable performance even in ordinary air.

The present invention still further provides organic thin films containing the nitrogen-containing fused-ring compounds and/or nitrogen-containing fused-ring polymers, and organic thin-film devices comprising the organic thin films.

Because such organic thin films and organic thin-film devices contain nitrogen-containing fused-ring compounds or nitrogen-containing fused-ring polymers according to the present invention, they have sufficiently low LUMO and exhibit excellent electron transport properties.

Effect of the Invention

According to the first invention group it is possible to provide novel conjugated compounds that can be used as organic n-type semiconductors with excellent electron transport properties. It is also possible to provide organic thin films containing the novel conjugated compounds, and organic thin-film devices comprising the organic thin films.

According to the second invention group, it is possible to provide novel nitrogen-containing fused-ring compounds and novel nitrogen-containing fused-ring polymers that can be used as organic n-type semiconductors with excellent electron transport properties. It is also possible to provide organic thin films containing the nitrogen-containing fused-ring compounds or nitrogen-containing fused-ring polymers, and organic thin-film devices comprising the organic thin films.

EXPLANATION OF SYMBOLS

Figure 1:
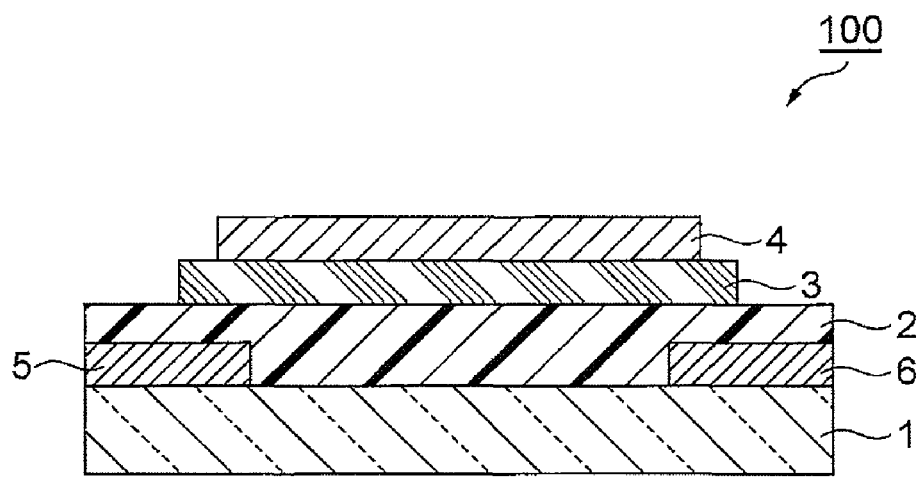
FIG. 1 is a schematic cross-sectional view of an organic thin-film transistor according to a first embodiment.

1: Substrate, 2: active layer, 2a: active layer, 3: insulating layer, 4: gate electrode, 5: source electrode, 6: drain electrode, 7a: first electrode, 7b: second electrode, 8: charge generation layer, 100: organic thin-film transistor according to first embodiment, 110: organic thin-film transistor according to second embodiment, 120: thin-film transistor according to third embodiment of organic, 130: organic thin-film transistor according to fourth embodiment, 140: organic thin-film transistor according to fifth embodiment, 150: organic thin-film transistor according to sixth embodiment, 160: organic thin-film transistor according to seventh embodiment, 200: solar cell according to embodiment, 300: optical sensor according to first embodiment, 310: optical sensor according to second embodiment, 320: optical sensor according to third embodiment.

BEST MODE FOR CARRYING OUT THE INVENTION

Preferred embodiments of the present invention will now be explained in detail, with reference to the accompanying drawings as necessary. Throughout the drawings, corresponding elements will be referred to by like reference numerals and will be explained only once. Unless otherwise specified, the vertical and horizontal positional relationships are based on the positional relationships in the drawings. Also, the dimensional proportions depicted in the drawings are not necessarily limitative.

The first invention group will be explained in detail first.

A conjugated compound of the present invention has two or more groups represented by the above formula (I) or (II). A conjugated compound, according to the present invention, is a compound comprising a structure with a single bond and an unsaturated bond, lone electron pair, radical or nonbonded orbital, alternately linked, in the main backbone, with delocalization of electrons due to interaction between π-orbitals or nonbonded orbitals, in part or across the entire main backbone. It is preferable that the conjugated compounds are π-conjugated compounds due to interaction between n-orbitals.

When the conjugated compound has two or more groups represented by formula (I), the portion excluding the groups contain no fluorine atoms. Such conjugated compounds have sufficiently high packing property between molecules and are sufficiently suitable as re-type semiconductors with excellent electron injection and electron transport properties.

A plurality of groups represented by formula (I) or (II) in the conjugated compound may be the same or different, but it is preferable that they are the same.

In formula (I), one of Ar and Ar' is a C6 or greater divalent aromatic hydrocarbon group and the other is a C4 or greater divalent heterocyclic group. These groups may have substituents, but contain no fluorine atoms as a whole. It is preferable that Ar is a C4 or greater divalent heterocyclic group and Ar' is a C6 or greater divalent aromatic hydrocarbon group. $R^1$ and $R^2$ each independently represent a hydrogen atom, a halogen atom or a monovalent group.

A divalent aromatic hydrocarbon group is an atomic group remaining after removing two hydrogen atoms from a benzene ring or fused ring. The number of carbon atoms in the divalent aromatic hydrocarbon group is preferably 6 to 60 and more preferably 6 to 20. Examples of fused rings include naphthalene, anthracene, tetracene, pentacene, pyrene, perylene and fluorene. Preferred among these are atomic groups remaining after removing two hydrogen atoms from a benzene, pentacene or pyrene ring. The aromatic hydrocarbon groups may be optionally substituted. The numbers of carbon atoms of the substituents are not included in the number of carbon atoms in the divalent aromatic hydrocarbon groups. As substituents there may be mentioned halogen atoms, saturated or unsaturated hydrocarbon groups, aryl groups, alkoxy groups, arylalkyl groups, aryloxy groups, monovalent heterocyclic groups, amino groups, nitro groups and cyano groups.

A divalent heterocyclic group is an atomic group remaining after removing two hydrogens from a heterocyclic compound. The number of carbon atoms in the divalent heterocyclic group is preferably 4 to 60 and more preferably 4 to 20. The divalent heterocyclic group may have substituents, and the numbers of carbons of the substituents are not included in the number of carbons in the divalent heterocyclic group. As substituents there may be mentioned halogen atoms, saturated or unsaturated hydrocarbon groups, aryl groups, alkoxy groups, arylalkyl groups, aryloxy groups, monovalent heterocyclic groups, amino groups, nitro groups and cyano groups. Examples of divalent heterocyclic groups include atomic groups remaining after removing two hydrogen atoms from a thiophene ring, thienothiophene ring, furan ring, pyrrole ring or pyridine ring, and particularly atomic groups remaining after removing two hydrogen atoms from a thiophene ring or thienothiophene ring can be expected to exhibit characteristic electrical properties and novel electrical properties not found in the prior art. It is preferable that the divalent heterocyclic groups are divalent aromatic heterocyclic groups.

A heterocyclic compound is an organic compound with a ring structure, the elements composing the ring of which include not only carbon but also heteroatoms such as oxygen, sulfur, nitrogen, phosphorus, boron and silicon.

Examples of halogen atoms include fluorine atoms, chlorine atoms, bromine atoms and iodine atoms. $R^1$ and $R^2$ are preferably fluorine atoms, from the viewpoint of obtaining even lower LUMO.

The groups represented by the above formula (I) are preferably groups represented by the following formula (III).

[Chemical Formula 6]

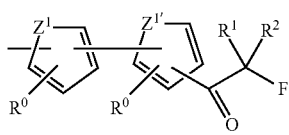

(III)

independently represent a hydrogen atom or a monovalent group, and $R^3$ and $R^4$ may bond together to form a ring.

[Chemical Formula 7]

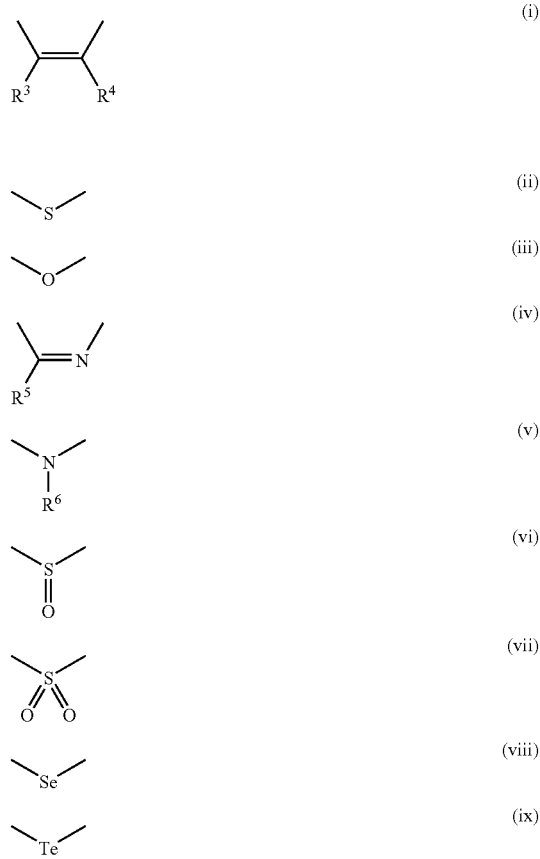

When the conjugated compound has two or more groups represented by formula the (I) or (III), it is preferable that the compound is represented by the following formula (V).

[Chemical Formula 8]

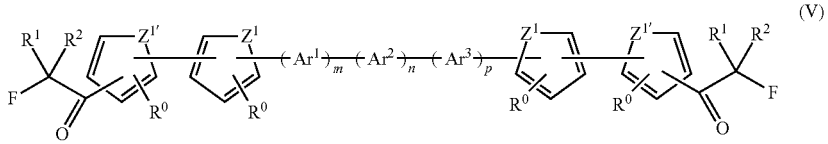

(V)

In formula (III), $R^1$ and $R^2$ each independently represents a hydrogen atom, a halogen atom or a monovalent group, and $R^0$ represents hydrogen, a C1 to C20 alkyl group or a C1 to C20 alkoxy group, wherein a plurality of the groups in $R^0$ may be the same or different. One of $Z^1$ and $Z^{1'}$ is a group represented by the following formula (i), and the other is a group represented by any one of the following formulas (ii)-(ix). It is preferable that $Z^{1'}$ is a group represented by the following formula (i), and $Z^1$ is any one of the groups represented by the following formulas (ii)-(ix). Also, $R^3$, $R^4$, $R^5$ and $R^6$ each In formula (V), $R^0$, $R^1$, $R^2$, $Z^1$ and $Z^{1'}$ have the same definitions as above. $Ar^1$, $Ar^2$ and $Ar^3$ each independently represent a C6 or greater divalent aromatic hydrocarbon or C4 or greater divalent heterocyclic group. These groups may have substituents, but contain no fluorine atoms as a whole. As divalent aromatic hydrocarbons and C4 or greater divalent heterocyclic groups there may be mentioned the same groups as those mentioned for Ar and Ar'. It is preferable that at least one of $Ar^1$, $Ar^2$ and $Ar^3$ is an optionally substituted thienylene group but it as a whole contains no fluorine atoms. The letters m, n and p each independently represent an integer of 0 to 6.

When a plurality of the groups in $R^0$, $R^1$, $R^2$, $Z^1$ and $Z^{1'}$ are present they may be the same or different. From the viewpoint of more effectively exhibiting the effect of the present invention, it is more preferable that $R^1$ and $R^2$ are fluorine atoms, $Z^{1'}$ is a group represented by formula (i) and $Z^1$ is a group represented by formula (ii). It is most preferable that at least one of $Ar^1$, $Ar^2$ and $Ar^3$ is a thienylene group.

In the above formula (II), Ar" represents a trivalent aromatic hydrocarbon or trivalent heterocyclic group, wherein the groups may be optionally substituted.

A trivalent aromatic hydrocarbon group is an atomic group remaining after removing three hydrogen atoms from a benzene ring or fused ring. The number of carbon atoms in the trivalent aromatic hydrocarbon group is preferably 6 to 60 and more preferably 6 to 20. Examples of fused rings include naphthalene, anthracene, tetracene, pentacene, pyrene, perylene and fluorene. Particularly preferred among these are atomic groups remaining after removing three hydrogen atoms from a benzene ring. The aromatic hydrocarbon groups may be optionally substituted. The numbers of carbon atoms of the substituents are not included in the number of carbon atoms in the trivalent aromatic hydrocarbon groups.

A trivalent heterocyclic group is an atomic group remaining after removing two hydrogen atoms from a heterocyclic compound. The number of carbon atoms in the trivalent heterocyclic group is preferably 4 to 60 and more preferably 4 to 20. The trivalent heterocyclic group may have substituents, and the numbers of carbons of the substituents are not included in the number of carbons in the trivalent heterocyclic group. Examples of trivalent heterocyclic groups include atomic groups remaining after removing three hydrogens from a thiophene ring, thienothiophene ring, furan ring, pyrrole ring or pyridine ring, and particularly atomic groups remaining after removing three hydrogens from a thiophene ring or thienothiophene ring can be expected to exhibit characteristic electrical properties and novel electrical properties not found in the prior art. It is preferable that the trivalent heterocyclic groups are trivalent aromatic heterocyclic groups.

It is preferable that the groups represented by the above formula (II) are groups represented by the following formula (IV).

[Chemical Formula 9]

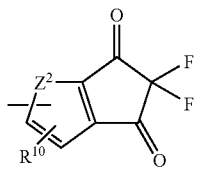

(IV)

In formula (IV), $R^{10}$ represents a hydrogen atom, a fluorine atom, a C1 to C20 alkyl group, a C1 to C20 fluoroalkyl group, a C1 to C20 alkoxy group or a C1 to C20 fluoroalkoxy group, and $Z^2$ represents any one of the groups represented by the following formulas (xi)-(xix). It is preferable that $Z^2$ is a group represented by the following formula (xii). Also, $R^{13}$, $R^{14}$, $R^{15}$ and $R^{16}$ each independently represent a hydrogen atom, a halogen atom or a monovalent group, and $R^{13}$ and $R^{14}$ may bond together to form a ring.

[Chemical Formula 10]

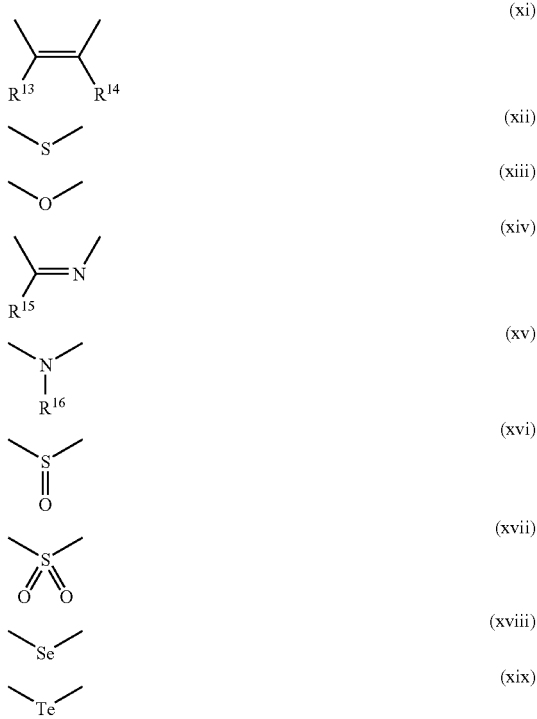

When the conjugated compound has two or more groups represented by formula (II) or (IV), it is preferably a compound represented by the following formula (VI).

[Chemical Formula 11]

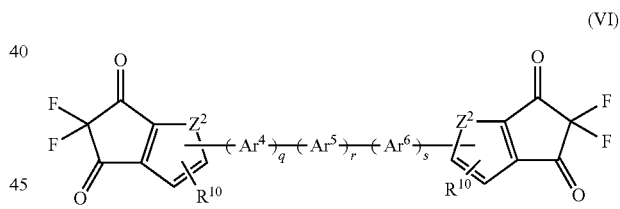

(VI)

In formula (VI), each $R^{10}$ and each $Z^2$ have the same definitions as above, and a plurality of the groups in $R^{10}$ and $Z^2$ may be the same or different. $Ar^4$, $Ar^5$ and $Ar^6$ each independently represent a C6 or greater divalent aromatic hydrocarbon or C4 or greater divalent heterocyclic group, wherein the groups may be optionally substituted. As divalent aromatic hydrocarbons and C4 or greater divalent heterocyclic groups there may be mentioned the same groups as those mentioned for Ar and Ar'. It is more preferable that at least one of $Ar^4$, $Ar^5$ and $Ar^6$ is an optionally substituted thienylene group. The letters q, r and s each independently represent an integer of 0 to 6. From the viewpoint of more effectively exhibiting the effect of the present invention, it is preferable that $Z^2$ is a group represented by formula (xii).

As alkyl groups for $R^0$ and $R^{10}$ there may be mentioned C1 to C20 straight-chain, branched or cyclic alkyl groups, with C1 to C12 straight-chain, branched and cyclic alkyl groups being preferred. Examples of such alkyl groups include methyl groups, ethyl groups, n-propyl groups, iso-propyl groups, n-butyl groups, iso-butyl groups, tert-butyl groups, 3-methylbutyl groups, pentyl groups, hexyl groups, 2-ethylhexyl groups, heptyl groups, octyl groups, nonyl groups, decyl groups, lauryl groups, cyclopropyl groups, cyclobutyl groups, cyclopentyl groups, cyclohexyl groups, cycloheptyl groups, cyclooctyl groups, cyclononyl groups and cyclododecyl groups. As alkoxy groups there may be mentioned C1 to C20 alkoxy groups comprising the above alkyl groups in their structures. As alkoxy groups there may be mentioned C1 to C20 straight-chain, branched or cyclic alkoxy groups comprising the above alkyl groups in their structures, and it is preferable that the alkoxy groups comprise C1 to C12 straight-chain, branched and cyclic alkyl groups. As fluoroalkyl groups for $R^{10}$ there may be mentioned the aforementioned alkyl groups having some or all of their hydrogen atoms replaced with fluorine atoms, and it is preferable that the fluoroalkyl groups comprise C1 to C12 straight-chain, branched and cyclic fluoroalkyl groups. As fluoroalkoxy groups there may be mentioned C1 to C20 fluoroalkoxy groups comprising the above fluoroalkyl groups in their structures, and it is preferable that the fluoroalkoxy groups comprise C1 to C12 straight-chain, branched and cyclic fluoroalkyl groups.

Examples of monovalent groups for $R^1$, $R^2$, $R^3$, $R^4$, $R^5$, $R^6$, $R^{13}$, $R^{14}$, $R^{15}$ and $R^{16}$ include straight-chain or branched low molecular chains, C3 to C60 monovalent cyclic groups, wherein they may be either monocyclic or fused rings, carbon rings or heterocyclic rings, saturated or unsaturated, and optionally substituted, saturated or unsaturated hydrocarbon groups, hydroxyl groups, alkoxy groups, alkanoyloxy groups, amino groups, oxyamino groups, alkylamino groups, dialkylamino groups, alkanoylamino groups, cyano groups, nitro groups or sulfo groups, alkyl groups substituted with halogen atoms, alkoxysulfonyl groups, wherein the alkoxy groups may be optionally substituted with halogen atoms, alkylsulfonyl groups wherein the alkyl groups may be optionally substituted with halogen atoms, sulfamoyl groups, alkylsulfamoyl groups, carboxyl groups, carbamoyl groups, alkylcarbamoyl groups, alkanoyl groups and alkoxycarbonyl groups.

As alkyl groups there may be mentioned C1 to C20 straight-chain, branched or cyclic alkyl groups, and it is preferable that the alkyl groups are C1 to C12 straight-chain, branched and cyclic alkyl groups. Examples of alkyl groups include methyl groups, ethyl groups, n-propyl groups, iso-propyl groups, n-butyl groups, iso-butyl groups, tent-butyl groups, 3-methylbutyl groups, pentyl groups, hexyl groups, 2-ethylhexyl groups, heptyl groups, octyl groups, nonyl groups, decyl groups, lauryl groups, cyclopropyl groups, cyclobutyl groups, cyclopentyl groups, cyclohexyl groups, cycloheptyl groups, cyclooctyl groups, cyclononyl groups and cyclododecyl groups. The same is applied for groups comprising alkyl groups in their structures (for example, alkoxy groups, alkylamino groups and alkoxycarbonyl groups).

There are also no particular restrictions on unsaturated hydrocarbon groups, and examples include vinyl groups, 1-propenyl groups, allyl groups, propargyl groups, isopropenyl groups, 1-butenyl groups and 2-butenyl groups.

There are no particular restrictions on alkanoyl groups, and examples include formyl groups, acetyl groups, propionyl groups, isobutyryl groups, valeryl groups and isovaleryl groups. The same is applied for groups comprising alkanoyl groups in their structures (for example, alkanoyloxy groups and alkanoylamino groups). A "C1 alkanoyl group" is formyl groups, which also is applied for groups containing alkanoyl groups in their structures.

The conjugated compounds of the present invention are expected to have high electron transport properties as organic n-type semiconductors. In order to make the effect increase, it is preferable to make the compounds readily adopt a π-π stack structure by increasing the planarity of the π-conjugated structure other than the groups represented by formula (I) or (II). From this viewpoint, $Ar^1$, $Ar^2$ and $Ar^3$ in formula (V) and $Ar^4$, $Ar^5$ and $Ar^6$ in formula (VI) preferably have structures comprising fused rings or thiophene rings. It is especially preferable that the structure comprises the thiophene backbone since the plane spacing in the π-π stack structure can be reduced. From the viewpoint of improving solubility in organic solvents and retaining π-conjugated planarity, it is preferable that $Ar^1$, $Ar^2$, $Ar^3$, $Ar^4$, $Ar^5$ and $Ar^6$ have substituents. However, the compound as a whole preferably contains no fluorine atoms.

A conjugated compound of the present invention has two or more groups represented by formula (I), (II), (III) or (IV). From the viewpoint of increasing the electron transport property, it is preferable that the conjugated compound is a compound represented by the above formula (V) or (VI). As specific compounds represented by the above formula (V) or (VI) there may be mentioned compounds represented by the following formulas (1)-(20).

[Chemical Formula 12]

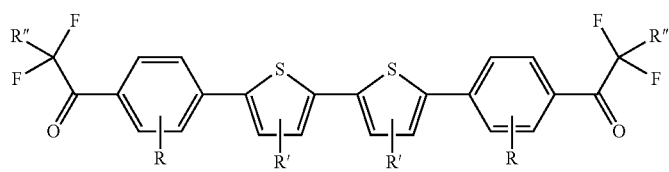

(1)

[Chemical Formula 13]

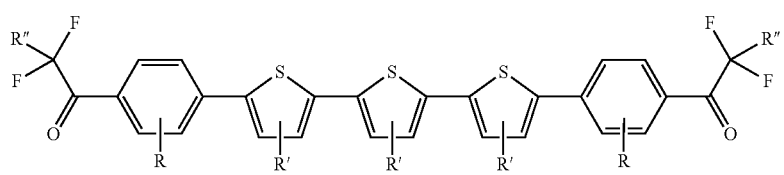

(2)

-continued
[Chemical Formula 14]
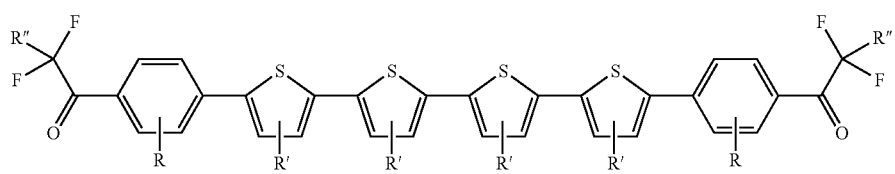
(3)
[Chemical Formula 15]
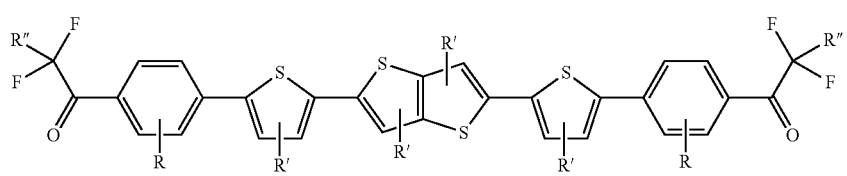
(4)
[Chemical Formula 16]
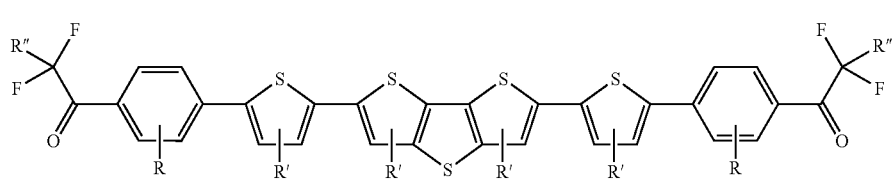
(5)
[Chemical Formula 17]
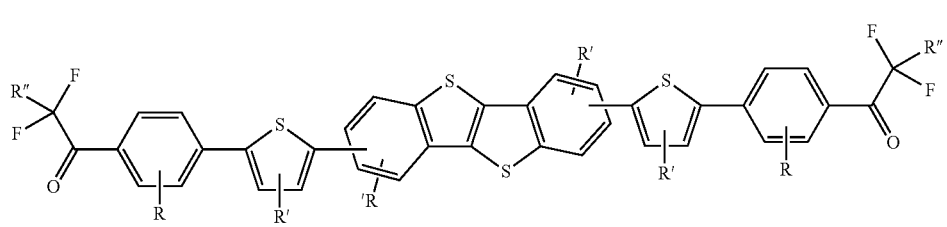
(6)
[Chemical Formula 18]
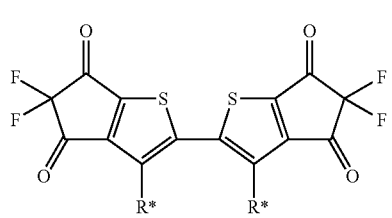
(7)
[Chemical Formula 19]
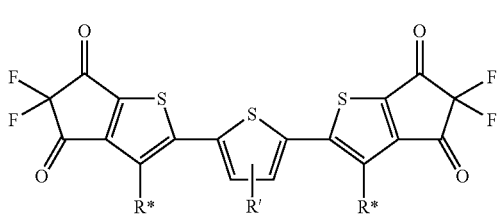
(8)
[Chemical Formula 20]
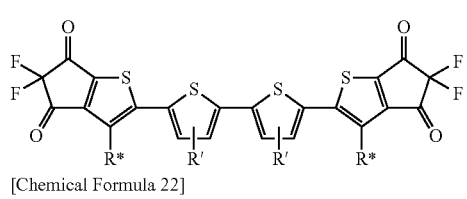
(9)
[Chemical Formula 21]
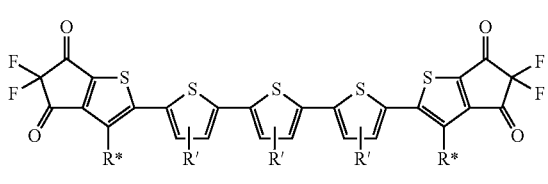
(10)
[Chemical Formula 22]
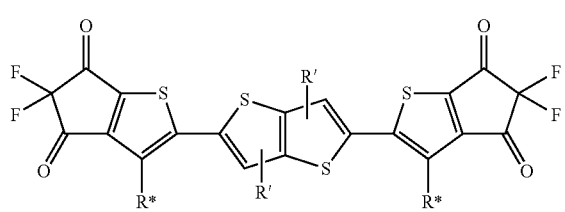
(11)

[Chemical Formula 23]
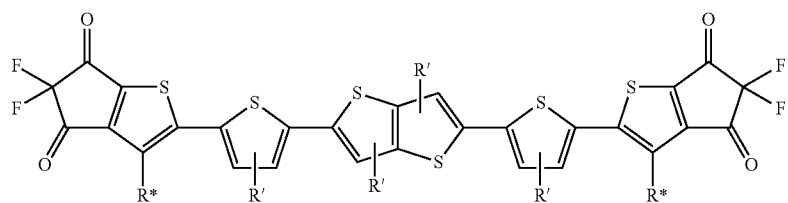
(12)
[Chemical Formula 24]
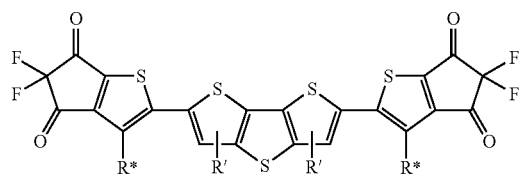
(13)
[Chemical Formula 25]
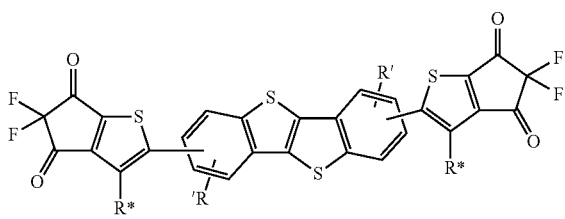
(14)
[Chemical Formula 26]
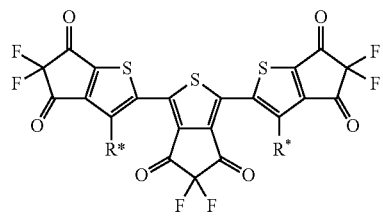
(15)
[Chemical Formula 27]
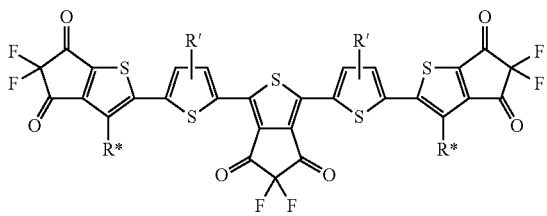
(16)
[Chemical Formula 28]
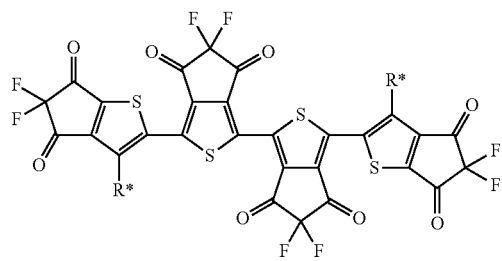
(17)
[Chemical Formula 29]
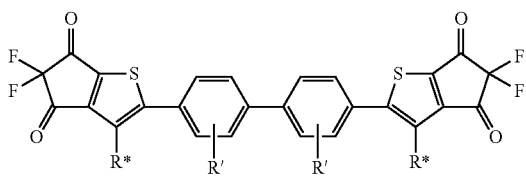
(18)
[Chemical Formula 30]
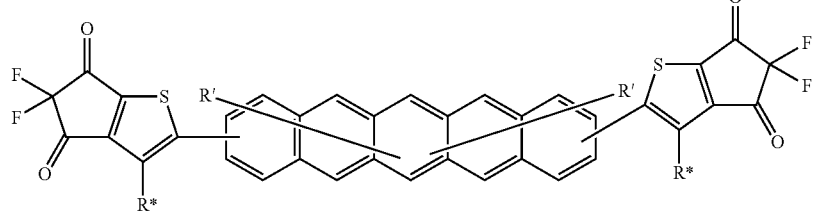
(19)

[Chemical Formula 31]

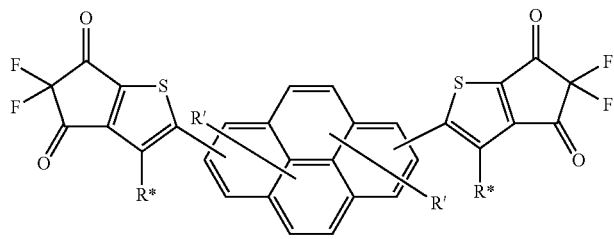
(20)

In these formulas, R represents a hydrogen atom, a C1 to C20 alkyl group or a C1 to C20 alkoxy group. R*, R' and R" represent hydrogen atoms, fluorine atoms, or C1 to C20 alkyl groups, C1 to C20 fluoroalkyl groups, C1 to C20 alkoxy group or C1 to C20 fluoroalkoxy groups. A plurality of the groups in R, R*, R' and R" may be the same or different. Of these, it is preferable that R, R* and R' are preferably hydrogen atoms or C1 to C20 alkyl groups, and R" is a fluorine atom or C1 to C20 fluoroalkyl group.

The conjugated compounds of the present invention have a reduction potential based on ferrocene, as determined by electrochemical measurement (cyclic voltammetry), of preferably −2.0 V to +0.5 V and more preferably −1.8 V to +0.2 V. If the reduction potential is within this numerical range, the conjugated compound will be sufficiently suitable as an n-type semiconductor with excellent electron injection and excellent electron transport properties. The reduction potential can be measured by the following method. The supporting electrolyte, solvent and electrodes used for the measurement are not limited to the examples mentioned below, and may be as desired so long as they permit similar measurement.

The material to be measured is dissolved to about 0.1-2 mM in an organic solvent containing about 0.1 mol/L tetrabutylammonium perchlorate and tetrabutylammonium hexafluorophosphate, as examples of supporting electrolytes. The obtained solution is subjected to dry nitrogen bubbling, reduced pressure deaeration, ultrasonic irradiation or the like to remove the oxygen, and then a platinum electrode or glassy carbon electrode, for example, is used as the work electrode with a platinum electrode, for example, as the counter electrode, for electrolytic reduction from an electrically neutral state at a sweep rate of 100 mV/sec. The potential of the first peak value detected during electrolytic reduction is compared with the oxidation-reduction potential of a reference material such as ferrocene, to obtain the oxidation (or reduction) potential for the material being measured. The value of the oxidation (or reduction) potential obtained in this manner converted based on ferrocene is the reduction potential according to the present invention.

A method for producing a conjugated compound of the present invention will now be explained. The conjugated compound can be produced by reacting compounds represented by the following formulas (VIIa), (VIIb), (VIIIa) (VIIIb), (IX), (IX'), (X), (X'), (XIa), (XIb), (XIIa) and (XIIb) (hereunder also referred to as "(VIIa)-(XIIb)") as starting materials.

[Chemical Formula 32]

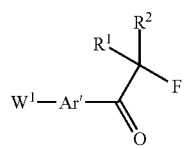
(VIIa)

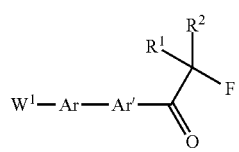
(VIIb)

[Chemical Formula 33]

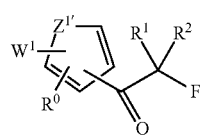
(VIIIa)

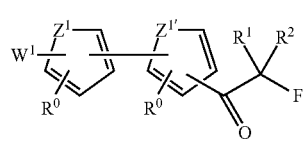
(VIIIb)

[Chemical Formula 34]

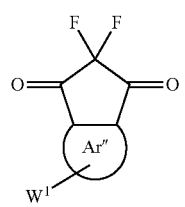
(IX)

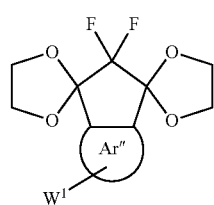
(IX')

-continued

[Chemical Formula 35]

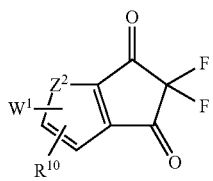

(X)

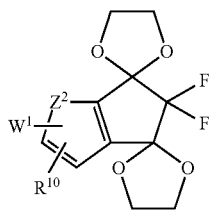

(X')

[Chemical Formula 36]

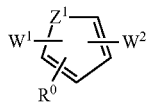

(XIa)

W¹—Ar—W²

(XIb)

[Chemical Formula 37]

(XIIa)

$W^1{-}(Ar^1)_m{-}(Ar^2)_n{-}(Ar^3)_p{-}W^2$ (XIIb)

$W^1{-}(Ar^4)_q{-}(Ar^5)_r{-}(Ar^6)_s{-}W^2$

In formulas (VIIa)-(XIIb), Ar, Ar', Ar'', $Ar^1$, $Ar^2$, $Ar^3$, $Ar^4$, $Ar^5$, $Ar^6$, $Z^1$, $Z^{1'}$, $Z^2$, $R^0$, $R^{10}$, $R^1$, $R^2$, m, n, p, q, r and s have the same definitions as above. $W^1$ and $W^2$ each independently represent a halogen atom or an alkyl sulfonate, aryl sulfonate, arylalkyl sulfonate, boric acid ester residue, sulfoniummethyl, phosphoniummethyl, phosphonatemethyl, monohalogenated methyl, boric acid residue (—B(OH)₂), formyl, trialkylstannyl or vinyl group. Specific examples of boric acid ester residue groups include dimethylboric acid, diisopropylboric acid, 1,3,2-dioxaborolane, 4,4,5,5-tetraethyl-1,3,2-dioxaborolane and 1,3,2-dioxaborolane.

From the viewpoint of facilitating synthesis and reaction of the compounds represented by formulas (VIIa)-(XIIb), $W^1$ and $W^2$ preferably each independently represent a halogen atom or an alkyl sulfonate group, aryl sulfonate group, arylalkyl sulfonate group, boric acid ester residue, boric acid residue or trialkylstannyl group. When a compound represented by formula (IX) or (X) is used as the starting material, and its powerful electron-withdrawing property impedes reaction, a compound represented by formula (IX') or (X') with the carbonyl groups replaced by alkylenedioxy groups may be used as an intermediate for reaction, and the alkylenedioxy groups subsequently converted to carbonyl groups.

For example, a compound represented by formula (X') and a compound represented by formula (XIIb) may be reacted to produce a compound represented by the following formula (XIII) as an intermediate, and the alkylenedioxy groups converted to carbonyl groups after the reaction to produce a compound of the above formula (VI).

[Chemical Formula 38]

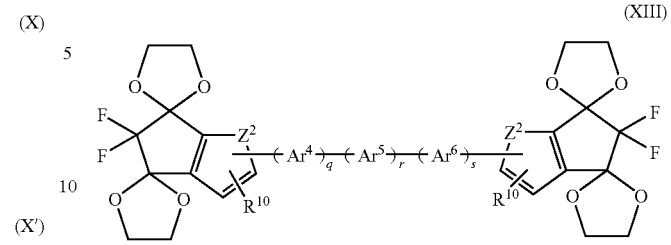

(XIII)

In formula (XIII), $Ar^4$, $Ar^5$, $Ar^6$, $Z^2$, $R^{10}$, q, r and s have the same definitions as above.

Examples of methods for producing the aforementioned conjugated compounds include a method using Suzuki coupling reaction, a method using Grignard reaction, a method using Stille reaction, a method using a Ni(0) catalyst, a method using an oxidizing agent such as $FeCl_3$, a method using anionic oxidation reaction, a method using palladium acetate and an organic base, a method involving preparation of a lithiated derivative from an α-unsubstituted or halogenated compound, and oxidative coupling, a method using electrochemical oxidation reaction, and a method involving decomposition of an intermediate compound with an appropriate leaving group.

Of these, method using Suzuki coupling reaction, method using Grignard reaction, method using Stille reaction, method using Ni(0) catalysts, method using anionic oxidation reaction and method using palladium acetate and organic bases are preferred for easier structural control, ready availability of the starting materials and simplification of the reaction procedure.

Examples of the catalyst used for Suzuki coupling reaction include tetrakis(triphenylphosphine)palladium or palladium acetate, and the reaction may be carried out with addition of at least one equivalent and preferably 1-10 equivalents of an inorganic base such as potassium carbonate, sodium carbonate or barium hydroxide, an organic base such as triethylamine or an inorganic salt such as cesium fluoride, with respect to the monomer. The reaction may be carried out in a two-phase system, with the inorganic salt in aqueous solution. The solvent used for the reaction may be N,N-dimethylformamide, toluene, dimethoxyethane, tetrahydrofuran or the like. The reaction temperature will depend on the solvent used but is preferably about 50-160° C. The temperature may be increased to near the boiling point of the solvent for reflux. The reaction time will be between 1 hour and 200 hours. The Suzuki coupling reaction is described in, for example, Chem. Rev. Vol. 95, p. 2457 (1995).

For reaction using a Ni(0) catalyst, it may include the method may using a zerovalent nickel complex as the Ni(0) catalyst, and method of producing zerovalent nickel in the system by reacting a nickel salt in the presence of reducing agent. Examples of zerovalent nickel complexes include bis(1,5-cyclooctadiene)nickel(0), (ethylene)bis(triphenylphosphine)nickel(0) and tetrakis(triphenylphosphine)nickel, among which bis(1,5-cyclooctadiene)nickel(0) is preferred from the viewpoint of general use and economy.

Addition of a neutral ligand during the reaction is also preferred from the viewpoint of increasing the yield. A "neutral ligand" is a ligand containing no anions or cations, and examples thereof include nitrogen-containing ligands such as 2,2'-bipyridyl, 1,10-phenanthroline, methylenebisoxazoline and N,N'-tetramethylethylenediamine; and tertiary phosphine ligands such as triphenylphosphine, tritolylphosphine, tributylphosphine and triphenoxyphosphine. Nitrogen-containing ligands are preferred from the viewpoint of greater flexibility and lower cost, while 2,2'-bipyridyl is especially preferred from the viewpoint of higher reactivity and yield. For increased conjugated compound yield, a system containing 2,2'-bipyridyl added as a neutral ligand to a system containing bis(1,5-cyclooctadiene)nickel(0) is especially preferred. As nickel salts to be used in the process for producing zerovalent nickel in the system there may be mentioned nickel chloride and nickel acetate. As reducing agents there may be mentioned zinc, sodium hydride, hydrazine and their derivatives, and also lithium aluminum hydride. Ammonium iodide, lithium iodide, potassium iodide and the like may also be used as additives as necessary.

For Stille reaction, the catalyst used may be tetrakis(triphenylphosphine)palladium or palladium acetate, and the reaction may be conducted using an organic tin compound as monomer. The solvent used for the reaction may be N,N-dimethylformamide, toluene, dimethoxyethane, tetrahydrofuran or the like. The reaction temperature will depend on the solvent used but is preferably about 50-160° C. The temperature may be increased to near the boiling point of the solvent for reflux. The reaction time will be between 1 hour and 200 hours.

For a method using anionic oxidation reaction, a halogen- or hydrogen-substituted compound may be used as the monomer for reaction with n-butyllithium to prepare a lithiated derivative, which is then treated with an oxidizing agent such as copper(II) bromide, copper(II) chloride, iron(III) acetylacetonate or the like. The solvent used for the reaction may be toluene, dimethoxyethane, tetrahydrofuran, hexane, heptane, octane or the like. The reaction temperature will depend on the solvent used but is preferably about 50-160° C. The temperature may be increased to near the boiling point of the solvent for reflux. The reaction time will be between 5 minutes and 200 hours.

For a method using palladium acetate and an organic base, a halogen-substituted compound may be used as the monomer and palladium(II) acetate and an organic base such as diisopropylamine or triethylamine added for reaction. The solvent used for the reaction may be N,N-dimethylformamide, toluene, dimethoxyethane, tetrahydrofuran or the like. The reaction temperature will depend on the solvent used but is preferably about 50-160° C. The temperature may be increased to near the boiling point of the solvent for reflux. The reaction time will be between about 5 minutes and 200 hours.

When a conjugated compound of the present invention is to be used as a material for an organic thin-film device, it is preferably subjected to purification treatment by a method such as sublimation purification or recrystallization, since the purity will affect the device characteristics.

An organic thin film according to the present invention will now be explained. The organic thin film of the present invention is one comprising a conjugated compound as described above.

The organic thin film may be one comprising only one of the aforementioned conjugated compounds, or it may include two or more of such conjugated compounds. In order to enhance the electron transport and hole transport properties of the organic thin film, a low molecular compound or high molecular compound having an electron transport or hole transport property (an electron transport material or hole transport material) may also be combined in addition to the conjugated compound.

Any known hole transport material may be used, examples of which include pyrazolines, arylamines, stilbenes, triaryldiamines, oligothiophenes, polyvinylcarbazoles, polysilanes, polysiloxanes with aromatic amines on the side chains or main chain, polyanilines, polythiophenes, polypyrroles, polyarylenevinylenes and polythienylenevinylenes, as well as derivatives of the foregoing.

Any known electron transport materials may also be used, examples of which include metal complexes of oxadiazoles, quinodimethanes, benzoquinones, naphthoquinones, anthraquinones, tetracyanoanthraquinodimethanes, fluorenones, diphenyldicyanoethylenes, diphenoquinones and 8-hydroxyquinolines, polyquinolines, polyquinoxalines, polyfluorenes, $C_{60}$ and other fullerenes, and derivatives of the foregoing.

An organic thin film of the present invention may also contain a charge generation material for generation of an electrical charge upon absorption of light in the organic thin film. Any known charge generation materials may be used, examples of which include azo compounds, diazo compounds, ametallic phthalocyanine compounds, metal phthalocyanine compounds, perylene compounds, polycyclic quinone-based compounds, squarylium compounds, azulenium compounds, thiapyrylium compounds or $C_{60}$ and other fullerenes.

The organic thin film of the present invention may also contain materials necessary for exhibiting various functions. Examples of such materials include sensitizing agents to enhance the function of generating charge by light absorption, stabilizers to increase stability, and UV absorbers for absorption of UV light.

The organic thin film of the present invention may also contain high molecular compound materials as macromolecular binders in addition to the compounds mentioned above, in order to improve the mechanical properties. It is preferable that the macromolecular binders are ones that do not extremely interfere with the electron transport or hole transport property, and ones does not have strong absorption for visible light.

Examples of such macromolecular binders include poly (N-vinylcarbazole), polyaniline, polythiophene, poly(p-phenylenevinylene), poly(2,5-thienylenevinylene), polycarbonate, polyacrylate, polymethyl acrylate, polymethyl methacrylate, polystyrene, polyvinyl chloride, polysiloxane, and derivatives of the foregoing.

There are no particular restrictions on the method for producing an organic thin film of the present invention, and for example, there may be used a method of film formation from a solution comprising the conjugated compound and, as necessary, an electron transport or hole transport material and a macromolecular binder and solvent in admixture therewith. When the conjugated compound has sublimating property, it can be foamed into a thin film by a vacuum vapor deposition method.

The solvent is not particularly restricted so long as it dissolves the conjugated compound and the electron transport or hole transport materials and macromolecular binders combined therewith.

Specific examples of such solvents include unsaturated hydrocarbon-based solvents such as toluene, xylene, mesitylene, tetralin, decalin, bicyclohexyl, n-butylbenzene, sec-butylbenzene and tert-butylbenzene, halogenated saturated hydrocarbon-based solvents such as carbon tetrachloride, chloroform, dichloromethane, dichloroethane, chlorobutane, bromobutane, chloropentane, bromopentane, chlorohexane, bromohexane, chlorocyclohexane and bromocyclohexane, halogenated unsaturated hydrocarbon-based solvents such as chlorobenzene, dichlorobenzene and trichlorobenzene, and ether-based solvents such as tetrahydrofuran and tetrahydropyran. The conjugated compound of the present invention can be dissolved in such solvents to at least 0.1% by mass for most purposes, although this will differ depending on the structure and molecular weight of the compound.

The method for forming the film may be a coating method such as spin coating, casting, microgravure coating, gravure coating, bar coating, roll coating, wire bar coating, dip coating, spray coating, screen printing, flexographic printing, offset printing, ink jet printing, dispenser printing, nozzle coating or capillary coating. Particularly preferred are spin coating, flexographic printing, ink jet printing, dispenser printing, nozzle coating and capillary coating.

The film thickness of the organic thin film is preferably about 1 nm-100 μm, more preferably 2 nm-1000 nm, even more preferably 5 nm-500 nm and most preferably 20 nm-200 nm.

The step of producing the organic thin film of the present invention may also include a step of orienting the conjugated compound. An organic thin film having the conjugated compound oriented by such a step will have the main chain molecules or side chain molecules aligned in a single direction, thus improving the electron mobility or hole mobility.

The method of orienting the conjugated compound may be a known method for orienting liquid crystals. Rubbing, photoorientation, shearing (shear stress application) and pull-up coating methods are convenient, useful and easy orienting methods, and rubbing and shearing are preferred.

Since the organic thin film of the present invention has an electron transport or hole transport property, by controlling the transport of electrons or holes introduced from the electrode or charge generated by photoabsorption, the organic thin film can be used in various organic thin-film devices such as organic thin-film transistors or organic photoelectric conversion devices (organic solar cells, optical sensors and the like). When an organic thin film of the present invention is used in such organic thin-film devices, it is preferably used after orientation by orienting treatment in order to further enhance the electron transport or hole transport property.

Application of an organic thin film of the present invention to an organic thin-film transistor will now be explained. The organic thin-film transistor may have a structure comprising a source electrode and drain electrode, an organic thin-film layer (active layer) containing a conjugated compound according to the present invention which is to act as a current channel between them, and a gate electrode that is to control the level of current flowing through the current channel, and examples of the transistor include a field-effect type or static induction type.

A field-effect type organic thin-film transistor may comprise a source electrode and drain electrode, an organic thin-film layer (active layer) containing a conjugated compound according to the present invention which is to act as a current channel between them, a gate electrode that is to control the level of current flowing through the current channel, and an insulating layer situated between the active layer and the gate electrode. It is preferable that the source electrode and drain electrode are provided in contact with the organic thin-film layer (active layer) containing the conjugated compound of the present invention, and the gate electrode is provided sandwiching the insulating layer which is also in contact with the organic thin-film layer.

A static induction-type organic thin-film transistor comprises a source electrode and drain electrode, an organic thin-film layer containing a conjugated compound according to the present invention which is to act as a current channel between them and a gate electrode that is to control the level of current flowing through the current channel, preferably with the gate electrode in the organic thin-film layer. Most preferably, the source electrode, the drain electrode and the gate electrode formed in the organic thin-film layer are provided in contact with the organic thin-film layer containing the conjugated compound of the present invention. The structure of the gate electrode may be any one formed a current channel for flow from the source electrode to the drain electrode, and that allows the level of current flowing through the current channel to be controlled by the voltage applied to the gate electrode; an example of such a structure is a comb-shaped electrode.

FIG. 1 is a schematic cross-sectional view of an organic thin-film transistor (field-effect type organic thin-film transistor) according to a first embodiment. The organic thin-film transistor 100 shown in FIG. 1 comprises a substrate 1, a source electrode 5 and drain electrode 6 formed at a prescribed spacing on the substrate 1, an active layer 2 formed on the substrate 1 covering the source electrode 5 and drain electrode 6, an insulating layer 3 formed on the active layer 2, and a gate electrode 4 formed on the insulating layer 3 covering the region of the insulating layer 3 between the source electrode 5 and drain electrode 6.

Figure 2:
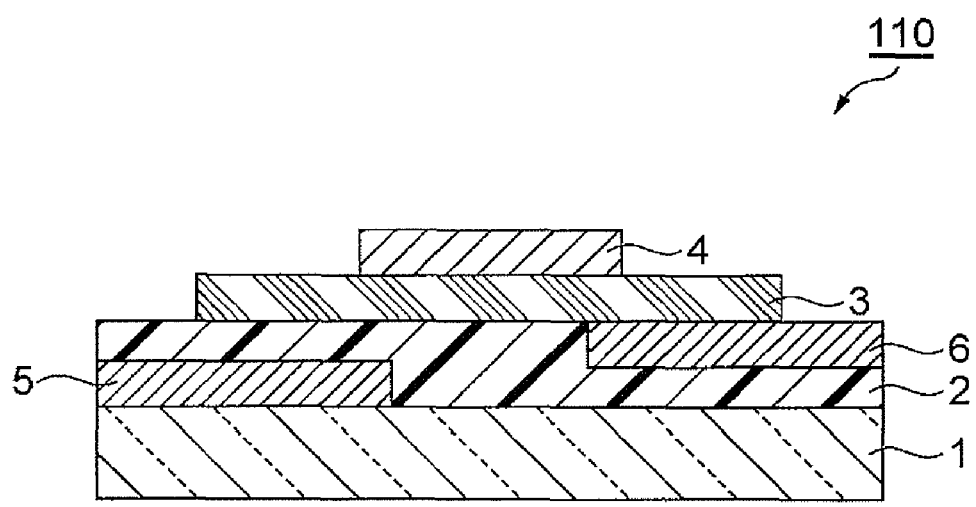
FIG. 2 is a schematic cross-sectional view of an organic thin-film transistor according to a second embodiment.

FIG. 2 is a schematic cross-sectional view of an organic thin-film transistor (field-effect type organic thin-film transistor) according to a second embodiment. The organic thin-film transistor 110 shown in FIG. 2 comprises a substrate 1, a source electrode 5 formed on the substrate 1, an active layer 2 formed on the substrate 1 covering the source electrode 5, a drain electrode 6 formed on the active layer 2 at a prescribed spacing from the source electrode 5, an insulating layer 3 formed on the active layer 2 and drain electrode 6, and a gate electrode 4 formed on the insulating layer 3 covering the region of the insulating layer 3 between the source electrode 5 and drain electrode 6.

Figure 3:
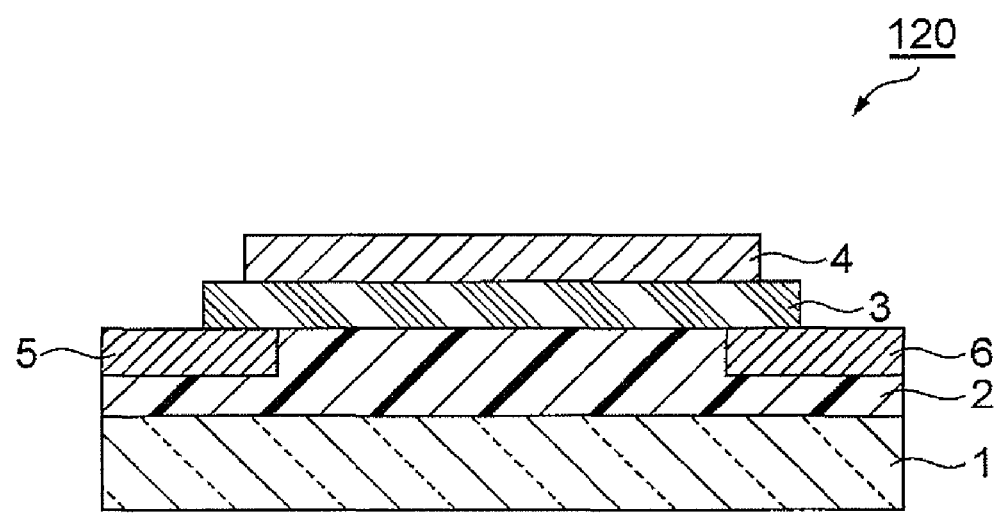
FIG. 3 is a schematic cross-sectional view of an organic thin-film transistor according to a third embodiment.

FIG. 3 is a schematic cross-sectional view of an organic thin-film transistor (field-effect type organic thin-film transistor) according to a third embodiment. The organic thin-film transistor 120 shown in FIG. 3 comprises a substrate 1, an active layer 2 formed on the substrate 1, a source electrode 5 and drain electrode 6 formed at a prescribed spacing on the active layer 2, an insulating layer 3 formed on the active layer 2 covering portions of the source electrode 5 and drain electrode 6, and a gate electrode 4 formed on the insulating layer 3, covering a portion of the region of the insulating layer 3 under which the source electrode 5 is formed and a portion of the region of the insulating layer 3 under which the drain electrode 6 is formed.

Figure 4:
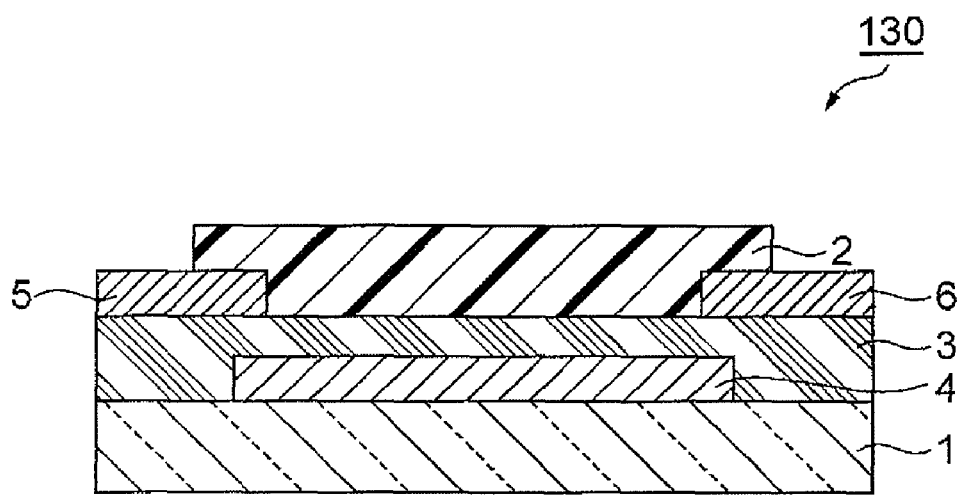
FIG. 4 is a schematic cross-sectional view of an organic thin-film transistor according to a fourth embodiment.

FIG. 4 is a schematic cross-sectional view of an organic thin-film transistor (field-effect type organic thin-film transistor) according to a fourth embodiment. The organic thin-film transistor 130 shown in FIG. 4 comprises a substrate 1, a gate electrode 4 formed on the substrate 1, an insulating layer 3 formed on the substrate 1 covering the gate electrode 4, a source electrode 5 and drain electrode 6 formed at a prescribed spacing on the insulating layer 3 covering portions of the region of the insulating layer 3 under which the gate electrode 4 is formed, and an active layer 2 formed on the insulating layer 3 covering portions of the source electrode 5 and drain electrode 6.

Figure 5:
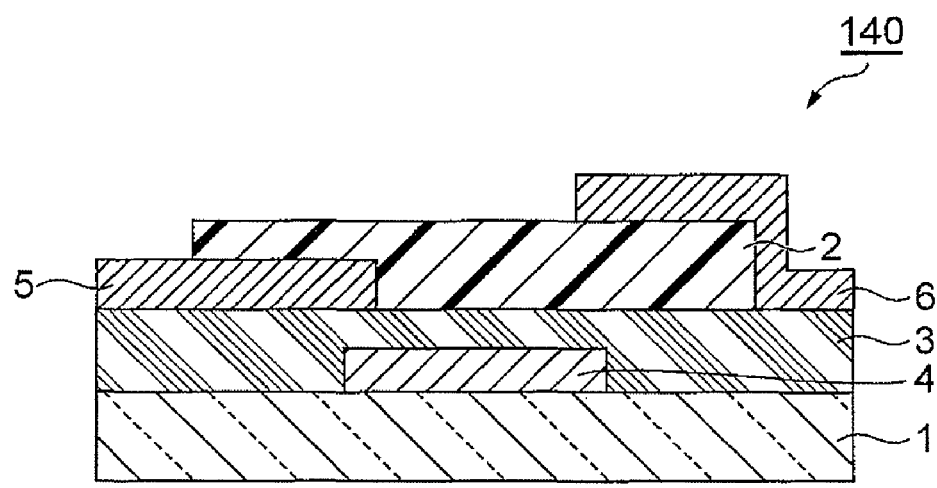
FIG. 5 is a schematic cross-sectional view of an organic thin-film transistor according to a fifth embodiment.

FIG. 5 is a schematic cross-sectional view of an organic thin-film transistor (field-effect type organic thin-film transistor) according to a fifth embodiment. The organic thin-film transistor 140 shown in FIG. 5 comprises a substrate 1, a gate electrode 4 formed on the substrate 1, an insulating layer 3 formed on the substrate 1 covering the gate electrode 4, a source electrode 5 formed on the insulating layer 3 covering a portion of the region of the insulating layer 3 under which the gate electrode 4 is formed, an active layer 2 foamed on the insulating layer 3 covering a portion of the source electrode 5, and a drain electrode 6 formed on the insulating layer 3 at a prescribed spacing from the source electrode 5 and covering a portion of the region of the active layer 2 under which the gate electrode 4 is formed.

Figure 6:
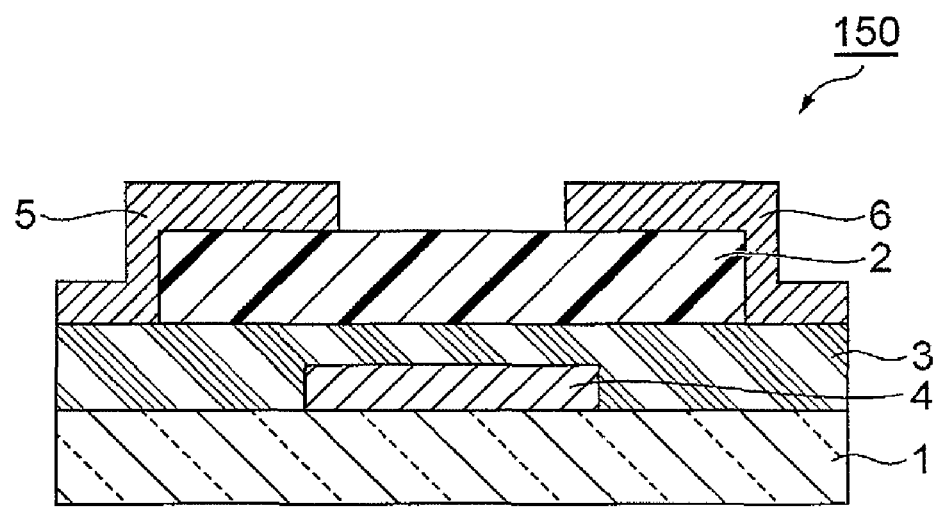
FIG. 6 is a schematic cross-sectional view of an organic thin-film transistor according to a sixth embodiment.

FIG. 6 is a schematic cross-sectional view of an organic thin-film transistor (field-effect type organic thin-film transistor) according to a sixth embodiment. The organic thin-film transistor 150 shown in FIG. 6 comprises a substrate 1, a gate electrode 4 formed on the substrate 1, an insulating layer 3 formed on the substrate 1 covering the gate electrode 4, an active layer 2 formed covering the region of the insulating layer 3 under which the gate electrode 4 is formed, a source electrode 5 formed on the insulating layer 3 covering a portion of the region of the active layer 2 under which the gate electrode 4 is formed, and a drain electrode 6 formed on the insulating layer 3 at a prescribed spacing from the source electrode 5 and covering a portion of the region of the active layer 2 under which the gate electrode 4 is formed.

Figure 7:
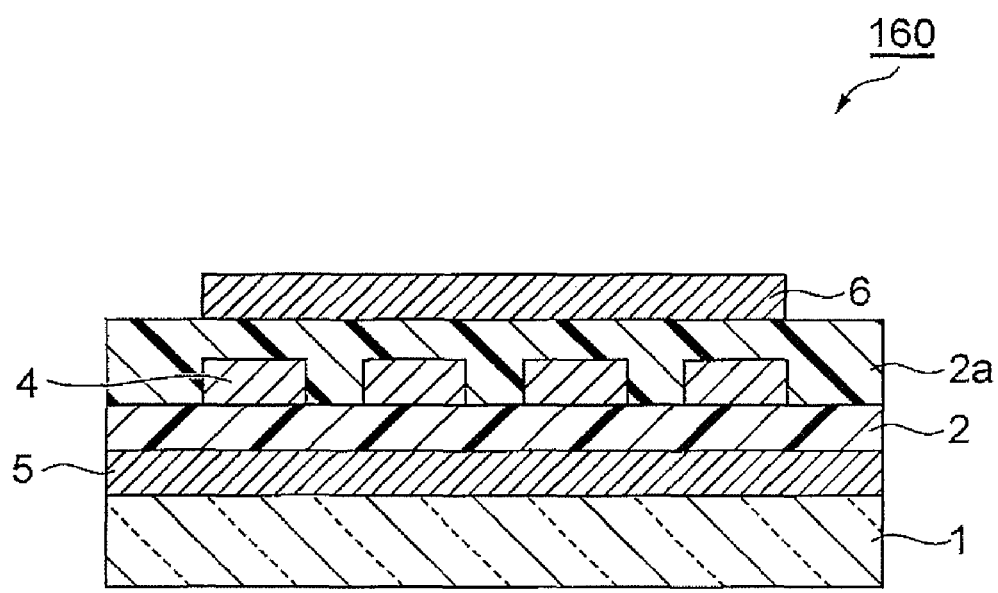
FIG. 7 is a schematic cross-sectional view of an organic thin-film transistor according to a seventh embodiment.

FIG. 7 is a schematic cross-sectional view of an organic thin-film transistor (static induction type organic thin-film transistor) according to a seventh embodiment. The organic thin-film transistor 160 shown in FIG. 7 comprises a substrate 1, a source electrode 5 formed on the substrate 1, an active layer 2 formed on the source electrode 5, a plurality of gate electrodes 4 formed at prescribed spacings on the active layer 2, an active layer 2a formed on the active layer 2 covering all of the gate electrodes 4 (the material composing the active layer 2a may be the same as or different from that of the active layer 2), and a drain electrode 6 formed on the active layer 2a.

In the organic thin-film transistors of the first to seventh embodiments, the active layer 2 and/or the active layer 2a contains a conjugated compound according to the present invention and forms a current channel between the source electrode 5 and drain electrode 6. The gate electrode 4 controls the level of current flowing through the current channel of the active layer 2 and/or active layer 2a by application of voltage.

This field-effect type organic thin-film transistor can be manufactured by a publicly known process, such as the process described in Japanese Unexamined Patent Publication HEI No. 5-110069, for example. A static induction type organic thin-film transistor can also be manufactured by a publicly known process such as the process described in Japanese Unexamined Patent Publication No. 2004-006476, for example.

The material of the substrate 1 is not particularly restricted so long as it does not inhibit the characteristics of the organic thin-film transistor. The substrate 1 used may be a glass panel, flexible film substrate or plastic panel.

Since organic solvent-soluble conjugated compounds are highly advantageous and preferred in forming the active layer 2, by the organic thin-film production method of the present invention described above, organic thin films composed of the active layer 2 can be formed.

The insulating layer 3 in contact with the active layer 2 is not particularly restricted so long as it is a material with high electrical insulating properties, and any publicly known one may be used. Examples include SiOx, SiNx, $Ta_2O_5$, polyimide, polyvinyl alcohol, polyvinylphenol, organic glass and photoresists. From the viewpoint of low voltage, it is preferred to use a material with high permittivity for the insulating layer 3.

When the active layer 2 is formed on the insulating layer 3, it may be formed after surface modification by treatment of the surface of the insulating layer 3 with a surface treatment agent such as a silane coupling agent in order to improve the interfacial properties between the insulating layer 3 and active layer 2. Examples of surface treatment agents include long-chain alkylchlorosilanes, long-chain alkylalkoxysilanes, fluorinated alkylchlorosilanes, fluorinated alkylalkoxysilanes and silylamine compounds such as hexamethyldisilazane. Before treatment with the surface treatment agent, the insulating layer surface may be pre-treated by ozone UV or $O_2$ plasma.

After the organic thin-film transistor has been fabricated, in order to protect the device it is preferable that a protecting film is formed on the organic thin-film transistor. This will help prevent reduction in the characteristics of the organic thin-film transistor due to shielding from air. A protecting film can also minimize adverse effects from the step of forming an operating display device on the organic thin-film transistor.

Examples of the method of forming the protecting film include covering with a UV curing resin, thermosetting resin, inorganic SiONx film or the like. For effective shielding from air, the steps after fabrication of the organic thin-film transistor and before formation of the protecting film are preferably carried out without exposure to air (for example, in a dry nitrogen atmosphere or in a vacuum).

Figure 8:
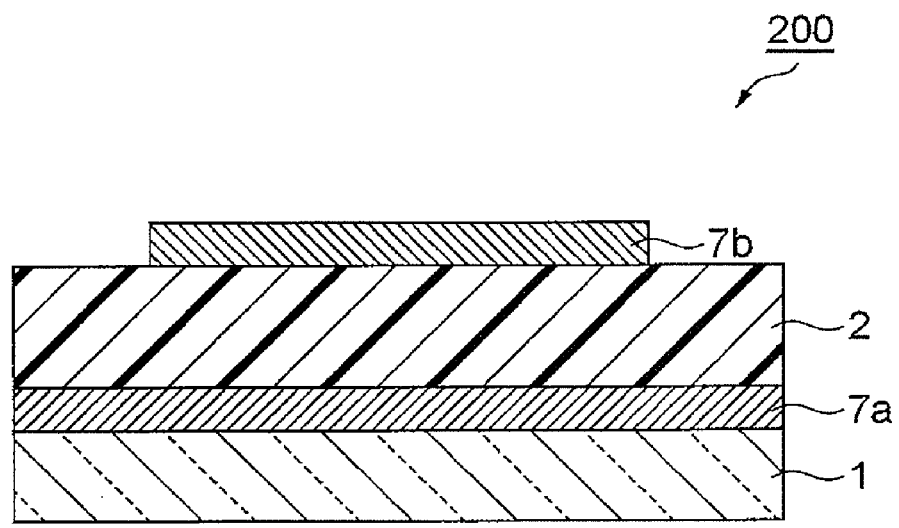
FIG. 8 is a schematic cross-sectional view of a solar cell according to an embodiment.

Application of an organic thin film of the present invention in a photoelectric conversion device will now be explained. A solar cell or optical sensor is typical photoelectric conversion device. FIG. 8 is a schematic cross-sectional view of a solar cell according to an embodiment. The solar cell 200 shown in FIG. 8 comprises a substrate 1, a first electrode 7a formed on the substrate 1, an active layer 2 made of an organic thin film that contains a conjugated compound of the present invention formed on the first electrode 7a, and a second electrode 7b formed on the active layer 2.

In this solar cell 200, a transparent or semi-transparent electrode is used for either the first electrode 7a or the second electrode 7b. As electrode materials there may be used metals such as aluminum, gold, silver, copper, alkali metal and alkaline earth metals or their semi-transparent films, or transparent conductive films. In order to obtain high open voltage, it is preferred to select the electrodes so as to produce a large work function difference. Charge generators, sensitizing agents and the like may also be added in order to increase photosensitivity in the active layer 2 (organic thin film). The substrate 1 may be a silicon substrate, glass panel, plastic panel or the like.

Figure 9:
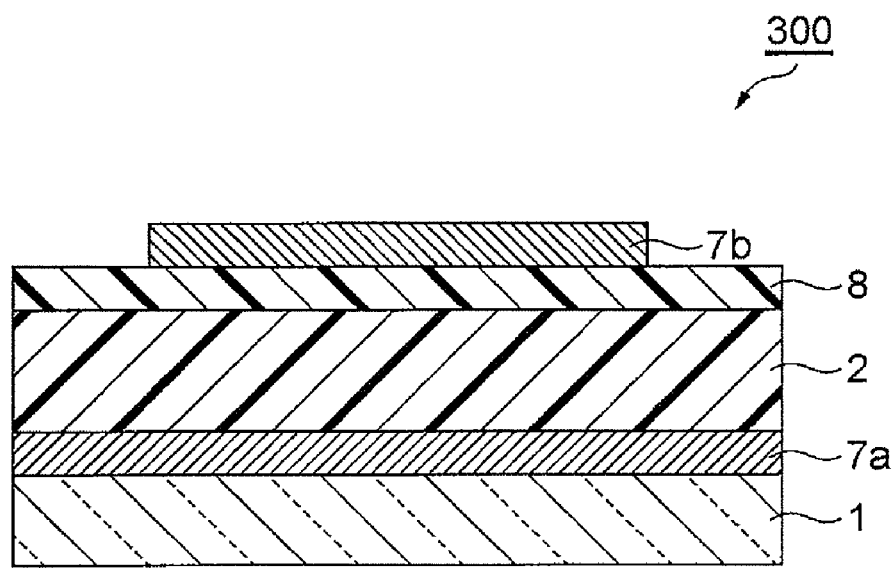
FIG. 9 is a schematic cross-sectional view of an optical sensor according to a first embodiment.

FIG. 9 is a schematic cross-sectional view of an optical sensor according to a first embodiment. The optical sensor 300 shown in FIG. 9 comprises a substrate 1, a first electrode 7a formed on the substrate 1, an active layer 2 made of an organic thin film comprising a conjugated compound of the present invention, formed on the first electrode 7a, a charge generation layer 8 formed on the active layer 2, and a second electrode 7b formed on the charge generation layer 8.

Figure 10:
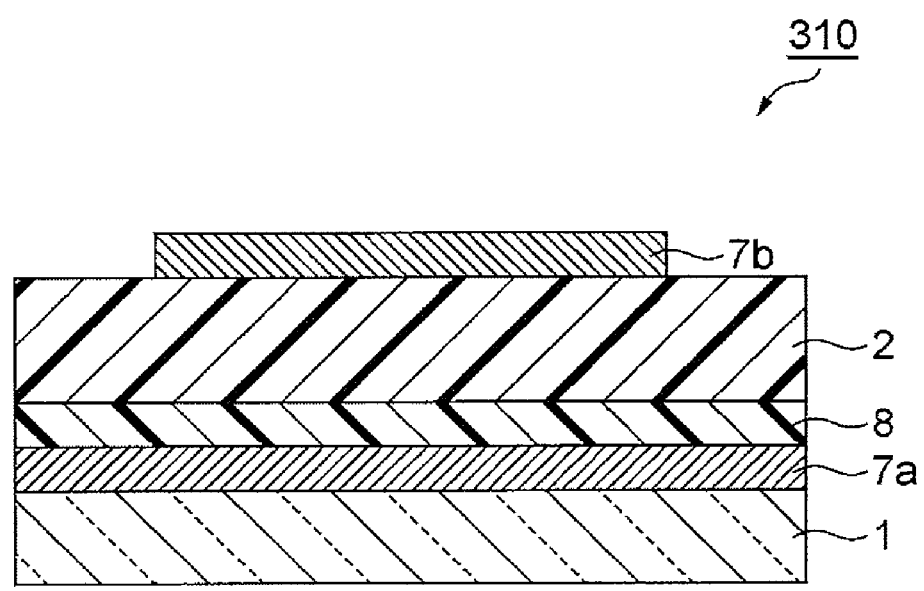
FIG. 10 is a schematic cross-sectional view of an optical sensor according to a second embodiment.

FIG. 10 is a schematic cross-sectional view of an optical sensor according to a second embodiment. The optical sensor 310 shown in FIG. 10 comprises a substrate 1, a first electrode 7a formed on the substrate 1, a charge generation layer 8 formed on the first electrode 7a, an active layer 2 made of an organic thin film comprising a conjugated compound of the present invention, formed on the charge generation layer 8, and a second electrode 7b formed on the active layer 2.

Figure 11:
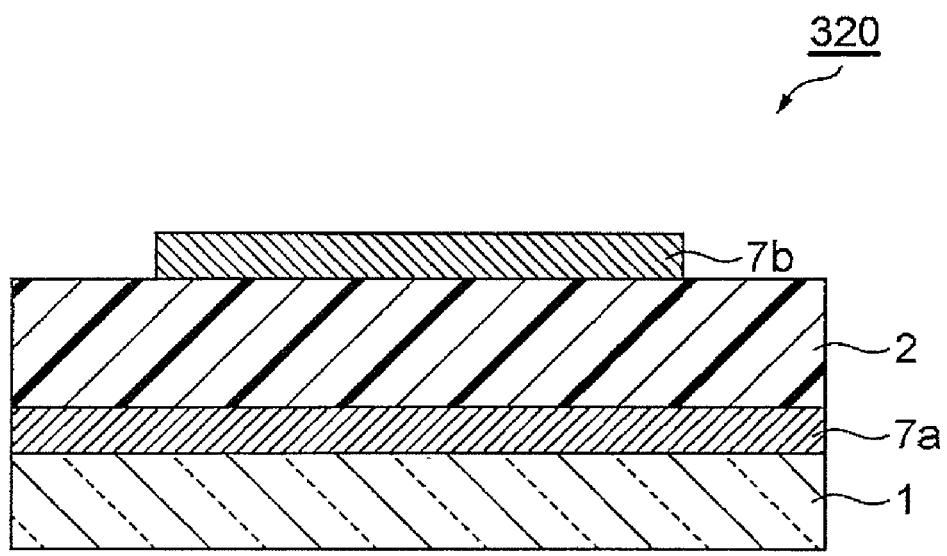
FIG. 11 is a schematic cross-sectional view of an optical sensor according to a third embodiment.

FIG. 11 is a schematic cross-sectional view of an optical sensor according to a third embodiment. The optical sensor 320 shown in FIG. 11 comprises a substrate 1, a first electrode 7a formed on the substrate 1, an active layer 2 made of an organic thin film that comprises a conjugated compound of the present invention, formed on the first electrode 7a, and a second electrode 7b formed on the active layer 2.

In the optical sensors of the first to third embodiments, a transparent or semi-transparent electrode is used for either or both the first electrode 7a or the second electrode 7b. The charge generation layer 8 is a layer that generates an electrical charge upon absorption of light. As electrode materials there may be used metals such as aluminum, gold, silver, copper, alkali metal and alkaline earth metals or their semi-transparent films, or transparent conductive films. Carrier generators, sensitizing agents and the like may also be added in order to increase photosensitivity in the active layer 2 (organic thin film). The substrate 1 may be a silicon substrate, glass panel, plastic panel or the like.

The present invention was explained above in detail based on embodiments thereof. However, the present invention is not limited to these described embodiments. The present invention may also be applied in a variety of modifications so long as the gist thereof is maintained.

The second invention group will now be explained in detail.

The nitrogen-containing fused-ring compound of the present invention has a structure represented by the above formula (α-I).

In the above formula (α-I), $R^{21}$ and $R^{22}$ each independently represent a hydrogen atom, a halogen atom or an optionally substituted monovalent group, and $Z^{21}$ and $Z^{22}$ each independently represent any one of the groups represented by the above formulas (α-i)-(α-ix). Also, $R^{23}$, $R^{24}$, $R^{25}$ and $R^{26}$ each independently represent a hydrogen atom, a halogen atom or a monovalent group, and $R^{23}$ and $R^{24}$ may bond together to form a ring. The left side and the right side of the group represented by the above formula (α-viii) may be interchanged. From the viewpoint of facilitating production, $Z^{21}$ and $Z^{22}$ preferably have the same structure.

The nitrogen-containing fused-ring compound of the present invention represented by the above formula (α-I) is preferably a compound represented by the following formula (α-I-I).

[Chemical Formula 39]

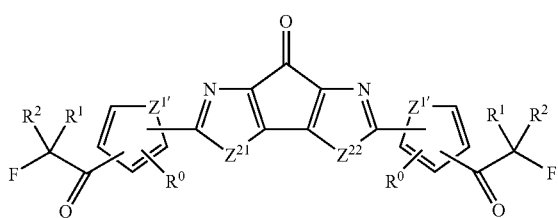

(α-I-I)

In the above formula (α-I-I), $Z^{21}$, $Z^{22}$ and $Z^{1'}$ each independently represents any one of the groups represented by the above formulas (α-i)-(α-ix). Also, $R^1$ and $R^2$ have the same definitions as $R^1$ and $R^2$ in formula (I), and each independently represent a hydrogen atom, a halogen atom or a monovalent group. Specific examples of halogen atoms and monovalent groups include the same ones as for $R^1$ and $R^2$ in the above formula (I). Also, $R^0$ has the same definition as $R^0$ in the above formula (III), and it represents a hydrogen atom, a C1 to C20 alkyl group or a C1 to C20 alkoxy group. A plurality the groups in $R^0$ may be the same or different. Specific examples of a C1 to C20 alkyl group and a C1 to C20 alkoxy group there may be mentioned the same ones as for $R^0$ in the above formula (III).

In the nitrogen-containing fused-ring compound of the present invention, it is preferable that at least one of $R^{21}$ and $R^{22}$ in the above formula (α-I) is a group represented by the following formula (IV), and more preferable that both $R^{21}$ and $R^{22}$ are groups represented by the following formula (IV).

[Chemical Formula 40]

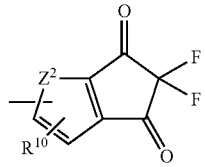

(IV)

The group represented by the above formula (IV) is a group with the same definition as the group represented by the above formula (IV) explained above for the first invention group, where $R^{10}$ represents a hydrogen atom, a fluorine atom, a C1 to C20 alkyl group, a C1 to C20 fluoroalkyl group, a C1 to C20 alkoxy group or a C1 to C20 fluoroalkoxy group, $Z^2$ represents a group represented by any one of the following formulas (xi)-(xix), $R^{13}$, $R^{14}$, $R^{15}$ and $R^{16}$ each independently represent a hydrogen atom, a halogen atom or a monovalent group, and $R^{13}$ and $R^{14}$ may bond together to form a ring. Specific examples of a C1-20 alkyl, a C1 to C20 fluoroalkyl group, a C1 to C20 alkoxy group and a C1 to C20 fluoroalkoxy group include the same one mentioned above for the first invention group.

[Chemical Formula 41]

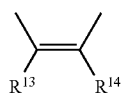

(xi)

(xii)

(xiii)

(xiv)

(xv)

(xvi)

(xvii)

(xviii)

-continued

 (xix)

The nitrogen-containing fused-ring polymer of the present invention has a repeating unit represented by the above formula (α-II). That is, a nitrogen-containing fused-ring polymer of the present invention has at least one and preferably 2 or more repeating units represented by the above formula (α-II), and may additionally have another repeating unit.

In the above formula (α-II), $Z^{21}$ and $Z^{22}$ each independently represent any one of the group represented by the above formulas (α-i)-(α-ix). $R^{23}$, $R^{24}$, $R^{25}$ and $R^{26}$ each independently represent a hydrogen atom, a halogen atom or a monovalent group, and $R^{23}$ and $R^{24}$ may bond together to form a ring. The left side and the right side of the group represented by the above formula (α-viii) may be interchanged. By having such a repeating unit, the compound can be used as an organic n-type semiconductor with a particularly excellent electron transport property.

It is preferable that the nitrogen-containing fused-ring polymer of the present invention preferably has at least one repeating unit represented by the above formula (α-II) and at least one repeating unit represented by the following formula (α-III) which is different from the repeating unit represented by the above formula (α-II). It is more preferable that it has at least one repeating unit represented by the above formula (α-II) and at least one repeating unit represented by the following formula (α-IV). Such a structure will widen the range of variability for the soluble, mechanical, thermal and electronic characteristics. In the following formula (α-III), $Ar^{21}$ represents a divalent aromatic hydrocarbon or a divalent heterocyclic group, wherein the groups may be optionally substituted. The ratio of the repeating unit represented by formula (α-II) and the repeating unit represented by formula (α-III) (preferably the repeating unit represented by the following formula (α-IV)) is preferably 10-1000 mol of the latter to 100 mol of the former, more preferably 25-400 mol of the latter to 100 mol of the former and even more preferably 50-200 mol of the latter to 100 mol of the former.

[Chemical Formula 42]

 (α-III)

In this case, $Ar^{21}$ is preferably a repeating unit represented by the following formula (α-IV). In the formula, $Z^{23}$ is the same as or different from $Z^{21}$ or $Z^{22}$, and is any one of the groups represented by the above formulas (α-i)-(α-ix). Also, $R^{27}$ and $R^{28}$ each independently represents a hydrogen atom, a halogen atom or a monovalent group, and $R^{27}$ and $R^{28}$ may bond together to form a ring. $R^{23}$, $R^{24}$, $R^{25}$ and $R^{26}$ have the same definitions as above.

[Chemical Formula 43]

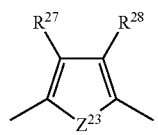 (α-IV)

The divalent aromatic hydrocarbon group represented by $Ar^{21}$ is an atomic group remaining after removing two hydrogen atoms from a benzene ring or fused ring, and they will generally have 6-60 and preferably 6-20 carbon atoms. Examples of fused rings include naphthalene, anthracene, tetracene, pentacene, pyrene, perylene and fluorene rings. As divalent aromatic hydrocarbon groups there are preferred atomic groups remaining after removing two hydrogens from a benzene ring, pentacene ring, pyrene ring or fluorene ring. The divalent aromatic hydrocarbon groups may be optionally substituted. The numbers of carbon atoms of the substituents are not included in the number of carbon atoms in the divalent aromatic hydrocarbon groups. As substituents there may be mentioned halogen atoms and saturated or unsaturated hydrocarbon, aryl, alkoxy, aryloxy, monovalent heterocyclic, amino, nitro and cyano groups.

The divalent heterocyclic group represented by $Ar^{21}$ is an atomic group remaining after removing two hydrogen atoms from a heterocyclic compound, and the number of carbon atoms will normally be 3-60 and preferably 3-20. Examples of divalent heterocyclic groups include atomic groups remaining after removing two hydrogen atoms from thiophene, thienothiophene, dithienothiophene, thiazole, pyrrole, pyridine or pyrimidine, and preferred are atomic groups remaining after removing two hydrogens from thiophene, thienothiophene or thiazole. The divalent heterocyclic group may have substituents, and the numbers of carbons of the substituents are not included in the number of carbons in the divalent heterocyclic group. As substituents there may be mentioned halogen atoms and saturated or unsaturated hydrocarbon groups, aryl groups, alkoxy groups, aryloxy groups, monovalent heterocyclic groups, amino groups, nitro groups and cyano groups.

A heterocyclic compound referred to here is an organic compound with a ring structure, the elements composing the ring of which include not only carbon but also heteroatoms such as oxygen, sulfur, nitrogen, phosphorus, boron and silicon.

Examples of $Z^{21}$ and $Z^{22}$ in formula (α-I) are preferably include groups represented by the above formulas (α-i), (α-ii), (α-iii), (α-vii), (α-viii) and (α-ix), preferably groups represented by formulas the (α-ii) and (α-vii), and most preferably groups represented by formula the (α-ii). $Z^{23}$ in formula (α-IV) is preferably, for example, a group represented by formula the above (α-i), (α-ii), (α-iii), (α-vii), (α-viii) or (α-ix), preferably a group represented by formula (α-ii), (α-iii), (α-vii) or (α-ix), and most preferably a group represented by formula (α-ii). Thiazole rings, oxazole rings and imidazole rings, and especially thiazole rings, have a characteristic electrical nature and exhibit various electrical properties.

In formulas (α-vii), (α-viii) and (α-ix), and formulas (α-I), (α-II) and (α-IV), $R^{21}$-$R^{28}$ each independently represent a hydrogen atom, a halogen atom or a monovalent group, and a ring may be formed between $R^{23}$ and $R^{24}$ and between $R^{27}$ and $R^{28}$.

It is preferable that monovalent groups represented by $R^{21}$-$R^{28}$ are straight-chain or branched low molecular chains, monovalent cyclic groups, wherein the cyclic groups may have monocycles or fused rings, hydrocarbon rings or heterocyclic rings, saturated or unsaturated, and with or without substituents. A monovalent group may be an electron-donating group or electron-withdrawing group.

It is more preferable that monovalent groups represented by $R^{21}$-$R^{28}$ are straight-chain or branched low molecular chains (C1 to C20 groups), monovalent cyclic groups with 3-60 annular atoms, wherein cyclic groups may have monocycles or fused rings, hydrocarbon rings or heterocyclic rings, saturated or unsaturated, and with or without substituents, saturated or unsaturated hydrocarbon groups, hydroxyl groups, alkoxy groups, alkanoyloxy groups, amino groups, oxyamino groups, alkylamino groups, dialkylamino groups, alkanoylamino groups, cyano groups, nitro groups, sulfo groups, alkyl groups optionally substituted with one or more halogen atoms, alkoxysulfonyl groups, wherein some or all of the hydrogen atoms in the alkoxy groups may be optionally substituted with one or more halogen atoms, alkylsulfonyl groups, wherein some or all of the hydrogen atoms in the alkyl groups may be optionally substituted with one or more halogen atoms, sulfamoyl groups, alkylsulfamoyl groups, carboxyl groups, carbamoyl groups, alkylcarbamoyl groups, alkanoyl groups, wherein some or all of the hydrogen atoms in the alkanoyl groups may be optionally substituted with one or more halogen atoms, and alkoxycarbonyl groups. Examples of monovalent cyclic groups with 3-60 annular atoms include groups represented by the following formulas.

[Chemical Formula 44]

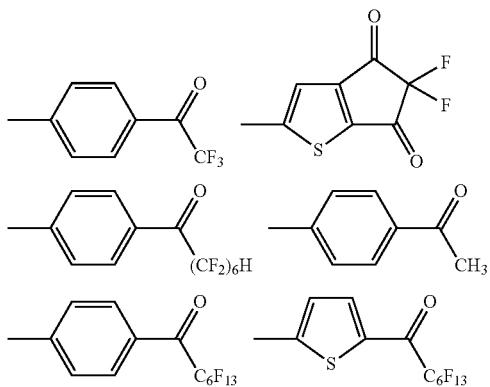

As halogen atoms for the purpose of the present specification there may be mentioned a fluorine atom, a chlorine atom, a bromine atom and an iodine atom.

Examples of alkyl groups include methyl, ethyl, n-propyl, isopropyl, n-butyl, isobutyl, sec-butyl and tert-butyl, and this also applies for groups containing alkyl groups in their structures (such as alkoxy, alkylamino group and alkoxycarbonyl). It is preferable that alkyl groups are C1 to C12 alkyl groups, and more preferable that they are C1 to C10 alkyl groups.

Examples of unsaturated hydrocarbon groups there may be mentioned vinyl groups, 1-propenyl groups, allyl groups, propargyl groups, isopropenyl groups, 1-butenyl groups and 2-butenyl groups. Vinyl group is a preferred unsaturated hydrocarbon group.

Examples of alkanoyl groups include formyl groups, acetyl groups, propionyl groups, isobutyryl groups, valeryl groups and isovaleryl groups, and this also applies for groups containing alkanoyl groups in their structures (such as alkanoyloxy and alkanoylamino). A "C1 alkanoyl group" is formyl, which also applies for groups containing alkanoyl groups in their structures. As preferred alkanoyl groups there may be mentioned formyl and acetyl.

$R^{23}$ and $R^{24}$ in formula ($\alpha$-vii) mentioned for formulas ($\alpha$-I), ($\alpha$-II) and ($\alpha$-IV) are preferably hydrogen atoms, fluorine atoms, alkyl groups or alkoxy groups, and more preferably each is hydrogen atom or fluorine atom.

Either or both $R^{21}$ and $R^{22}$ in the above formula ($\alpha$-I) preferably have one or more hydrogen atoms in the substituent-containing groups replaced with fluorine atoms, and preferably either or both have a carbonyl structure. More preferably, $R^{21}$ and $R^{22}$ have carbonyl structures and have a group with one or more hydrogen atoms replaced with fluorine atoms. Such a group will lower the LUMO level and improve the solubility in organic solvents. From the viewpoint of increasing the electron transport property, more preferably either or both $R^{21}$ and $R^{22}$ groups having fluoroalkyl, fluoroalkoxy, fluoroaryl or $\alpha$-fluoroketone structures, fluoroalkyl-substituted aryl groups, fluoroalkoxy-substituted aryl groups, aryl groups substituted with groups having $\alpha$-fluoroketone structures, fluoroalkyl-substituted monovalent heterocyclic groups, fluoroalkoxy-substituted monovalent heterocyclic groups or monovalent heterocyclic groups substituted with groups having $\alpha$-fluoroketone structures, and most preferably both $R^{21}$ and $R^{22}$ are groups having fluoroalkyl, fluoroalkoxy, fluoroaryl or $\alpha$-fluoroketone structures, fluoroalkyl-substituted aryl groups, fluoroalkoxy-substituted aryl groups, aryl groups substituted with groups having $\alpha$-fluoroketone structures, fluoroalkyl-substituted monovalent heterocyclic groups, fluoroalkoxy-substituted monovalent heterocyclic groups or monovalent heterocyclic groups substituted with groups having $\alpha$-fluoroketone structures.

It is sufficient if the nitrogen-containing fused-ring polymer of the present invention has a repeating unit represented by the above formula ($\alpha$-II), and it may have two or more repeating units represented by formula ($\alpha$-II). In addition to the repeating unit represented by formula ($\alpha$-II) it may also have a unit represented by the above formula ($\alpha$-III), or two or more units represented by formula ($\alpha$-III).

It is preferable that the nitrogen-containing fused-ring polymer of the present invention has a structure wherein a repeating unit represented by the above formula ($\alpha$-II) and a repeating unit represented by the above formula ($\alpha$-III) (preferably a repeating unit represented by the above formula ($\alpha$-IV)) are adjacent. When a repeating unit represented by the above formula ($\alpha$-II) is adjacent to a repeating unit represented by the above formula ($\alpha$-III) (preferably a repeating unit represented by the above formula ($\alpha$-IV)), because it is possible to reduce the torsional angle between the adjacent aromatic rings or heterocyclic rings, thus improving the intramolecular twist, widening the intramolecular $\pi$ conjugation and lowering the LUMO level, it is possible to enhance the electron transport property as a result. The "torsional angle" mentioned here is defined as the angle between 0 and 90 degrees among the angles formed by the plane containing the heterocyclic ring in the repeating unit represented by formula ($\alpha$-II), and the plane containing the adjacently bonded aromatic ring or heterocyclic ring. When a repeating unit represented by the above formula ($\alpha$-II) is adjacent to a repeating unit represented by the above formula ($\alpha$-III) (preferably a repeating unit represented by the above formula ($\alpha$-IV)), the torsional angle will usually be 0-45 degrees, typically 0-40 degrees and more typically 0-30 degrees.

Figure 12:
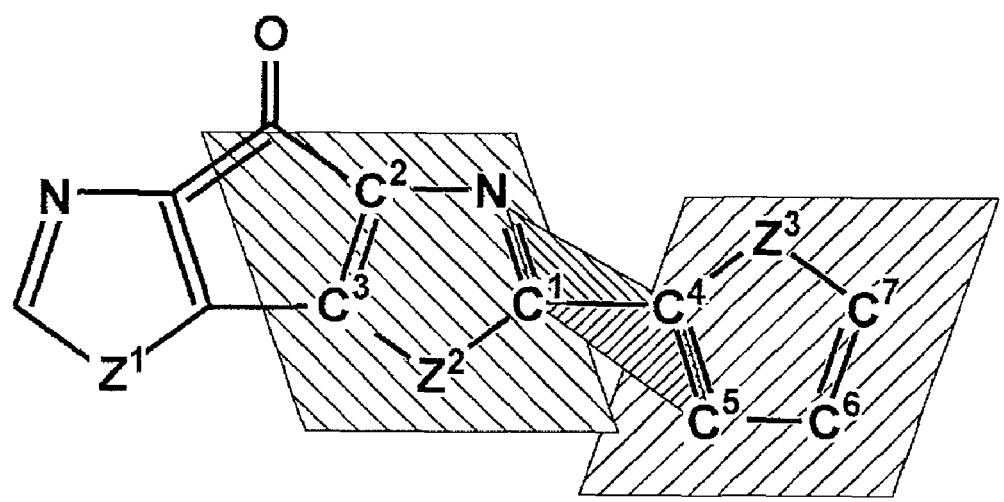
FIG. 12 is a drawing showing the torsional angle formed between the ring of the repeating unit represented by formula (α-II) and the ring of the repeating unit represented by formula (α-IV).

FIG. 12 is a drawing showing the torsional angle formed between the ring of a repeating unit represented by formula ($\alpha$-II) and the ring of a repeating unit represented by formula ($\alpha$-IV). The torsional angle in FIG. 12 is the angle formed between the plane of N—$C^1$—$C^4$ and the plane of $C^1$—$C^4$—$C^5$.

The nitrogen-containing fused-ring polymer of the present invention is preferably represented by the following formula (α-V) or (α-VI) from the viewpoint of increasing the electron transport property.

[Chemical Formula 45]

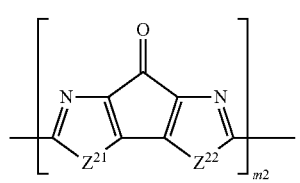

(α-V)

[Chemical Formula 46]

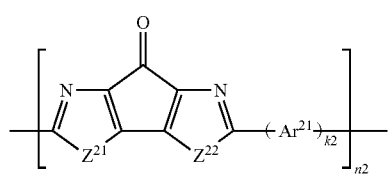

(α-VI)

Here, $Z^{21}$, $Z^{22}$ and $Ar^{21}$ have the same definitions as above. When a plurality of the groups in $Z^{21}$, $Z^{22}$ and $Ar^{21}$ are present, they may be the same or different. The symbol k2 represents an integer of 1-10, preferably 1-6 and even more preferably 1-3. The symbol m2 represents an integer of 2-500, preferably 2-100 and even more preferably 3-20. The symbol n2 represents an integer of 1-500, preferably 1-100 and even more preferably 2-20. Particularly preferred among these are compounds wherein $Z^{21}$ and $Z^{22}$ are all of formula (α-ii).

When the end groups of the nitrogen-containing fused-ring polymer has polymerizing active groups, these may be used as precursors for the nitrogen-containing fused-ring polymer. In this case, the nitrogen-containing fused-ring polymer preferably has at least two polymerizing active groups in the molecule. Examples of polymerizing active groups include halogen atoms, and alkyl sulfonate, aryl sulfonate, arylalkyl sulfonate, alkylstannyl, arylstannyl, arylalkylstannyl, boric acid ester residue, sulfoniummethyl, phosphoniummethyl, phosphonatemethyl, monohalogenated methyl, boric acid residue ($-B(OH)_2$), formyl and vinyl groups, among which halogen atoms, alkylstannyl groups and boric acid ester residue groups are preferred. Examples of boric acid ester residues include groups represented by the following formula.

[Chemical Formula 47]

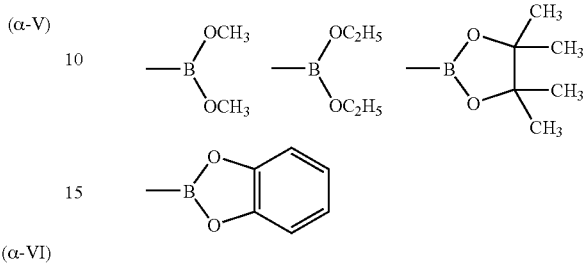

When a nitrogen-containing fused-ring polymer of the present invention is to be used as an organic thin film and polymerizing active groups remain at the ends, they are preferably protected with stable groups to avoid potential reduction in the characteristics and durability of devices formed therefrom.

As end groups there may be mentioned hydrogen atoms, fluorine atoms, alkyl groups, alkoxy groups, acyl groups, aminoketo groups, aryl groups, heterocyclic groups, wherein some or all of the hydrogen atoms bonded to the groups are optionally replaced with fluorine), groups with α-fluoroketone structures and electron-donating or electron-withdrawing groups, and from the viewpoint of increasing the electron transport property there are preferred fluoroalkyl groups, fluoroalkoxy groups, fluoroaryl groups, groups with α-fluoroketone structures and electron-withdrawing groups, and there are more preferred groups wherein all of the hydrogen atoms are replaced with fluorine atoms, such as perfluoroalkyl groups, perfluoroalkoxy groups or perfluorophenyl groups. It is preferable that they have conjugated bonds that are continuous with the conjugated structure of the main chain, and Example of the structure may include the structure bonding with aryl or heterocyclic groups via carbon-carbon bonds.

Examples of most preferred among the nitrogen-containing fused-ring polymers of the present invention are represented by the following formulas (α-1)-(α-5), for example.

[Chemical Formula 48]

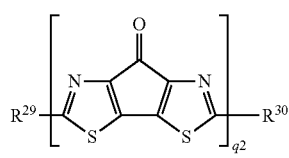

(α-1)

[Chemical Formula 49]

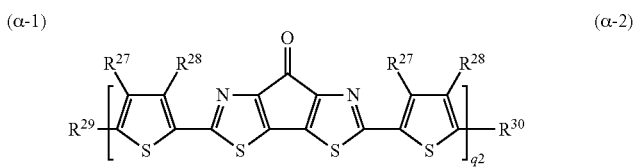

(α-2)

[Chemical Formula 50]

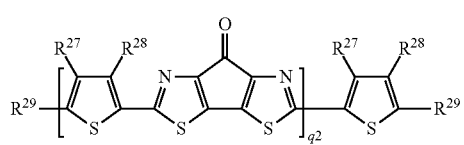

(α-3)

[Chemical Formula 51]

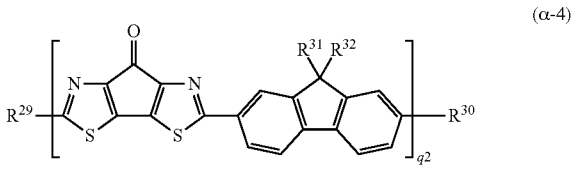

(α-4)

[Chemical Formula 52]

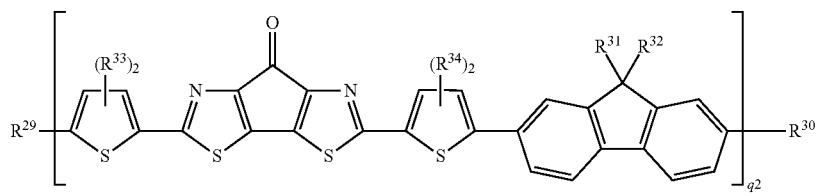

(α-5)

Here, $R^{29}$ and $R^{30}$ represent end groups, which may be the same or different, examples of which include the end groups mentioned above, preferably fluoroalkyl groups and groups with α-fluoroketone structures and more preferably perfluoroalkyl groups and groups with α-fluoroketone structures. $R^{31}$, $R^{32}$, $R^{33}$ and $R^{34}$ each independently represent a hydrogen atom or an arbitrary substituent, being preferably alkyl group, alkoxy group or aryl group and more preferably alkyl group. A plurality of the groups in $R^{31}$, $R^{32}$, $R^{33}$ and $R^{34}$ in the nitrogen-containing fused-ring polymer may be the same or different. In order to facilitate production, a plurality of the groups in $R^{31}$, $R^{32}$, $R^{33}$ and $R^{34}$ groups are preferably the same. The group for q2 may be appropriately selected according to the method for forming the organic thin film using the nitrogen-containing fused-ring polymer. If the nitrogen-containing fused-ring polymer has sublimating property, a vapor growth process such as vacuum vapor deposition may be used to form the organic thin film, in which case q2 is an integer of preferably 1-10, more preferably 2-10 and even more preferably 2-5. On the other hand, when the organic thin film is to be formed using a method of coating a solution of the nitrogen-containing fused-ring polymer dissolved in an organic solvent, q2 is an integer of preferably 3-500, more preferably 6-300 and even more preferably 20-200. When the film is formed by coating, from the viewpoint of homogeneity of the film, it is preferable that the number-average molecular weight of the nitrogen-containing fused-ring polymer based on polystyrene is between $1\times10^3$ and $1\times10^7$ and more preferable that it is between $1\times10^4$ and $1\times10^6$.

The following may be mentioned as specific examples of nitrogen-containing fused-ring compounds and nitrogen-containing fused-ring polymers of the present invention.

[Chemical Formula 53]

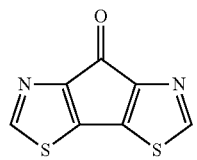

[Chemical Formula 54]

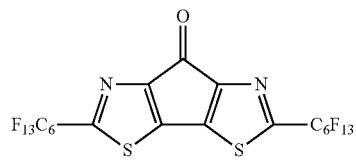

[Chemical Formula 55]

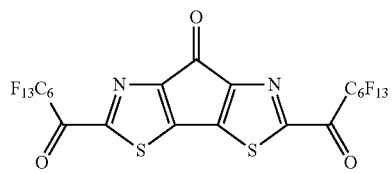

[Chemical Formula 56]

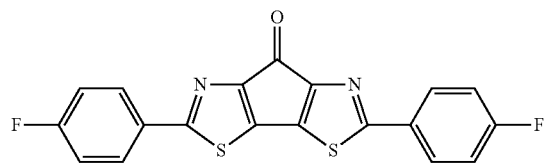

[Chemical Formula 57]

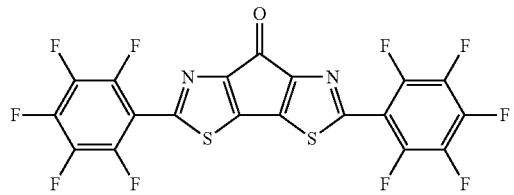

[Chemical Formula 58]

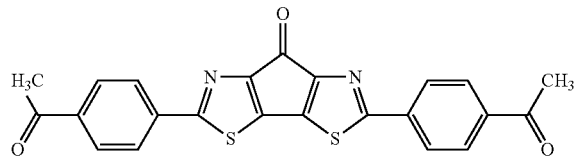

[Chemical Formula 59]

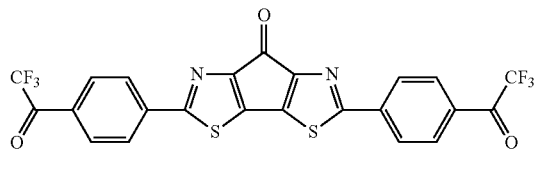

[Chemical Formula 60]

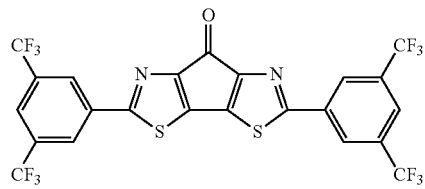

-continued
[Chemical Formula 61]
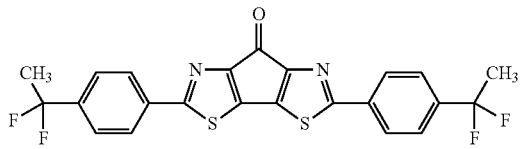
[Chemical Formula 62]
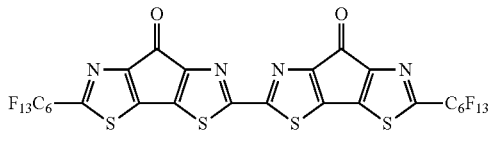
[Chemical Formula 63]
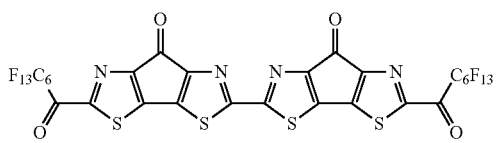
[Chemical Formula 64]
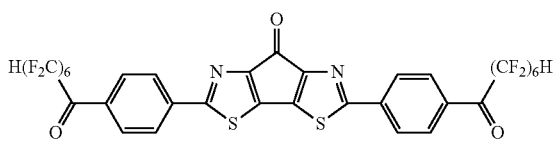
[Chemical Formula 65]
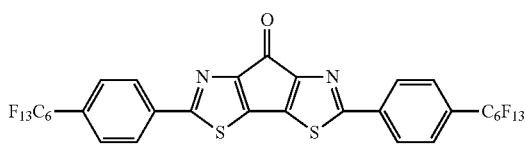
[Chemical Formula 66]
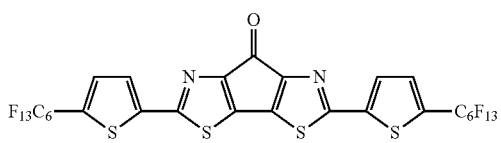
[Chemical Formula 67]
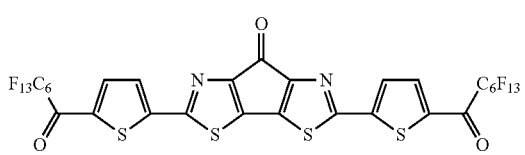
[Chemical Formula 68]
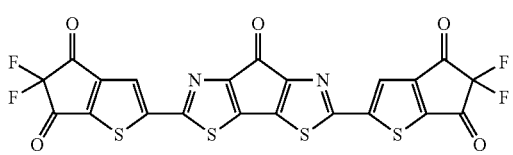
[Chemical Formula 69]
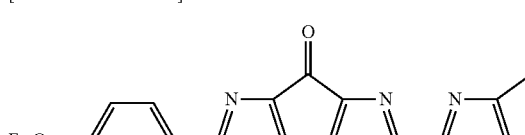
[Chemical Formula 70]
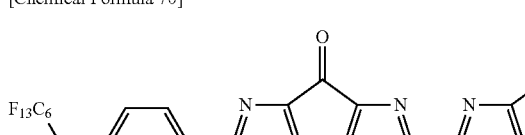
[Chemical Formula 71]
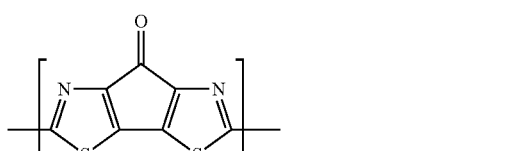
[Chemical Formula 72]
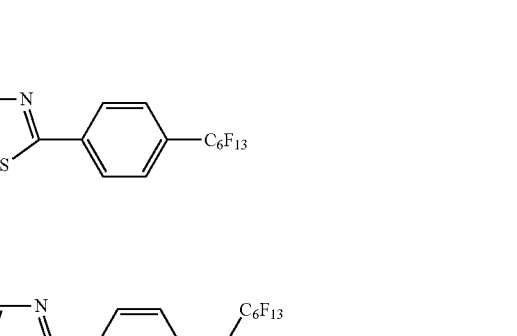
[Chemical Formula 73]
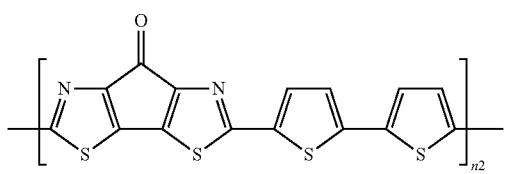

In the formulas, n2 represents the polymerization degree.

The nitrogen-containing fused-ring compounds or nitrogen-containing fused-ring polymers of the present invention may be produced by any method, but it is preferable that they are produced by the production method described below.

A method for producing a nitrogen-containing fused-ring compound of the present invention will be explained first. The nitrogen-containing fused-ring compound (α-d) represented by the above formula (α-I) can be produced by a process shown in the following scheme, for example, in which a precursor (α-b) is first produced using a starting material represented by the following formula (α-a) or (α-a') and then the precursor (α-b) is reacted with a carbonyl crosslinking agent. Different substituents can also be introduced by a production method including a step obtaining compound (α-f). The protecting group of the compound (α-j) may be removed afterward to obtain a carbonyl compound.

[Chemical Formula 74]

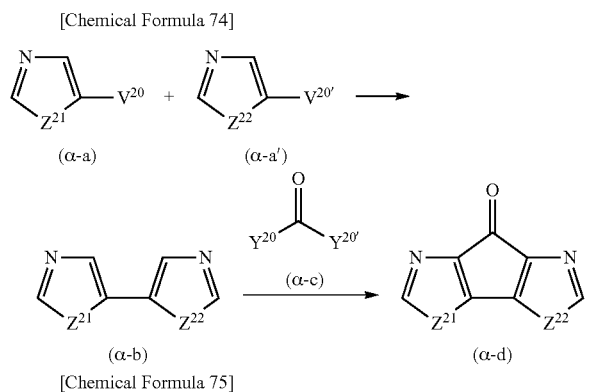

[Chemical Formula 75]

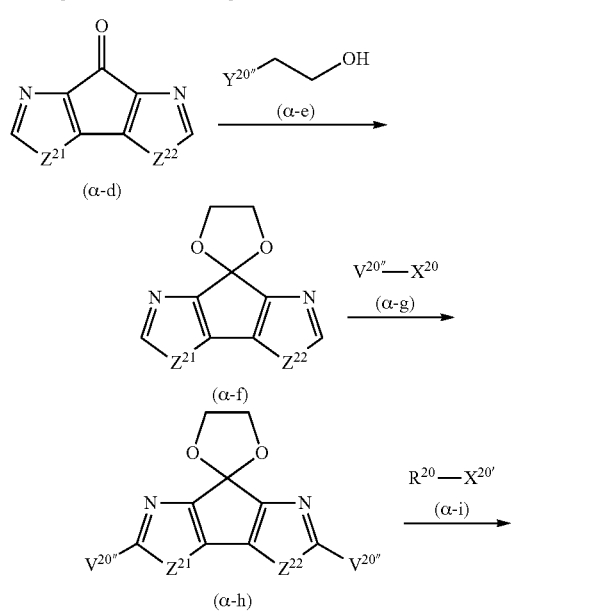

Here, $Z^{21}$ and $Z^{22}$ have the same definitions as above, $R^{20}$ has the same definition as $R^{21}$, and a plurality of the groups in $R^{20}$ may be the same or different. $V^{20}$, $V^{20'}$ and $V^{20''}$ represent reactive groups which may be the same or different, and specifically they represent halogen atoms, alkyl sulfonate groups, aryl sulfonate groups, arylalkyl sulfonate groups, alkylstannyl groups, arylstannyl groups, arylalkylstannyl groups, boric acid ester residue, sulfoniummethyl groups, phosphoniummethyl groups, phosphonatemethyl groups, monohalogenated methyl groups, boric acid residue, formyl or vinyl groups.

From the viewpoint of facilitating the synthesis reaction, preferably $V^{20}$, $V^{20'}$ and $V^{20''}$ each independently represents a halogen atom or an alkyl sulfonate group, aryl sulfonate group, arylalkyl sulfonate group, alkylstannyl group, boric acid ester residue or boric acid residue group.

$X^{20}$ and $X^{20'}$ represent halogen atoms and $Y^{20}$, $Y^{20'}$ and $Y^{20''}$ each independently represents leaving groups, examples of which include amino groups and alkoxy groups.

At the reaction process described above, in order to protect the highly reactive functional groups, if necessary, the process may further include a step of subsequently converting the highly reactive functional groups to inactive functional groups (protecting groups) to protect them if necessary, and a step of removing the protecting groups upon completion of the reaction. Protecting groups may be appropriately selected according to the functional groups to be protected and the reaction employed, and preferred examples include trimethylsilyl (TMS), triethylsilyl (TES), tert-butyldimethylsilyl (TBS or TBDMS), triisopropylsilyl (UPS) and tert-butyldiphenylsilyl (TBDPS) for protection of active hydrogens.

A solvent may also be appropriately used as necessary in the reaction step described above. It is most preferable that the solvent used is one that does not interfere with the desired reaction, and examples include aliphatic hydrocarbons such as hexane, aromatic hydrocarbons such as benzene and toluene, nitriles such as acetonitrile, ethers such as diethyl ether, tetrahydrofuran and 1,2-dimethoxyethane, and halogenated solvents such as dichloromethane, 1,2-dichloroethane and carbon tetrachloride. These may be used alone or in combinations of two or more. An example of a suitable solvent is dichloromethane.

When a nitrogen-containing fused-ring compound of the present invention is to be used as a material for an organic thin-film device, since the purity will affect the device characteristics, the produced compound is preferably subjected to purification treatment by a method such as distillation, sublimation purification or recrystallization.

The reaction conditions and reaction reagents for the production method may also be appropriately selected among others than those mentioned above. It is preferable that the nitrogen-containing fused-ring compounds of the present invention represented by the above formula (α-I) are produced by the production method of the present invention as mentioned above, but this is not limitative and they may be produced by other methods as well.

A method for producing a nitrogen-containing fused-ring polymer of the present invention will now be explained. Nitrogen-containing fused-ring polymers of the present invention can be produced using compounds represented by the following formulas (α-VII)-(α-IX), for example, as starting materials and reacting them.

[Chemical Formula 76]

(α-VII)

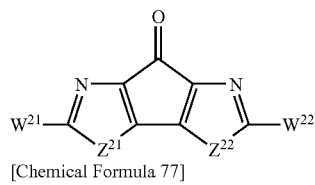

[Chemical Formula 77]

(α-VIII)

$W^{21}-Ar^{21}-W^{22}$

[Chemical Formula 78]

(α-IX)

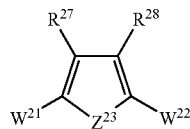

In the above formulas (α-VII)-(α-IX), $Z^{21}$, $Z^{22}$, $Z^{23}$, $R^{27}$ and $R^{28}$ have the same definitions as above. $W^{21}$ and $W^{22}$ each independently represent a halogen atom or an alkyl sulfonate group, aryl sulfonate group, arylalkyl sulfonate group, alkylstannyl group, arylstannyl group, arylalkylstannyl group, boric acid ester residue, sulfoniummethyl group, phosphoniummethyl group, phosphonatemethyl group, monohalogenated methyl group, boric acid residue, formyl group or vinyl group.

From the viewpoint of facilitating the synthesis reaction of the compounds represented by formulas (α-VII)-(α-IX), preferably $W^{21}$ and $W^{22}$ each independently represent a halogen atom or an alkyl group sulfonate group, aryl sulfonate group, arylalkyl sulfonate group, alkylstannyl group, boric acid ester residue or boric acid residue group.

Examples of reaction methods to be used for production of a nitrogen-containing fused-ring polymer of the present invention, include a method of using Wittig reaction, a method of using Heck reaction, a method of using Horner-Wadsworth-Emmons reaction, a method of using Knoevenagel reaction, a method of using Suzuki coupling reaction, a method of using Grignard reaction, a method of using Stifle reaction, a method of using Ni(0) catalyst, a method of using oxidizing agents such as $FeCl_3$, a method of using electrochemical oxidation reaction, and a method involving decomposition of an intermediate compound with an appropriate leaving group.

Of the methods mentioned above, there are preferred a method of using Wittig reaction, a method of using Heck reaction, a method of using Horner-Wadsworth-Emmons reaction, a method of using Knoevenagel reaction, a method of using Suzuki coupling reaction, a method of using Grignard reaction, a method of using Stille reaction and a method of using Ni(0) catalyst polymerization, for easier structural control. Also, a method of using Suzuki coupling reaction, a method of using Grignard reaction, a method of using Stille reaction and a method of using Ni(0) catalysts are preferred for ready availability of starting materials and simplification of the reaction procedure.

The monomer (compound represented by any one of the above formulas (α-VII)-(α-IX)) may be dissolved in an organic solvent if necessary and reacted between the melting point and boiling point of the organic solvent using an alkali or appropriate catalyst, for example.

The organic solvent used will differ depending on the compounds and reaction used, but in order to limit secondary reactions, it is preferable that the solvent is one that has been sufficiently deoxygenated and allows the reaction to proceed in an inert atmosphere. Similarly, dehydration treatment is also preferably carried out (except cases of reaction conducted in a two-phase system with water, such as the Suzuki coupling reaction).

An appropriate alkali or catalyst is added for the reaction. These may be selected as appropriate for the reaction used. It is preferable that the alkali or catalyst is one that thoroughly dissolves in the solvent used for the reaction.

When a nitrogen-containing fused-ring polymer of the present invention is to be used as a material for an organic thin-film device, since the purity will affect the device characteristics, the monomer is preferably polymerized after purification by a method such as distillation, subliming purification or recrystallization. After synthesis of the nitrogen-containing fused-ring polymer, it is preferably subjected to purifying treatment such as separation by reprecipitation or chromatography.

Examples of solvents to be used for the reaction include saturated hydrocarbons such as pentane, hexane, heptane, octane and cyclohexane, unsaturated hydrocarbons such as benzene, toluene, ethylbenzene and xylene, halogenated saturated hydrocarbons such as carbon tetrachloride, chloroform, dichloromethane, chlorobutane, bromobutane, chloropentane, bromopentane, chlorohexane, bromohexane, chlorocyclohexane and bromocyclohexane, halogenated unsaturated hydrocarbons such as chlorobenzene, dichlorobenzene and trichlorobenzene, alcohols such as methanol, ethanol, propanol, isopropanol, butanol and t-butyl alcohol, carboxylic acids such as formic acid, acetic acid and propionic acid, ethers such as dimethyl ether, diethyl ether, methyl-t-butyl ether, tetrahydrofuran, tetrahydropyran and dioxane, and inorganic acids such as hydrochloric acid, hydrobromic acid, hydrofluoric acid, sulfuric acid and nitric acid. A single solvent may be used alone or two or more may be used in combination.

The reaction may be followed by ordinary post-treatment such as, for example, quenching with water, subsequent extraction with an organic solvent and distillation of the solvent. Isolation and purification of the product can be carried out by chromatographic fractionation or recrystallization.

An organic thin film according to the present invention will now be explained. The organic thin film of the present invention comprises a nitrogen-containing fused-ring compound and/or nitrogen-containing fused-ring polymer of the present invention (hereunder collectively referred to as "nitrogen-containing compound of the present invention").

The film thickness of the organic thin film will usually be about 1 nm-100 μm, preferably 2 nm-1000 nm, even more preferably 5 nm-500 nm and most preferably 20 nm-200 nm.

The organic thin film may comprise a single nitrogen-containing compound of the present invention, or it may comprise two or more nitrogen-containing compounds of the present invention. In order to enhance the electron transport and hole transport properties of the organic thin film, a low molecular compound or high molecular compound having an electron transport or hole transport property may also be combined with the nitrogen-containing compound of the present invention.

Any known hole transport material may be used, examples of which include pyrazoline derivatives, arylamine derivatives, stilbene derivatives, triaryldiamine derivatives, oligothiophene and its derivatives, polyvinylcarbazole and its derivatives, polysilane and its derivatives, polysiloxane derivatives having aromatic amines on the side chains or main chains, polyaniline and its derivatives, polythiophene and its derivatives, polypyrrole and its derivatives, polyarylenevinylene and its derivatives or polythienylenevinylene and its derivatives, and any known electron transport materials may also be used, examples of which include oxadiazole derivatives, quinodimethane and its derivatives, benzoquinone and its derivatives, naphthoquinone and its derivatives, anthraquinone and its derivatives, tetracyanoanthraquinodimethane and its derivatives, fluorenone derivatives, diphenyldicyanoethylene and its derivatives, diphenoquinone derivatives, metal complexes of 8-hydroxyquinoline and its derivatives, polyquinoline and its derivatives, polyquinoxaline and its derivatives, polyfluorene and its derivatives, and $C_{60}$ fullerenes and their derivatives.

An organic thin film of the present invention may also contain a charge generation material for generation of an electrical charge upon absorption of light in the organic thin film. Any known charge generation materials may be used, examples of which include azo compounds and their derivatives, diazo compounds and their derivatives, ametallic phthalocyanine compounds and their derivatives, metallic phthalocyanine compounds and their derivatives, perylene compounds and their derivatives, polycyclic quinone-based compounds and their derivatives, squarylium compounds and their derivatives, azulenium compounds and their derivatives, thiapyrylium compounds and their derivatives, and $C_{60}$ fullerenes and their derivatives.

The organic thin film of the present invention may also contain materials necessary for exhibiting various functions. Examples include sensitizing agents to enhance the function of generating charge by light absorption, stabilizers to increase stability, and UV absorbers for absorption of UV light.

The organic thin film of the present invention may also contain high molecular compound materials as macromolecular binders in addition to the nitrogen-containing compound of the present invention, in order to improve the mechanical properties. It is preferable that as macromolecular binders ones that do not extremely interfere with the electron transport or hole transport property, and ones that do not have strong absorption for visible are used.

Examples of such macromolecular binders include poly (N-vinylcarbazole), polyanilines and their derivatives, polythiophenes and their derivatives, poly(p-phenylenevinylene) and its derivatives, poly(2,5-thienylenevinylene) and its derivatives, polycarbonates, polyacrylates, polymethyl acrylate, polymethyl methacrylate, polystyrene, polyvinyl chloride, polysiloxanes and the like.

The method for producing the organic thin film of the present invention may be, for example, a method of forming a film from a solution comprising the nitrogen-containing compound of the present invention, with an electron transport material or hole transport material and macromolecular binder as necessary. When the nitrogen-containing compound of the present invention has a sublimating property, the thin film may be formed by vacuum vapor deposition.

The solvent used to form the film from the solution may be any one that dissolves the nitrogen-containing compound of the present invention and the electron transport material or hole transport material and macromolecular binder combined therewith.

Examples of solvents to be used for formation of the organic thin film of the present invention from a solution include unsaturated hydrocarbon-based solvents such as toluene, xylene, mesitylene, tetralin, decalin, bicyclohexyl, n-butylbenzene, sec-butylbenzene and tert-butylbenzene, halogenated saturated hydrocarbon-based solvents such as carbon tetrachloride, chloroform, dichloromethane, dichloroethane, chlorobutane, bromobutane, chloropentane, bromopentane, chlorohexane, bromohexane, chlorocyclohexane and bromocyclohexane, halogenated unsaturated hydrocarbon-based solvents such as chlorobenzene, dichlorobenzene and trichlorobenzene, and ether-based solvents such as tetrahydrofuran and tetrahydropyran. Dissolution in these solvents will usually be to 0.1% by mass or greater, although this will depend on the structure and molecular weight of the nitrogen-containing compound of the present invention.

The method of forming the film from a solution may be a coating method such as spin coating, casting, microgravure coating, gravure coating, bar coating, roll coating, wire bar coating, dip coating, spray coating, screen printing, flexographic printing, offset printing, ink jet printing, dispenser printing, nozzle coating, capillary coating or the like, among which spin coating, flexographic printing, ink jet printing, dispenser printing, nozzle coating and capillary coating methods are preferred.

The steps for producing the organic thin film of the present invention may include a step of orienting the nitrogen-containing compound of the present invention. An organic thin film with the nitrogen-containing compound oriented by such a step will have the main chain molecules or side chain molecules aligned in a single direction, thus improving the electron mobility or hole mobility.

The method for orienting the nitrogen-containing compound may be any method known for orientation of liquid crystals. Rubbing, photoorientation, shearing (shear stress application) and pull-up coating methods are convenient, useful and easy orienting methods, and rubbing and shearing are preferred.

The steps for production of the organic thin film of the present invention may further include a step of annealing treatment after film formation. Such a step will improve the quality of the organic thin film and increase the electron mobility or hole mobility, by promoting interaction between the nitrogen-containing compounds. The treatment temperature for annealing is preferably a temperature between 50° C. and near the glass transition temperature (Tg) of the nitrogen-containing compound, and more preferably a temperature between (Tg-30° C.) and Tg. The annealing treatment time is preferably from 1 minute to 10 hours and more preferably from 10 minutes to 1 hour. The atmosphere for annealing treatment is preferably a vacuum or an inert gas atmosphere.

Since the organic thin film of the present invention has an electron transport or hole transport property, by controlling the transport of electrons or holes introduced from the electrode or charge generated by photoabsorption, the organic thin film can be used in various organic thin-film devices such as organic thin-film transistors, organic solar cells, optical sensors and the like. When an organic thin film of the present invention is used in such organic thin-film devices, it is preferably used after orientation by orienting treatment in order to further enhance the electron transport or hole transport properties.

[Organic Thin-Film Device]

Because the organic thin film of the embodiment described above comprises a nitrogen-containing compound according to the embodiment described above, it has excellent charge (electron or hole) transport properties. The organic thin film can therefore efficiently transport electrons or holes introduced from an electrode or the like, or electrical charge generated by photoabsorption, thus allowing application of the organic thin film in various electrical devices (organic thin-film devices). The nitrogen-containing compounds of the embodiment described above are also environmentally stable and have excellent solubility in organic solvents, and can therefore be used to form thin films to allow production of organic thin-film devices with stable performance even in ordinary air. Examples of organic thin-film devices will now be described.

(Organic Thin-Film Transistor)

An organic thin-film transistor according to a preferred embodiment will be explained first. The organic thin-film transistor may have a structure comprising a source electrode and drain electrode, an organic thin-film layer (active layer) containing a nitrogen-containing compound of the present invention which is to act as a current channel between them, and a gate electrode that is to control the level of current flowing through the current channel, and the examples of the transistor include a field-effect type or static induction type.

A field-effect type organic thin-film transistor may have a structure comprising a source electrode and drain electrode, an organic thin-film layer (active layer) containing a nitrogen-containing compound of the present invention which is to act as a current channel between them, a gate electrode that is to control the level of current flowing through the current channel, and an insulating layer situated between the active layer and the gate electrode. Most preferably, the source electrode and drain electrode are provided in contact with the organic thin-film layer (active layer) containing the nitrogen-containing compound of the present invention, and the gate electrode is provided sandwiching the insulating layer which is also in contact with the organic thin-film layer.

A static induction-type organic thin-film transistor has a structure comprising a source electrode and drain electrode, an organic thin-film layer containing a nitrogen-containing compound of the present invention which is to act as a current channel between them and a gate electrode that is to control the level of current flowing through the current channel, preferably with the gate electrode in the organic thin-film layer. Most preferably, the source electrode, drain electrode and gate electrode provided in the organic thin-film layer are in contact with the organic thin-film layer comprising the nitrogen-containing compound of the present invention. The structure of the gate electrode may be any one that forms a current channel for flow from the source electrode to the drain electrode, and that allows the level of current flowing through the current channel to be controlled by the voltage applied to the gate electrode; an example of such a structure is a comb shaped electrode.

FIG. 1 is a schematic cross-sectional view of an organic thin-film transistor (field-effect type organic thin-film transistor) according to a first embodiment. The organic thin-film transistor 100 shown in FIG. 1 comprises a substrate 1, a source electrode 5 and drain electrode 6 formed at a prescribed spacing on the substrate 1, an active layer 2 formed on the substrate 1 covering the source electrode 5 and drain electrode 6, an insulating layer 3 formed on the active layer 2, and a gate electrode 4 formed on the insulating layer 3 covering the region of the insulating layer 3 between the source electrode 5 and drain electrode 6.

FIG. 2 is a schematic cross-sectional view of an organic thin-film transistor (field-effect type organic thin-film transistor) according to a second embodiment. The organic thin-film transistor 110 shown in FIG. 2 comprises a substrate 1, a source electrode 5 formed on the substrate 1, an active layer 2 formed on the substrate 1 covering the source electrode 5, a drain electrode 6 formed on the active layer 2 at a prescribed spacing from the source electrode 5, an insulating layer 3 formed on the active layer 2 and drain electrode 6, and a gate electrode 4 formed on the insulating layer 3 covering the region of the insulating layer 3 between the source electrode 5 and drain electrode 6.

FIG. 3 is a schematic cross-sectional view of an organic thin-film transistor (field-effect type organic thin-film transistor) according to a third embodiment. The organic thin-film transistor 120 shown in FIG. 3 comprises a substrate 1, an active layer 2 formed on the substrate 1, a source electrode 5 and drain electrode 6 formed at a prescribed spacing on the active layer 2, an insulating layer 3 foamed on the active layer 2 covering the source electrode 5 and drain electrode 6, and a gate electrode 4 formed on the insulating layer 3, covering a portion of the region of the insulating layer 3 under which the source electrode 5 is formed and a portion of the region of the insulating layer 3 under which the drain electrode 6 is formed.

FIG. 4 is a schematic cross-sectional view of an organic thin-film transistor (field-effect type organic thin-film transistor) according to a fourth embodiment. The organic thin-film transistor 130 shown in FIG. 4 comprises a substrate 1, a gate electrode 4 fowled on the substrate 1, an insulating layer 3 formed on the substrate 1 covering the gate electrode 4, a source electrode 5 and drain electrode 6 formed at a prescribed spacing on the insulating layer 3 covering portions of the region of the insulating layer 3 under which the gate electrode 4 is formed, and an active layer 2 formed on the insulating layer 3 covering portions of the source electrode 5 and drain electrode 6.

FIG. 5 is a schematic cross-sectional view of an organic thin-film transistor (field-effect type organic thin-film transistor) according to a fifth embodiment. The organic thin-film transistor 140 shown in FIG. 5 comprises a substrate 1, a gate electrode 4 formed on the substrate 1, an insulating layer 3 formed on the substrate 1 covering the gate electrode 4, a source electrode 5 formed on the insulating layer 3 covering a portion of the region of the insulating layer 3 under which the gate electrode 4 is formed, an active layer 2 formed on the insulating layer 3 covering a portion of the source electrode 5, and a drain electrode 6 formed on the insulating layer 3 at a prescribed spacing from the source electrode 5 and covering a portion of the region of the active layer 2 under which the gate electrode 4 is formed.

FIG. 6 is a schematic cross-sectional view of an organic thin-film transistor (field-effect type organic thin-film transistor) according to a sixth embodiment. The organic thin-film transistor 150 shown in FIG. 6 comprises a substrate 1, a gate electrode 4 formed on the substrate 1, an insulating layer 3 formed on the substrate 1 covering the gate electrode 4, an active layer 2 formed covering the region of the insulating layer 3 under which the gate electrode 4 is formed, a source electrode 5 formed on the insulating layer 3 covering a portion of the region of the active layer 2 under which the gate electrode 4 is formed, and a drain electrode 6 formed on the insulating layer 3 at a prescribed spacing from the source electrode 5 and covering a portion of the region of the active layer 2 under which the gate electrode 4 is formed.

FIG. 7 is a schematic cross-sectional view of an organic thin-film transistor (static induction type organic thin-film transistor) according to a seventh embodiment. The organic thin-film transistor 160 shown in FIG. 7 comprises a substrate 1, a source electrode 5 formed on the substrate 1, an active layer 2 formed on the source electrode 5, a plurality of gate electrodes 4 formed at prescribed spacings on the active layer 2, an active layer 2a formed on the active layer 2 covering all of the gate electrodes 4, wherein the material composing the active layer 2a may be the same as or different from that of the active layer 2, and a drain electrode 6 formed on the active layer 2a.

In the organic thin-film transistors of the first to seventh embodiments, the active layer 2 and/or the active layer 2a contains a nitrogen-containing compound of the present invention and forms a current channel between the source electrode 5 and drain electrode 6. The gate electrode 4 controls the level of current flowing through the current channel of the active layer 2 and/or active layer 2a by application of voltage.

This type of field-effect type organic thin-film transistor can be manufactured by a publicly known process, such as the process described in Japanese Unexamined Patent Publication HEI No. 5-110069, for example. The static induction type organic thin-film transistor can also be manufactured by a publicly known process such as the process described in Japanese Unexamined Patent Publication No. 2004-006476, for example.

The substrate 1 is not particularly restricted so long as it does not impair the characteristics of the organic thin-film transistor, and a glass panel, flexible film substrate or plastic panel may be used.

Since organic solvent-soluble compounds are highly advantageous and preferred in forming the active layer 2, by using the organic thin-film production method of the present invention described above, organic thin films composed of the active layer 2 can be formed.

The insulating layer 3 in contact with the active layer 2 is not particularly restricted so long as it is a material with high electrical insulating properties, and any publicly known one may be used. Examples include SiOx, SiNx, $Ta_2O_5$, polyimide, polyvinyl alcohol, polyvinylphenol, organic glass and photoresists. From the viewpoint of low voltage, a material with high permittivity is preferred.

When the active layer 2 is formed on the insulating layer 3, it may be formed after surface modification by treatment of the surface of the insulating layer 3 with a surface treatment agent such as a silane coupling agent in order to improve the interfacial properties between the insulating layer 3 and active layer 2. As examples of surface treatment agents there may be mentioned long-chain alkylchlorosilanes, long-chain alkylalkoxysilanes, fluorinated alkylchlorosilanes, fluorinated alkylalkoxysilanes and silylamine compounds such as hexamethyldisilazane. Before treatment with the surface treatment agent, the insulating layer surface may be pretreated by ozone UV or $O_2$ plasma.

After the organic thin-film transistor has been fabricated, in order to protect the device, it is preferable that a protecting film is formed on the organic thin-film transistor. This will help prevent reduction in the characteristics of the organic thin-film transistor due to shielding from air. A protecting film can also minimize adverse effects from the step of forming an operating display device on the organic thin-film transistor.

Examples of the method of forming the protecting film include covering with a UV curing resin, thermosetting resin, inorganic SiONx film or the like. For effective shielding from air, the steps after fabrication of the organic thin-film transistor and before formation of the protecting film are preferably carried out without exposure to air (for example, in a dry nitrogen atmosphere or in a vacuum).

Application of an organic thin film of the present invention in a solar cell will now be explained. FIG. 8 is a schematic cross-sectional view of a solar cell according to an embodiment. The solar cell 200 shown in FIG. 8 comprises a substrate 1, a first electrode 7a formed on the substrate 1, an active layer 2 comprising an organic thin film that contains a nitrogen-containing compound of the present invention formed on the first electrode 7a, and a second electrode 7b formed on the active layer 2.

In the solar cell of this embodiment, a transparent or semi-transparent electrode is used for either the first electrode 7a or the second electrode 7b. As electrode materials there may be used metals such as aluminum, gold, silver, copper, alkali metal and alkaline earth metals or their semi-transparent films, or transparent conductive films. In order to obtain high open voltage, it is preferred to select the electrodes so as to produce a large work function difference. Charge generators, sensitizing agents and the like may also be added in order to increase photosensitivity in the active layer 2 (organic thin film). The substrate 1 may be a silicon substrate, glass panel, plastic panel or the like.

Application of an organic thin film of the present invention in an optical sensor will now be explained. FIG. 9 is a schematic cross-sectional view of an optical sensor according to a first embodiment. The optical sensor 300 shown in FIG. 9 comprises a substrate 1, a first electrode 7a formed on the substrate 1, an active layer 2 comprising an organic thin film that contains a nitrogen-containing compound of the present invention formed on the first electrode 7a, a charge generation layer 8 formed on the active layer 2 and a second electrode 7b formed on the charge generation layer 8.

FIG. 10 is a schematic cross-sectional view of an optical sensor according to a second embodiment. The optical sensor 310 shown in FIG. 10 comprises a substrate 1, a first electrode 7a formed on the substrate 1, a charge generation layer 8 formed on the first electrode 7a, an active layer 2 comprising an organic thin film that contains a nitrogen-containing compound of the present invention formed on the charge generation layer 8 and a second electrode 7b formed on the active layer 2.

FIG. 11 is a schematic cross-sectional view of an optical sensor according to a third embodiment. The optical sensor 320 shown in FIG. 11 comprises a substrate 1, a first electrode 7a formed on the substrate 1, an active layer 2 comprising an organic thin film that contains a nitrogen-containing compound of the present invention formed on the first electrode 7a, and a second electrode 7b fowled on the active layer 2.

In the optical sensors of the first to third embodiments, a transparent or semi-transparent electrode is used for either the first electrode 7a or the second electrode 7b. The charge generation layer 8 is a layer that generates an electrical charge upon absorption of light. As electrode materials there may be used metals such as aluminum, gold, silver, copper, alkali metal and alkaline earth metals or their semi-transparent films, or transparent conductive films. Carrier generators, sensitizing agents and the like may also be added in order to increase photosensitivity in the active layer 2 (organic thin film). The substrate 1 may be a silicon substrate, glass panel, plastic panel or the like.

The present invention was explained above in detail based on embodiments thereof. However, the present invention is not limited to these described embodiments. The present invention may also be applied in a variety of modifications so long as the gist thereof is maintained.

EXAMPLES

The present invention will now be explained in detail by examples, with the understanding that the present invention is not limited to the examples.

An example of the first invention group will be explained first.

(Measuring Conditions)

The nuclear magnetic resonance (NMR) spectra were measured using a JMN-270 (270 MHz for $^1H$ measurement) or a JMNLA-600 (600 MHz for $^{19}F$ measurement), both trade names of JEOL Corp. The chemical shifts are represented as parts per million (ppm). Tetramethylsilane (TMS) was used as the internal standard (0 ppm). The coupling constant (J) is represented in Hz, and the symbols s, d, t, q, m and br respectively represent singlet, doublet, triplet, quartet, multiplet and broad. The mass spectrometry (MS) was performed using a GCMS-QP5050A, trade name of Shimadzu Corp., by electron ionization (EI) or direct inlet (DI). The silica gel used for separation by column chromatography was Silicagel 60N (40-50 μm), trade name of Kanto Kagaku Co., Ltd. All of the chemical substances were reagent grade and purchased from Wako Pure Chemical Industries, Ltd., Tokyo Kasei Kogyo Co., Ltd., Kanto Kagaku Co., Ltd., Nacalai Tesque, Inc., Sigma Aldrich Japan, KK. or Daikin Chemicals Co., Ltd.

Cyclic voltammetry was performed using a CV-50W, trade name of BAS as the measuring apparatus, with a Pt electrode by BAS as the work electrode, Pt wire as the counter electrode and Ag wire as the reference electrode. The sweep rate during the measurement was 100 mV/sec, and the scanning potential range was −2.0 V to 1.6 V. The reduction potential and oxidation potential were measured after completely dissolving $1 \times 10^{-3}$ mol/L of the conjugated compound and 0.1 mol/L of tetrabutylammonium hexafluorophosphate (TBAPF6) as a supporting electrolyte in a monofluorobenzene solvent.

Example 1
Synthesis of Compound A>

To a heat-dried stoppered test tube there were added 5,5'-ditributylstannyl-2,2'-bithiophene (1.49 g, 2.00 mmol), 4'-bromo-2,2,2-trifluoroacetophenone (1.27 g, 5.00 mmol), tetrakis(triphenylphosphine)palladium(0) (100 mg, 0.087 mmol) and toluene (20 mL), and reaction was conducted at 120° C. with nitrogen exchange. After 19 hours, water was added, extraction was performed with chloroform, and the organic phase dried over magnesium sulfate and concentrated under reduced pressure. The obtained concentrate was rinsed with methanol and ether and subjected to sublimation purification in a vacuum, to obtain compound A represented by the following formula (21) (863 mg, 85% yield) as a red solid. The reduction potential of compound A was −1.70 V.

TLC $R_f$=0.2 (hexane); $^1$H-NMR (400 MHz, CDCl$_3$) δ8.10 (m, 2H), 7.77 (m, 2H), 7.47 (d, 2H, J=3.9 Hz), 7.30 (d, 2H, J=3.9 Hz); GC-MS (DI) m/z=510 (M$^+$)

[Chemical Formula 79]

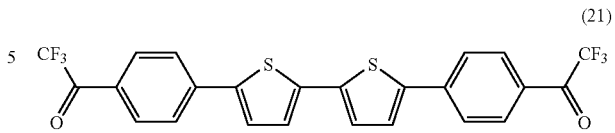

(21)

Comparative Example 1

Synthesis of Compound B>

To a heat-dried stoppered test tube there were added 5,5'-dibromo-2,2'-bithiophene (242 mg, 0.75 mmol), 4-acetylphenylboronic acid (366 mg, 2.23 mmol), tetrakis(triphenylphosphine)palladium(0) (40 mg, 0.035 mmol), sodium hydrogencarbonate (438 mg, 5.21 mmol) and a dimethoxyethane (DME)/water mixed solvent (7 mL), and reaction was conducted at 100° C. with nitrogen exchange. After 14 hours, the reaction mixture was concentrated under reduced pressure to obtain a concentrate. The obtained concentrate was rinsed with methanol and ether and then subjected to sublimation purification in a vacuum, to obtain compound B represented by the following formula (22) (205 mg, 83% yield) as a light yellow solid. The reduction potential of compound B could not be measured because it was insoluble in monofluorobenzene.

TLC $R_f$=0.0 (chloroform); $^1$H-NMR (400 MHz, CDCl$_3$); δ7.96 (m, 2H), 7.68 (m, 2H), 7.36 (m, 2H), 7.23 (m, 2H), 2.60 (s, 3H); GC-MS (DI) m/z=402 (M$^+$)

[Chemical Formula 80]

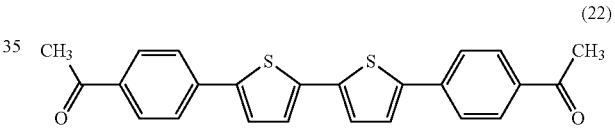

(22)

Example 2

The intermediate as the starting material for the target compound was synthesized using compound (23a) as the starting material, according to the following Scheme 1. This will now be explained in detail.

Scheme 1

[Chemical Formula 81]

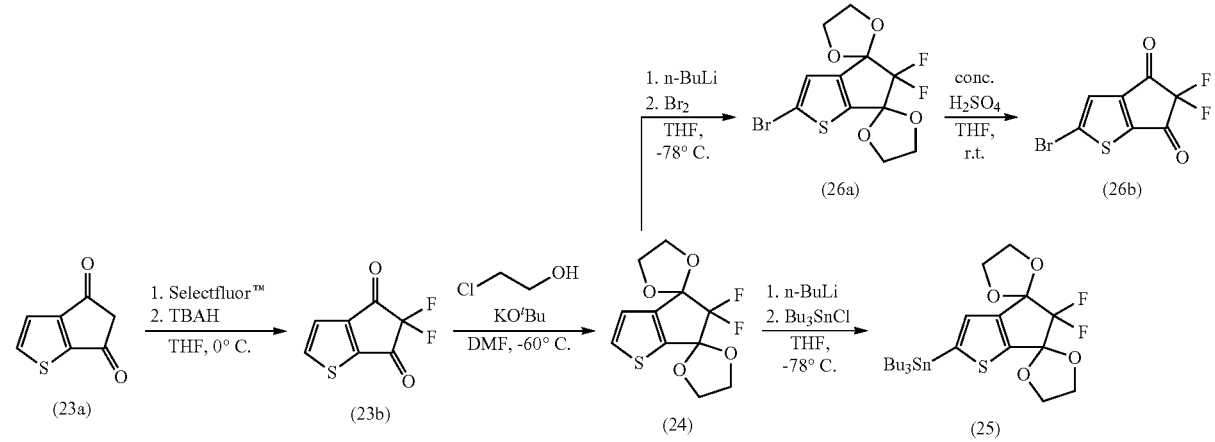

Synthesis of Compound D

Compound C-1 represented by the above formula (23a) was synthesized by a method described in the literature (J. Chem. Soc. Perkin Trans 1. Organic and Bio-Organic Chemistry 1992, 21, 2985-2988). Next, compound C-1 (1.00 g, 6.58 mol) and the fluorinating agent Selectfluor™ (registered trademark) (5.60 g, 15.8 mol) were placed in a 300 mL three-necked flask and THF (65 mL) was added to dissolve them. Tetrabutylammonium hydroxide (TBAH) (10% methanol solution) (3.76 g, 14.5 mol) was then added and the mixture was stirred at 0° C. for 12 hours. The solvent was distilled off under reduced pressure, and then water was added, the aqueous phase was extracted with ethyl acetate, and the organic phase was dried over magnesium sulfate and concentrated under reduced pressure. The obtained concentrate was purified by silica gel column chromatography (hexane/ethyl acetate=3/1) to obtain compound C-2 represented by the above formula (23b) (0.934 g, 75%) as a light yellow solid.

mp 156-158° C.; TLC $R_f$=0.29 (2:1=hexane/ethyl acetate); $^1$H-NMR (400 MHz, CDCl$_3$) δ7.60 (d, 1H, J=4.8 Hz), 8.28 (d, 1H, J=4.8 Hz); MS (EI) m/z=188 (M$^+$)

Compound C-2 (1.97 g, 10.48 mmol) was placed in a 200 mL three-necked flask, N,N'-dimethylformamide (DMF) (50 mL) was added to dissolve it, and then 2-chloromethanol (3.37 g, 41.91 mmol) was further added. Potassium tert-butoxide dissolved in DMF (50 mL) was then added dropwise thereto at −60° C. Upon completion of the dropwise addition, the mixture was stirred at room temperature for 4 hours, and water was added to suspend the reaction. The aqueous phase was extracted with ethyl acetate and rinsed with water, and then the organic phase was dried over magnesium sulfate, filtered and concentrated under reduced pressure. The obtained concentrate was purified by silica gel column chromatography (hexane/ethyl acetate=3/1) to obtain compound D represented by the above formula (24) (1.58 g, 55% yield) as a white solid.

mp 117-122° C.; TLC $R_f$=0.34 (2:1=hexane/ethyl acetate); $^1$H-NMR (400 MHz, CDCl$_3$) δ4.26 (s, 8H), 7.02 (d, 1H, J=4.8 Hz), 7.51 (d, 1H, J=5.1 Hz); MS (EI) m/z=276 (M$^+$)

Synthesis of Compound E

Compound D (500 mg, 1.81 mmol) was placed in a 50 mL three-necked flask, and THF (18 mL) was added to dissolve it. Next, n-butyllithium (1.58 M, 2.29 mL, 3.62 mmol) was added thereto at −78° C. After stirring for 0.5 hour, tributyltin chloride (1.09 mL, 3.98 mmol) was added and the temperature was slowly raised to room temperature. After 1 hour, water was added to suspend the reaction. The aqueous phase was extracted with ethyl acetate and rinsed with water, and then the organic phase was dried over magnesium sulfate, filtered and concentrated under reduced pressure. The obtained concentrate was purified by alumina-column chromatography (hexane/ethyl acetate=10:1) to obtain compound E represented by the above formula (25) (1.02 g, 99% yield) as a colorless liquid.

TLC $R_f$=0.30 (hexane); $^1$H-NMR (400 MHz, CDCl$_3$) δ0.89 (t, 9H, J=7.2 Hz), 1.08-1.13 (m, 6H), 1.24-1.38 (m, 6H), 1.49-1.60 (m, 6H), 4.23-4.28 (m, 8H), 7.03 (s, 1H); MS (EI) m/z=566 (M$^+$)

Synthesis of Compound F

Compound D (1.00 g, 3.62 mmol) was placed in a 100 mL three-necked flask, and THF (30 mL) was added to dissolve it. Next, n-butyllithium (1.58 M, 2.75 mL, 4.34 mmol) was added thereto at −78° C. After stirring for 0.5 hour, bromine (0.29 mL, 5.43 mmol) was added and the temperature was slowly raised to room temperature. After 1 hour, water was added to suspend the reaction. The aqueous phase was extracted with ethyl acetate and rinsed with saturated aqueous sodium thiosulfate, and after further rinsing with water, the organic phase was dried over magnesium sulfate. The solvent was distilled off under reduced pressure, and the crude product was passed through silica gel column chromatography (hexane/ethyl acetate=3:1) to obtain a crude product of the intermediate compound represented by the above formula (26a). This was placed in a 100 mL volumetric flask and dissolved in THF (30 mL). Concentrated sulfuric acid (30 mL) was added and the mixture was stirred at room temperature for 12 hours. The reaction mixture was poured into ice and extracted with water. The organic phase was rinsed with aqueous saturated sodium hydrogencarbonate and water in that order and dried over magnesium sulfate, and then filtered and concentrated under reduced pressure. The obtained concentrate was purified by silica gel column chromatography (ethyl acetate) to obtain compound F represented by the above formula (26b) (877 mg, 91% in 2 steps) as a brown solid.

TLC $R_f$=0.21 (3:1=hexane/ethyl acetate); $^1$H-NMR (400 MHz, CDCl$_3$) δ7.60 (s, 1H); MS (EI) m/z=266 (M$^+$)

Synthesis of Compound G

After placing 2,5-dibromothiophene (18 mg, 0.0738 mmol), compound E (100 mg, 0.177 mmol) and tetrakis(triphenylphosphine)palladium(0) (17 mg, 0.0148 mmol) in a test tube, toluene (1 mL) was added to dissolve them. After stirring the mixture at 120° C. for 12 hours, it was allowed to cool at room temperature. The solvent was then distilled off under reduced pressure, and the crude product was passed through alumina-column chromatography (hexane/ethyl acetate=3:1) and purified by GPC (chloroform) to obtain compound G represented by the following formula (27) (35 mg, 74%) as a light yellow solid.

mp 273-275° C.; TLC $R_f$=0.68 (1:2=hexane/ethyl acetate); $^1$H-NMR (400 MHz, CDCl$_3$) δ4.25-4.29 (m, 16H), 7.06 (s, 2H), 7.11 (s, 2H); MS (EI) m/z=632 (M$^+$)

[Chemical Formula 82]

(27)

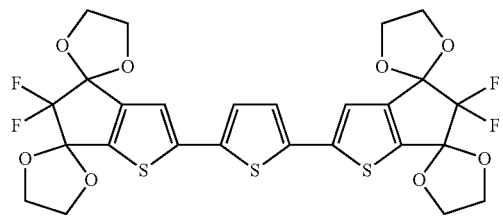

Synthesis of Compound H

Compound G (35 mg, 0.0550 mmol) was placed in a test tube, and THF (3 mL) was added to dissolve it. Concentrated sulfuric acid (3 mL) was added and the mixture was stirred at room temperature for 12 hours. The reaction mixture was poured into ice and extracted with water. The organic phase was rinsed with aqueous saturated sodium hydrogencarbonate and water in that order and dried over magnesium sulfate, and then filtered and concentrated under reduced pressure. The obtained concentrate was rinsed with diethyl ether to obtain compound H represented by the following formula (28) (18 mg, 72% yield) as a red solid. The reduction potential of compound H was −1.24 V.

TLC $R_f$=0.62 (1:2=hexane/ethyl acetate); $^1$H-NMR (400 MHz, CDCl$_3$) δ7.56 (s, 2H), 7.63 (s, 2H); MS (EI) m/z=456 (M$^+$)

[Chemical Formula 83]

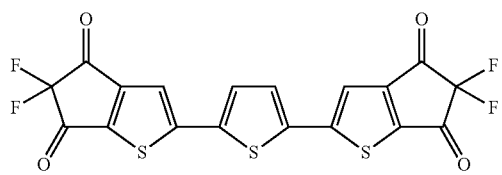

(28)

Example 3

Synthesis of Compound I

After placing 1,3-dibromo-5,5-difluoro-4H-cyclopenta[c]thiophene-4,6(5H)-dione (26 mg, 0.0738 mmol), compound E (100 mg, 0.177 mmol) and tetrakis(triphenylphosphine)palladium(0) (17 mg, 0.0148 mmol) in a test tube, toluene (1 mL) was added to dissolve them. After stirring the mixture at 120° C. for 12 hours, it was allowed to cool at room temperature. The solvent was then distilled off under reduced pressure, and the crude product was passed through alumina-column chromatography (chloroform) and purified by GPC (chloroform) to obtain compound I represented by the following formula (29) (33 mg, 61%) as a yellow solid.

TLC $R_f$=0.59 (1:2=hexane/ethyl acetate); $^1$H-NMR (400 MHz, CDCl$_3$) δ4.28-4.31 (m, 16H), 8.00 (s, 2H); MS (EI) m/z=736 (M$^+$)

[Chemical Formula 84]

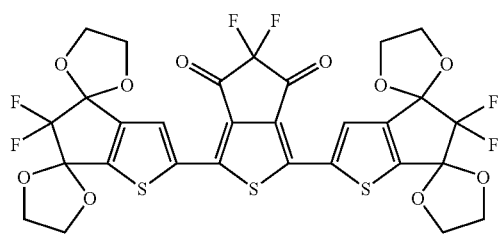

(29)

Synthesis of Compound J

Compound I (72 mg, 0.0978 mmol) was placed in a test tube, and THF (7 mL) was added to dissolve it. Concentrated sulfuric acid (7 mL) was added and the mixture was stirred at room temperature for 12 hours. The reaction mixture was poured into ice and extracted with water, and then the organic phase was rinsed with aqueous saturated sodium hydrogencarbonate and water in that order and dried over magnesium sulfate, and then filtered and concentrated under reduced pressure. The obtained concentrate was recrystallized with hexane/chloroform to obtain compound J represented by the following formula (30) (21 mg, 38%) as a light a yellow solid. The reduction potential of compound J was −0.66 V.

TLC $R_f$=0.32 (1:2=hexane/ethyl acetate); $^1$H-NMR (400 MHz, CDCl$_3$) δ8.40 (s, 2H); MS (EI) m/z=560 (10

[Chemical Formula 85]

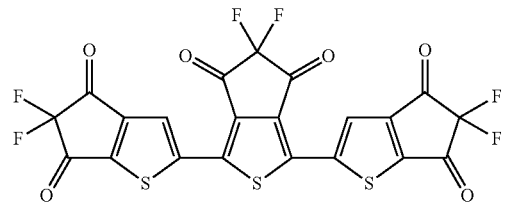

(30)

Comparative Example 2

Synthesis of Compound K>

In a heat-dried stoppered test tube there were placed 1,3-dibromo-5,5-difluoro-4H-cyclopenta[c]thiophene-4,6(5H)-dione (589 mg, 1.70 mmol), 2-tributylstannylthiophene (1.32 g, 5.10 mmol) and tetrakis(triphenylphosphine)palladium(0) (196 mg, 0.17 mmol). Toluene (10 mL) was added and reaction was conducted at 120° C. The mixture was allowed to cool after 12 hours and then extracted with ethyl acetate, and the organic phase was dried over anhydrous sodium sulfate and then filtered and concentrated under reduced pressure. The obtained concentrate was purified by column chromatography (silica gel, chloroform charge) using hexane/ethyl acetate (4/1) as the developing solvent, to obtain compound K represented by the following formula (31) (186 mg, 31%) as a red solid. The reduction potential of compound K was −1.34 V.

TLC $R_f$=0.44 (4:1=hexane/ethyl acetate); $^1$H-NMR (270 MHz, CDCl$_3$) δ8.17-8.19 (m, 2H), 7.55-7.57 (m, 2H), 7.18-7.22 (m, 2H); MS (EI) m/z=352 (M$^+$)

[Chemical Formula 86]

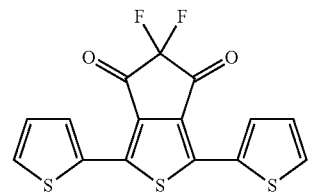

(31)

Example 4

Synthesis of Compound L

After placing 5,5'-bis(tributylstannyl)-2,2'-bithiophene (413 mg, 0.555 mmol), compound F (326 mg, 1.22 mmol) and tetrakis(triphenylphosphine)palladium(0) (64 mg, 0.056 mmol) in a test tube, toluene (6 mL) was added to dissolve them. After stirring the mixture at 120° C. for 12 hours, it was allowed to cool at room temperature. The reaction mixture was filtered with Celite and the solvent was distilled off under reduced pressure, after which the obtained solid was rinsed with hexane to obtain compound L represented by the following formula (32) (35 mg, 74%) as a dark violet solid.

mp>300° C.; MS (EI) m/z=538 (M$^+$)

[Chemical Formula 87]

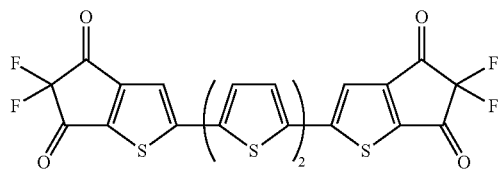

(32)

Example 5

Fabrication of Organic Thin-Film Device 1 and Evaluation of Transistor Property

A substrate was prepared by forming a silicon oxide film as the insulating layer, by thermal oxidation to a thickness of 300 nm on the surface of a highly doped p-type silicon substrate as the gate electrode. The lift-off method was used to form on this substrate a comb-shaped source electrode and drain electrode with a channel width of 38 mm and a channel length of 5 μm. The electrode-formed substrate was subjected to ultrasonic cleaning for 10 minutes in acetone and for 10 minutes in isopropyl alcohol, after which it was irradiated with ozone UV for 30 minutes to clean the surface. An organic thin film of compound A synthesized in Example 1 was formed on the cleaned substrate by vacuum vapor deposition, to fabricate organic thin-film device 1. The organic transistor property was measured by varying the gate voltage Vg from 0 to 100 V and the source-drain voltage Vsd from 0 to 100 V for the organic thin-film device 1 in a vacuum, and a satisfactory n-type semiconductor Id-Vg characteristic was obtained. The mobility during this time was $3.4 \times 10^{-3}$ cm$^2$/Vs, and the on/off ratio was satisfactory at $10^4$-$10^5$.

Comparative Example 3

Fabrication of Organic Thin-Film Device 2 and Evaluation of Transistor Property

An organic thin film of compound B synthesized in Comparative Example 1 was fanned in the same manner as Example 5 to fabricate organic thin-film device 2. The organic transistor property was measured by varying the gate voltage Vg from 0 to 100 V and the source-drain voltage Vsd from 0 to 100 V for the obtained organic thin-film device 2 in a vacuum, to obtain the Id-Vg characteristic of the p-type semiconductor. The mobility during this time was $1.8 \times 10^{-5}$ cm$^2$/Vs, and the on/off ratio was low at $10^2$.

Example 6

Fabrication of Organic Thin-Film Device 3 and Evaluation of Transistor Property

An organic thin film of compound L synthesized in Example 4 was formed in the same manner as Example 5, to fabricate organic thin-film device 3. The organic transistor property was measured by varying the gate voltage Vg from 0 to 100 V and the source-drain voltage Vsd from 0 to 100 V for the obtained organic thin-film device 3 in a vacuum, to obtain a satisfactory Id-Vg characteristic for the n-type semiconductor. The mobility during this time was $1.5 \times 10^{-3}$ cm$^2$/Vs, and the on/off ratio was satisfactory at $10^4$.

Example 7

Fabrication of Organic Thin-Film Device 4 and Evaluation of Transistor Property

A substrate was prepared by forming a silicon oxide film, as the insulating layer, by thermal oxidation to a thickness of 300 nm on the surface of a highly doped p-type silicon substrate as the gate electrode. The substrate was immersed in hexamethyldisilazane (HMDS) by Aldrich at 50° C. for 7 hours for surface treatment. An organic thin film of compound A was then accumulated on the surface-treated substrate to a film thickness of 30 nm, by vacuum vapor deposition at room temperature. Au was formed to a thickness of 30 nm on the organic thin film by vapor deposition through a shadow mask, to form a source electrode and drain electrode with a channel width of 5.5 mm and a channel length of 50 μm, thus fabricating organic thin-film device 4. The transistor property of the obtained organic thin-film device 4 was measured while varying the gate voltage Vg and the source-drain voltage Vsd in nitrogen, and as a result a satisfactory Id-Vg property was confirmed and a drain current of $Id=1.1 \times 10^{-4}$ A flowed at Vg=100 V, Vd=100 V. The mobility was 0.12 cm$^2$/Vs, and the threshold voltage with current on was Vth=60 V. These results confirmed that the organic thin-film device 4 using compound A effectively functions as an n-type organic transistor.

Example 8

Fabrication of Organic Thin-Film Device 5 and Evaluation of Transistor Property

An organic thin-film device 5 was fabricated in the same manner as Example 7 using an organic thin film of compound L instead of an organic thin film of compound A. The transistor property of the obtained organic thin-film device 5 was measured while varying the gate voltage Vg and the source-drain voltage Vsd in nitrogen, and as a result a satisfactory Id-Vg property was confirmed and a drain current of $Id=1.5 \times 10^{-5}$ A flowed at Vg=80 V, Vd=100 V. The mobility was 0.013 cm$^2$/Vs, the on/off ratio was $10^5$, and the threshold voltage with current on was Vth=38 V. These results confirmed that the organic thin-film device 5 using compound L effectively functions as an n-type organic transistor.

Example 9

Synthesis of Compound M

After placing 2-bromo-3-hexylthiophene (600 mg, 2.43 mmol), compound E synthesized in Example 2 (1.51 g, 2.67 mmol) and tetrakis(triphenylphosphine)palladium(0) (281 mg, 0.243 mmol) in a heat-dried stoppered test tube, toluene (25 mL) was added to dissolve them. After stirring the mixture at 120° C. for 12 hours, it was allowed to cool at room temperature. The solvent was then distilled off under reduced pressure, and the obtained crude product was purified by silica gel column chromatography (hexane/ethyl acetate=10: 1) to obtain compound M represented by the following formula (33) (960 mg, 81% yield) as a yellow liquid.

TLC $R_f$=0.46 (5:1=hexane/ethyl acetate); $^1$H-NMR (400 MHz, CDCl$_3$) δ0.89 (t, 3H, J=3.6 Hz), 1.23-1.43 (m, 4H), 1.53-1.69 (m, 4H), 2.72 (t, 2H, J=8.0 Hz), 4.27 (s, 8H), 6.94 (d, 1H, J=5.4 Hz), 6.97 (s, 1H), 7.22 (d, 1H, J=5.4 Hz); MS (EI) m/z 442 (M$^+$).

[Chemical Formula 88]

(33)

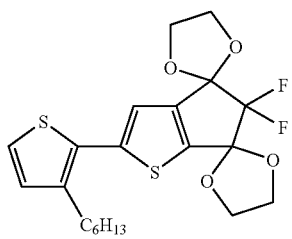

Synthesis of Compound N

Compound M (300 mg, 0.679 mmol) was placed in a heat-dried 20 mL three-necked flask, and THF (7 mL) was added to dissolve it. Next, n-butyllithium (1.58 M, 0.88 mL, 1.39 mmol) was added thereto at −78° C. After stirring for 1 hour, tributyltin chloride (0.221 ml, 0.814 mmol) was added and the temperature was slowly raised to room temperature. After 0.5 hour, water was added to suspend the reaction. The aqueous phase was extracted with ethyl acetate and rinsed with water, and then the organic phase was dried over magnesium sulfate. The solvent was distilled off under reduced pressure, and the obtained crude product was purified by alumina column chromatography (hexane/ethyl acetate=10:1) to obtain compound N represented by the following formula (34) (440 mg, 89% yield) as a yellow liquid.

TLC $R_f$=0.67 (5:1=hexane/ethyl acetate); $^1$H-NMR (400 MHz, CDCl$_3$) δ0.85-0.93 (m, 12H), 1.07-1.13 (m, 6H), 1.26-1.40 (m, 10H), 1.51-1.67 (m, 10H), 2.74 (t, 2H, 8.0 Hz), 4.27 (s, 8H), 6.95 (s, 1H), 6.96 (s, 1H); MS (EI) m/z=732 (M$^+$).

[Chemical Formula 89]

(34)

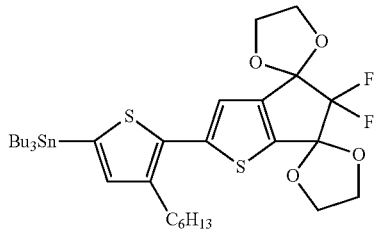

Synthesis of Compound O

After placing 1,3-dibromo-5,5-difluoro-4H-cyclopenta[c]thiophene-4,6(5H)-dione (93 mg, 0.27 mmol), compound N (435 mg, 0.594 mmol) and tetrakis(triphenylphosphine)palladium(0) (31 mg, 0.027 mmol) in a test tube, toluene (3 mL) was added to dissolve them. After stirring the mixture at 120° C. for 12 hours, it was allowed to cool at room temperature. The solvent was distilled off under reduced pressure, and the obtained crude product was passed through silica gel column chromatography (CHCl$_3$) and then purified by GPC(CHCl$_3$) to obtain compound O represented by the following formula (35) (230 mg, 80% yield) as a red solid.

TLC $R_f$=0.39 (2:1=hexane/ethyl acetate); $^1$H-NMR (400 MHz, CDCl$_3$) δ0.90 (t, 6H, J=7.1 Hz), 1.29-1.46 (m, 12H), 1.65-1.75 (m, 4H), 2.79 (t, 4H, J=7.9 Hz), 4.30 (s, 16H), 7.13 (s, 2H), 8.03 (s, 2H).

[Chemical Formula 90]

(35)

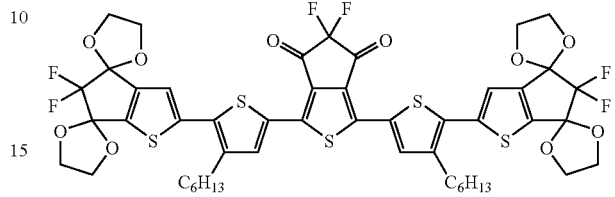

Synthesis of Compound P

Compound O (250 mg, 0.234 mmol) was placed in a volumetric flask (30 mL) and THF (3 mL) was added to dissolve it. Concentrated sulfuric acid (10 mL) was added and the mixture was stirred at room temperature for 12 hours. The obtained reaction mixture was poured into ice and extraction was performed with ethyl acetate. The organic phase was rinsed with aqueous saturated sodium hydrogencarbonate and then with water and dried over magnesium sulfate. The solvent was distilled off under reduced pressure, and the obtained solid was purified by GPC(CHCl$_3$) to obtain compound P represented by the following formula (36) (99 mg, 47% yield) as a red solid.

TLC $R_f$=0.57 (2:1=hexane/ethyl acetate); $^1$H-NMR (400 MHz, CDCl$_3$) δ0.92 (t, 6H, J=7.1 Hz), 1.23-1.52 (m, 12H), 1.73-1.83 (m, 4H), 2.91 (t, 4H, J=7.9 Hz), 7.63 (s, 2H), 8.12 (s, 2H); MS (EI) m/z=892 (M$^+$).

[Chemical Formula 91]

(36)

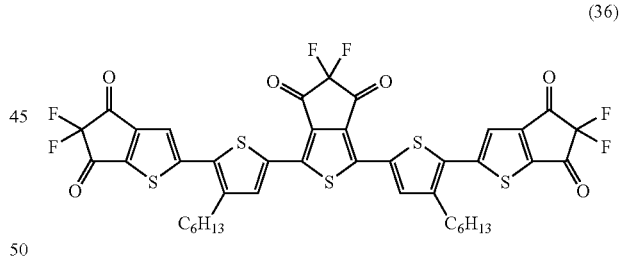

Example 10

Synthesis of Compound Q

After placing 5,5'-dibromo-4,4'-dihexyl-2,2'-bithiophene (492 mg, 1.00 mmol) in a 20 mL three-necked flask, THF (10 mL) was added to dissolve it. Next, n-butyllithium (1.58 M, 1.39 mL, 2.20 mmol) was added thereto at −78° C. After stirring for 1 hour, tributyltin chloride (0.543 ml, 2.00 mmol) was added and the temperature was slowly raised to room temperature. After 2 hours, water and a trace amount of hydrochloric acid were added to suspend the reaction. The aqueous phase was extracted with diethyl ether and rinsed with water, and then the organic phase was dried over magnesium sulfate. The solvent was distilled off under reduced pressure, and the obtained liquid was purified by GPC (CHCl₃) to obtain compound Q represented by the following formula (37) (630 mg, 69% yield) as a yellow liquid.

TLC R_f=1.0 (hexane); ¹H-NMR (400 MHz, CDCl₃) δ0.84-0.94 (m, 24H), 1.02-1.20 (m, 12H), 1.26-1.39 (m, 24H), 1.46-1.61 (m, 16-H), 2.51 (t, 4H, 8.0 Hz), 7.13 (s, 2H); MS (EI) m/z=912 (M⁺).

[Chemical Formula 92]

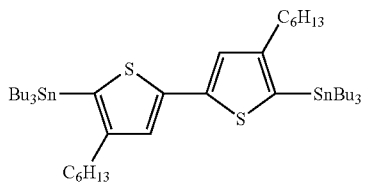

(37)

Synthesis of Compound R

After placing compound Q (50 mg, 0.055 mmol), compound F synthesized in Example 2 (32 mg, 0.12 mmol) and tetrakis(triphenylphosphine)palladium(0) (6 mg, 0.005 mmol) in a stoppered test tube, toluene (1 mL) was added to dissolve them. After stirring the mixture at 120° C. for 12 hours, it was allowed to cool at room temperature. The solvent was distilled off under reduced pressure, and the crude product was passed through silica gel column chromatography (CHCl₃) and then purified by GPC(CHCl₃) to obtain compound R represented by the following formula (38) (19 mg, 49% yield) as an orange solid. The oxidation potential of compound R was 0.48 V, and the reduction potential was −1.87 V. The peak wavelength in the absorption spectrum was 472 nm.

TLC R_f=0.43 (5:1=hexane/ethyl acetate); ¹H-NMR (400 MHz, CDCl₃) δ0.88-0.96 (m, 6H), 1.28-1.49 (m, 12H), 1.65-1.76 (m, 4H), 2.85 (t, 4H, J=7.9 Hz), 7.19 (s, 2H), 7.51 (s, 2H); MS (EI) m/z=706 (M⁺).

[Chemical Formula 93]

(38)

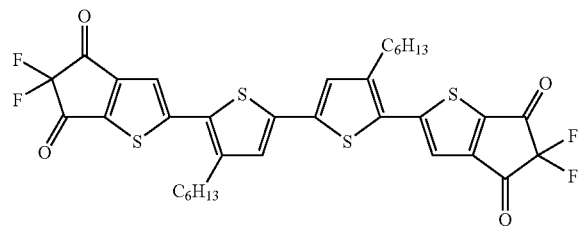

Example 11

Synthesis of Compound S

After placing 2,7-bis(1,3,2-dioxaborolan-2-yl)-9,9-di(n-octyl)fluorene, compound F, tetrakis(triphenylphosphine)palladium(0), potassium carbonate and a tetrahydrofuran (THF)/water mixed solvent in a heat-dried stoppered test tube, it is exchanged with nitrogen and reaction is conducted at 100° C. After 12 hours, the solvent is distilled off under reduced pressure, and the obtained crude product may be passed through silica gel column chromatography and then purified by GPC (CHCl₃) to obtain the target compound S represented by the following formula (39).

[Chemical Formula 94]

(39)

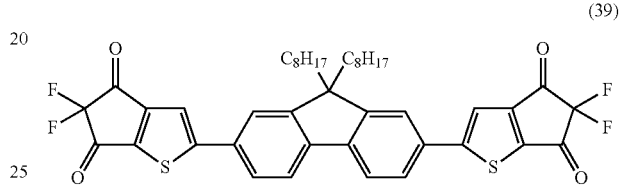

Example 12

Synthesis of Compound T

After placing 2,7-dibromo-9,9-di(n-octyl)fluorene, compound N and tetrakis(triphenylphosphine)palladium(0) in a stoppered test tube, toluene is added to dissolve them. After stirring the mixture at 120° C. for 12 hours, it is allowed to cool at room temperature. The solvent is distilled off under reduced pressure, and the obtained crude product is passed through silica gel column chromatography and then purified by GPC(CHCl₃). The obtained compound is placed in a volumetric flask and dissolved in THF, and then concentrated sulfuric acid is added and the mixture is stirred at room temperature for 12 hours. The reaction mixture is then poured into ice and extracted with ethyl acetate, and the organic layer is subsequently rinsed with aqueous saturated sodium hydrogencarbonate and water and dried over magnesium sulfate. The solvent may then be distilled off under reduced pressure and the obtained solid purified by GPC(CHCl₃) to obtain compound T represented by the following formula (40).

[Chemical Formula 95]

(40)

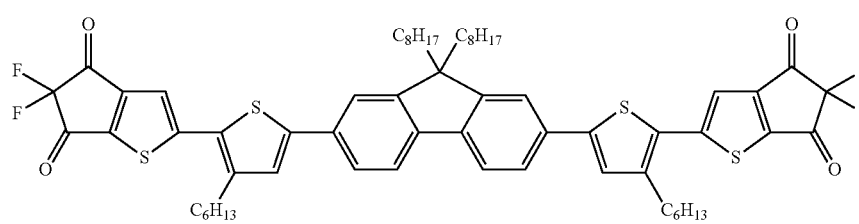

Example 13

Synthesis of Compound Ua

After placing 2,5-dibromothiophene (48 mg, 0.199 mmol), 5-tributyl-3-hexylthiophene (200 mg, 0.437 mmol) and tetrakis(triphenylphosphine)palladium(0) (11 mg, 0.0199 mmol) in a heat-dried stoppered test tube, toluene (2 mL) was added to dissolve them. After stirring the mixture at 120° C. for 12 hours, it was allowed to cool at room temperature. The solvent was then distilled off under reduced pressure, and the obtained crude product was purified by silica gel column chromatography (hexane) to obtain compound Ua represented by the following formula (41a) (48 mg, 58% yield) as a yellow liquid.

TLC $R_f$=0.75 (hexane); $^1$HNMR (400 MHz, CDCl$_3$) δ0.89 (m, 6H), 1.22-1.44 (m, 12H), 1.50-1.72 (m, 4H), 2.58 (t, 4H, J=7.8 Hz), 6.80 (s, 2H), 7.00 (s, 2H), 7.03 (s, 2H); MS (EI) m/z=416 (M$^+$).

[Chemical Formula 96]

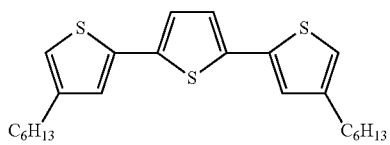

(41a)

Synthesis of Compound Ub

After placing compound Ua (100 mg, 0.240 mmol) and tetramethylethylenediamine (58 mg, 0.504 mmol) in a heat-dried 30 mL two-neck flask, diethyl ether (3 mL) was added to dissolve them. Next, n-butyllithium (1.58 M, 0.319 mL, 0.504 mmol) was slowly added at 0° C. After stirring for 2 hours, tributyltin chloride (0.221 ml, 0.814 mmol) was slowly added at −78° C. and the temperature was gradually raised to room temperature. Water was added to suspend the reaction, the aqueous phase was extracted using diethyl ether, and the organic phase was rinsed with aqueous saturated copper sulfate and then dried over magnesium sulfate. The solvent was then distilled off under reduced pressure, and the obtained crude product was purified by alumina column chromatography (hexane) to obtain compound Ub represented by the following formula (41b) (165 mg, 69% yield) as a yellow liquid.

TLC $R_f$=1.0 (hexane); $^1$HNMR (400 MHz, CDCl$_3$) δ0.84-0.96 (m, 24H), 1.05-1.20 (m, 12H), 1.25-1.45 (m, 24H), 1.50-1.70 (m, 16H), 2.51 (t, 4H, J=8.0 Hz), 7.02 (s, 2H), 7.14 (s, 2H).

[Chemical Formula 97]

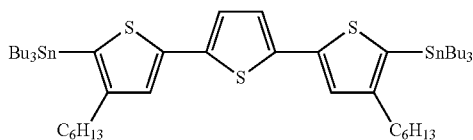

(41b)

Synthesis of Compound Uc

After placing compound Ub (50 mg, 0.050 mmol), compound F synthesized in Example 2 (29 mg, 0.11 mmol) and tetrakis(triphenylphosphine)palladium(0) (6 mg, 0.0050 mmol) in a test tube, toluene (1 mL) was added to dissolve them. After stirring the mixture at 120° C. for 12 hours, it was allowed to cool at room temperature. The solvent was then distilled off under reduced pressure, and the obtained crude product was passed through silica gel column chromatography (CHCl$_3$) and then purified by GPC(CHCl$_3$) to obtain compound Uc represented by the following formula (41c) (16 mg, 49% yield) as a red solid.

TLC $R_f$=0.48 (3:1=hexane/ethyl acetate); $^1$HNMR (400 MHz, CDCl$_3$) δ0.92 (t, 6H, J=7.1 Hz), 1.29-1.50 (m, 12H), 1.69-1.75 (m, 4H), 2.84 (t, 4H, J=7.8 Hz), 7.14 (s, 2H), 7.23 (s, 2H), 7.48 (s, 2H); MS (EI) m/z=788 (M).

[Chemical Formula 98]

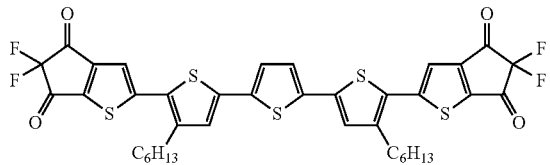

(41c)

Example 14

Synthesis of Compound V

After placing 1,3-dibromo-5,5-difluoro-4H-cyclopenta[c]thiophene-4,6(5H)-dione (400 mg, 1.16 mmol), 2-bromo-3-hexylthiophene (1.33 g, 2.90 mmol) and tetrakis(triphenylphosphine)palladium(0) (134 mg, 0.116 mmol) in a test tube, toluene (12 mL) was added to dissolve them. After stirring the mixture at 120° C. for 12 hours, it was allowed to cool at room temperature. The solvent was distilled off under reduced pressure, and the obtained crude product was passed through silica gel column chromatography (CHCl$_3$) and then purified by GPC(CHCl$_3$) to obtain compound V represented by the following formula (42) (247 mg, 41% yield) as a red solid.

TLC $R_f$=0.39 (3:1=hexane/ethyl acetate); $^1$HNMR (400 MHz, CDCl$_3$) δ0.84-0.93 (m, 6H), 1.23-1.41 (m, 12H), 1.61-1.72 (m, 4H), 2.75 (t, 4H, J=7.9 Hz), 7.09 (d, 2H, J=5.1 Hz), 7.52 (d, 2H, J=5.1 Hz); MS (EI) m/z=520 (M$^+$).

[Chemical Formula 99]

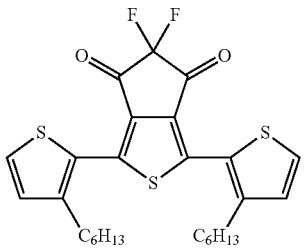

(42)

Synthesis of Compound W

Compound V (103 mg, 0.198 mmol) was placed in a heat-dried 20 mL volumetric flask while cooling on ice, and DMF (2 mL) was added to dissolve it. Next, N-bromosuccinimide (NBS) (74 mg, 0.416 mmol) was added and the mixture was slowly heated to 80° C. After stirring for 12 hours, water was added to suspend the reaction. The aqueous phase was extracted with ethyl acetate and rinsed with water, and then the organic phase was dried over magnesium sulfate. The solvent was distilled off under reduced pressure, and then the obtained crude product was purified by silica gel column chromatography (ethyl acetate) to obtain compound W represented by the following formula (43) (125 mg, 91% yield) as a red solid.

TLC $R_f$=0.42 (3:1=hexane/ethyl acetate); $^1$HNMR (400 MHz, CDCl$_3$) δ0.88 (t, 6H, J=7.1 Hz), 1.20-1.42 (m, 12H), 1.60-1.71 (m, 4H), 2.70 (t, 4H, J=7.9 Hz), 7.22 (s, 2H); MS (EI) m/z=678 (M$^+$).

[Chemical Formula 100]

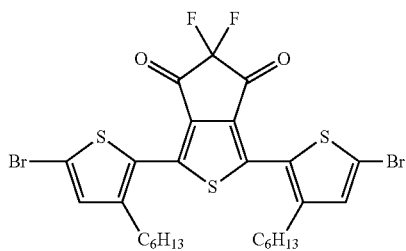

(43)

Synthesis of Compound X

After placing compound W (125 mg, 0.184 mmol), compound E (240 mg, 0.424 mmol) and tetrakis(triphenylphosphine)palladium(0) (21 mg, 0.018 mmol) in a test tube, toluene (2 mL) was added to dissolve them. After stirring the mixture at 120° C. for 12 hours, it was allowed to cool at room temperature. The solvent was then distilled off under reduced pressure, and the obtained crude product was passed through alumina column chromatography (CHCl$_3$) and then purified by GPC(CHCl$_3$). It was then placed in a volumetric flask (50 mL) and dissolved in THF (1 mL). Concentrated sulfuric acid (20 mL) was added and the mixture was stirred at room temperature for 12 hours. The reaction mixture was poured into ice and extraction was performed with ethyl acetate. The organic phase was rinsed with aqueous saturated sodium hydrogencarbonate and then with water, and dried over magnesium sulfate. The solvent was distilled off under reduced pressure, and the obtained solid was purified by GPC(CHCl$_3$) to obtain compound X represented by the following formula (44) (23 mg, 14% yield in 2 steps) as a red solid.

TLC $R_f$=0.51 (2:1=hexane/ethyl acetate); $^1$HNMR (400 MHz, CDCl$_3$) δ0.86 (t, 6H, J=7.0 Hz), 1.17-1.41 (m, 12H), 1.69-1.78 (m, 4H), 2.81 (t, 4H, J=8.0 Hz), 7.47 (s, 2H), 7.63 (s, 2H); MS (EI) m/z=892 (M$^+$).

[Chemical Formula 101]

(44)

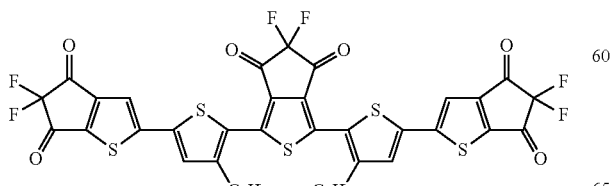

Thus, the organic thin-film devices comprising organic thin films containing π-conjugated compounds of the present invention fabricated in Examples 5, 6, 7 and 8 had more satisfactory electron mobility than the organic thin-film device fabricated in Comparative Example 3. This confirmed that the π-conjugated compounds of the present invention can be utilized as n-type organic semiconductors with excellent electron transport properties.

Examples of the second invention group will now be described.

(Measuring Conditions)

The nuclear magnetic resonance (NMR) spectra were measured using a JMN-270 (270 MHz for $^1$H measurement) or a JMNLA-600 (600 MHz for $^{19}$F measurement), both trade names of JEOL Corp. The chemical shifts are represented as parts per million (ppm). Tetramethylsilane (TMS) was used as the internal reference (0 ppm). The coupling constant (J) is represented in Hz, and the symbols s, d, t, q, m and br respectively represent singlet, doublet, triplet, quartet, multiplet and broad. The mass spectrometry (MS) was performed using a GCMS-QP5050A, trade name of Shimadzu Corp., by electron ionization (EI) or direct inlet (DI). The silica gel used for separation by column chromatography was Silicagel 60N (40-50 μm), trade name of Kanto Kagaku Co., Ltd. All of the chemical substances were reagent grade and purchased from Wako Pure Chemical Industries, Ltd., Tokyo Kasei Kogyo Co., Ltd., Kanto Kagaku Co., Ltd., Nacalai Tesque, Inc., Sigma Aldrich Japan, KK. or Daikin Chemicals Co., Ltd.

Example α-1

Synthesis of Compound α-A

Thiazole (8.50 g, 100 mmol) and tetrahydrofuran (150 mL) were placed in a heat-dried volumetric flask. The mixture was then exchanged with nitrogen and cooled to −78° C., after which n-butyllithium (2.66 M, 41.0 mL, 110 mmol) was added for reaction. After 1 hour, triisopropylsilyl chloride (23.5 mL, 110 mmol) was added at −78° C. and the temperature was raised to room temperature. After 1 hour, water was added and extraction was performed with ethyl acetate. The organic phase was dried over magnesium sulfate and concentrated under reduced pressure. It was then purified by vacuum distillation to obtain compound α-A represented by the following formula (α-A) as the target product (17.6 g, 73% yield) as a pale yellow liquid.

TLC $R_f$=0.5 (hexane): $^1$H-NMR (400 MHz, CDCl$_3$): δ 8.17 (d, 1H, J 3.0 Hz), 7.55 (d, 1H, J=3.0 Hz), 1.45 (m, 3H), 1.14 (d, 21H, J=3.0 Hz):GC-MS (EI):m/z=241 (M$^+$).

[Chemical Formula 102]

(α-A)

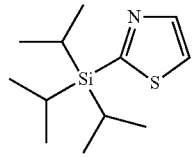

Synthesis of Compound α-B

Compound α-A (9.57 g, 39.6 mmol) and tetrahydrofuran (135 mL) were placed in a heat-dried volumetric flask. The mixture was then exchanged with nitrogen and cooled to −78° C., after which n-butyllithium (2.66 M, 15 mL, 39.9 mmol) was added for reaction. After 1 hour, tributyltin chloride (13.0 g, 39.9 mmol) was added at −78° C. and the temperature was raised to room temperature. After 1 hour, water was added and extraction was performed with ethyl acetate. The organic phase was dried over magnesium sulfate and concentrated under reduced pressure. It was then purified with an alumina column (hexane) to obtain compound α-B represented by the following formula (α-B) as the target product, (20.9 g, 99% yield) as a yellow liquid.

TLC $R_f$=0.3 (hexane): $^1$H-NMR (400 MHz, CDCl$_3$): δ 8.11 (s, 1H), 1.57 (m), 1.47 (m), 1.33 (m), 1.14 (m), 0.88 (m):GC-MS (DI):m/z=530 (M$^+$).

[Chemical Formula 103]

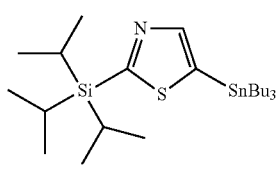

(α-B)

Synthesis of Compound α-C

Compound α-A (8.00 g, 33.1 mmol) and tetrahydrofuran (60 mL) were placed in a heat-dried volumetric flask. The mixture was then exchanged with nitrogen and cooled to −78° C., after which n-butyllithium (2.66 M, 19 mL, 49.4 mmol) was added for reaction. After 1 hour, bromine (2.6 mL, 49.4 mmol) was added at −78° C. and the temperature was raised to room temperature. After 1 hour, water was added and extraction was performed with ethyl acetate. The organic phase was dried over magnesium sulfate and concentrated under reduced pressure. It was then purified with a silica gel column (hexane) to obtain compound α-C represented by the following formula (α-C) as the target product, (9.11 g, 86% yield) as an orange liquid.

TLC $R_f$=0.1 (hexane): $^1$H-NMR (400 MHz, CDCl$_3$): δ 7.97 (s, 1H), 1.42 (m, 3H), 1.13 (d, 21H, J=7.5 Hz):GC-MS (EI): m/z=320 (M$^+$).

[Chemical Formula 104]

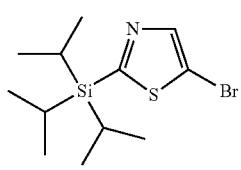

(α-C)

Synthesis of Compound α-D

After placing compound α-B (5.39 g, 10.2 mmol), compound α-C (3.10 mg, 9.68 mmol), tetrakis(triphenylphosphine)palladium(0) (500 mg, 0.433 mmol) and toluene (30 mL) in a heat-dried stoppered test tube, it was exchanged with nitrogen and refluxed for 4 days. The mixture was filtered with Celite and then concentrated under reduced pressure. It was then purified with an alumina column (hexane/ethyl acetate=20:1) to obtain compound α-D represented by the following formula (α-D) as the target product (3.77 g, 81% yield) as a white solid.

TLC $R_f$=0.5 (hexane/ethyl acetate=20:1): $^1$H-NMR (400 MHz, CDCl$_3$): δ 8.19 (s, 2H), 1.46 (m, 6H), 1.16 (d, 42H, J=7.5 Hz):GC-MS (DI):m/z=480 (M$^+$).

[Chemical Formula 105]

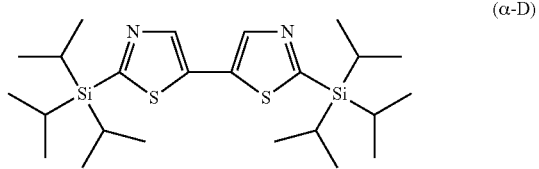

(α-D)

Synthesis of Compound α-E

After exchanging a heat-dried volumetric flask with nitrogen and cooling it to −40° C., tetrahydrofuran (1 mL), diisopropylamine (0.8 mL) and n-butyllithium (1.6 M, 3.2 mL, 5.3 mmol) were placed therein. Next, compound α-D (385 mg, 0.801 mmol) was added and reaction was conducted. After 1 hour, ethyl-1-piperidine carboxylate (200 mg, 1.27 mmol) was added at −40° C. and reaction was conducted. After 1 hour, water was added and extraction was performed with ethyl acetate. The organic phase was dried over magnesium sulfate and concentrated under reduced pressure. It was then purified with a silica gel column (hexane/ethyl acetate=20:1) to obtain compound α-E represented by the following formula (α-E) as the target product (401 mg, 99% yield) as a red solid.

TLC $R_f$=0.6 (hexane/ethyl acetate=20:1): $^1$H-NMR (400 MHz, CDCl$_3$): δ 1.45 (m, 6H), 1.14 (d, 42H, J=7.5 Hz):GC-MS (DI):m/z=506 (M$^+$).

[Chemical Formula 106]

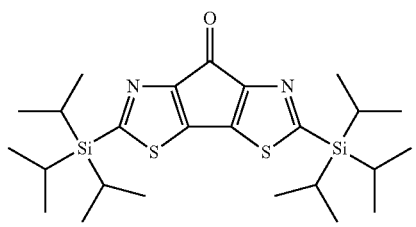

(α-E)

Synthesis of Compound α-F

Compound α-E (100 mg, 0.197 mmol) and tetrahydrofuran (2 mL) were placed in a heat-dried volumetric flask. It was exchanged with nitrogen and then cooled to 0° C., and then tetrabutylammonium fluoride (1.0 M, 0.45 mL, 0.45 mmol) was added and reaction was conducted. After 4 hours, the temperature was raised to room temperature, water was added, and extraction was performed with ethyl acetate and chloroform. The organic phase was rinsed with water, dried over magnesium sulfate and concentrated under reduced pressure. It was then purified by silica gel column chromatography (ethyl acetate) to obtain compound α-F represented by the following formula (α-F) (30 mg, 78% yield) as a violet compound.

TLC $R_f$=0.1 (ethyl acetate): GC-MS (DI):m/z=194 (M$^+$).

[Chemical Formula 107]

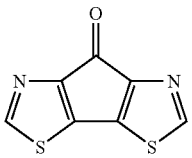

(α-F)

Example α-2

Synthesis of Compound α-G

In a heat-dried volumetric flask there were placed compound α-E (3.00 g, 5.91 mmol), 2-ethanol chloride (1.90 g, 23.6 mmol), DMF (160 mL) and tetrahydrofuran (80 mL). The mixture was then exchanged with nitrogen and cooled to −78° C., after which t-butoxypotassium (1.33 g, 11.9 mmol) was added for reaction. After 7 hours, an aqueous solution of 10 wt % ammonium chloride was added and extraction was performed with ethyl acetate. The organic phase was dried over magnesium sulfate and concentrated under reduced pressure. It was then purified by silica gel column chromatography (hexane/ethyl acetate=10:1) to obtain a light orange solid. The obtained light orange solid and tetrahydrofuran (50 mL) were placed in a heat-dried volumetric flask. It was exchanged with nitrogen and then cooled to 0° C., and then tetrabutylammonium fluoride (1.0 M, 12.5 mL, 12.5 mmol) was added and reaction was conducted. After 1 hour, the temperature was raised to room temperature, water was added and extraction was performed with ethyl acetate, and then the organic phase was washed with water, dried over magnesium sulfate and concentrated under reduced pressure. It was then purified by silica gel column chromatography (hexane/ethyl acetate=1:1) to obtain compound α-G represented by the following formula (α-G) (677 mg, 48% yield) as a light brown solid.

TLC $R_f$=0.6 (hexane/ethyl acetate=2:1): $^1$H-NMR (400 MHz, CDCl$_3$): δ 8.65 (s, 2H), 4.52 (s, 4H):GC-MS (DI):m/z=238 (M$^+$).

[Chemical Formula 108]

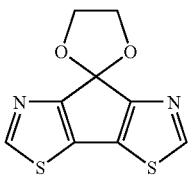

(α-G)

Synthesis of Compound α-H

Compound α-G (49 mg, 0.21 mmol) and tetrahydrofuran (2 mL) were placed in a heat-dried volumetric flask. The mixture was then exchanged with nitrogen and cooled to −78° C., after which n-butyllithium (1.6 M, 0.30 mL, 0.48 mmol) was added for reaction. After 30 minutes, tributyltin chloride (160 mg, 0.49 mmol) was added at −78° C. and the temperature was raised to room temperature. After 1 hour, water was added and extraction was performed with ethyl acetate. The organic phase was dried over magnesium sulfate and concentrated under reduced pressure. It was then purified with an alumina column (hexane) to obtain compound α-H represented by the following formula (α-H) as the target product, (126 mg, 75% yield) as a yellow liquid.

TLC $R_f$=0.9 (hexane/ethyl acetate=20:1): $^1$H-NMR (400 MHz, CDCl$_3$): δ 4.55 (s, 4H), 1.58 (m), 1.35 (m), 1.21 (m), 0.90 (m):GC-MS (DI):m/z=816 (M$^+$).

[Chemical Formula 109]

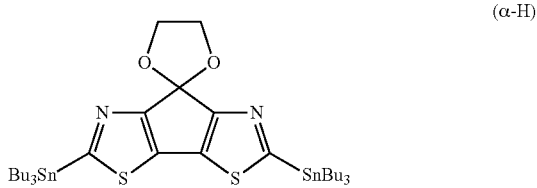

(α-H)

Synthesis of Compound α-I

After placing compound α-H (240 mg, 0.294 mmol), 4'-bromo-2,2,2-trifluoroacetophenone (223 mg, 0.881 mmol), tetrakis(triphenylphosphine)palladium(0) (34 mg, 0.029 mmol) and toluene (6 mL) in a heat-dried stoppered test tube, it was exchanged with nitrogen and refluxed for 13 hours. After filtration with Celite, it was concentrated under reduced pressure and the obtained red solid was rinsed with methanol and diethyl ether. After placing the obtained red solid, acetic acid (50 mL) and concentrated hydrochloric acid (3 mL) in a volumetric flask, the mixture was heated to 100° C. After 2 hours, the temperature was lowered to room temperature, water was added, and the produced solid was rinsed with water, methanol and diethyl ether. Sublimation purification was carried out under reduced pressure to obtain compound α-I represented by the following formula (α-I) as the target product (33 mg, 21% yield), as a green solid.

$^1$H-NMR (400 MHz, CDCl$_3$): δ 8.08 (d, 4H, J=8.8 Hz), 8.05 (d, 4H, J 8.8 Hz):GC-MS (DI):m/z=538 (M$^+$).

[Chemical Formula 110]

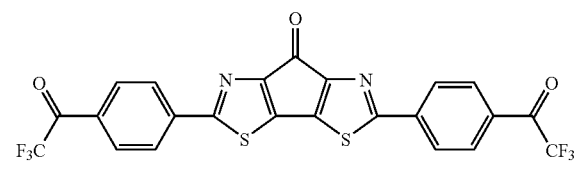

(α-I)

Figure 13:
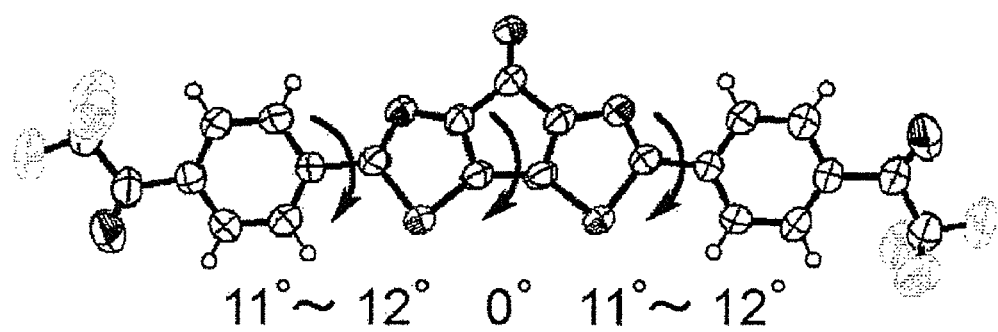
FIG. 13 is a drawing showing the torsional angles formed between adjacent bonded molecular rings in compound α-I.
Figure 14:
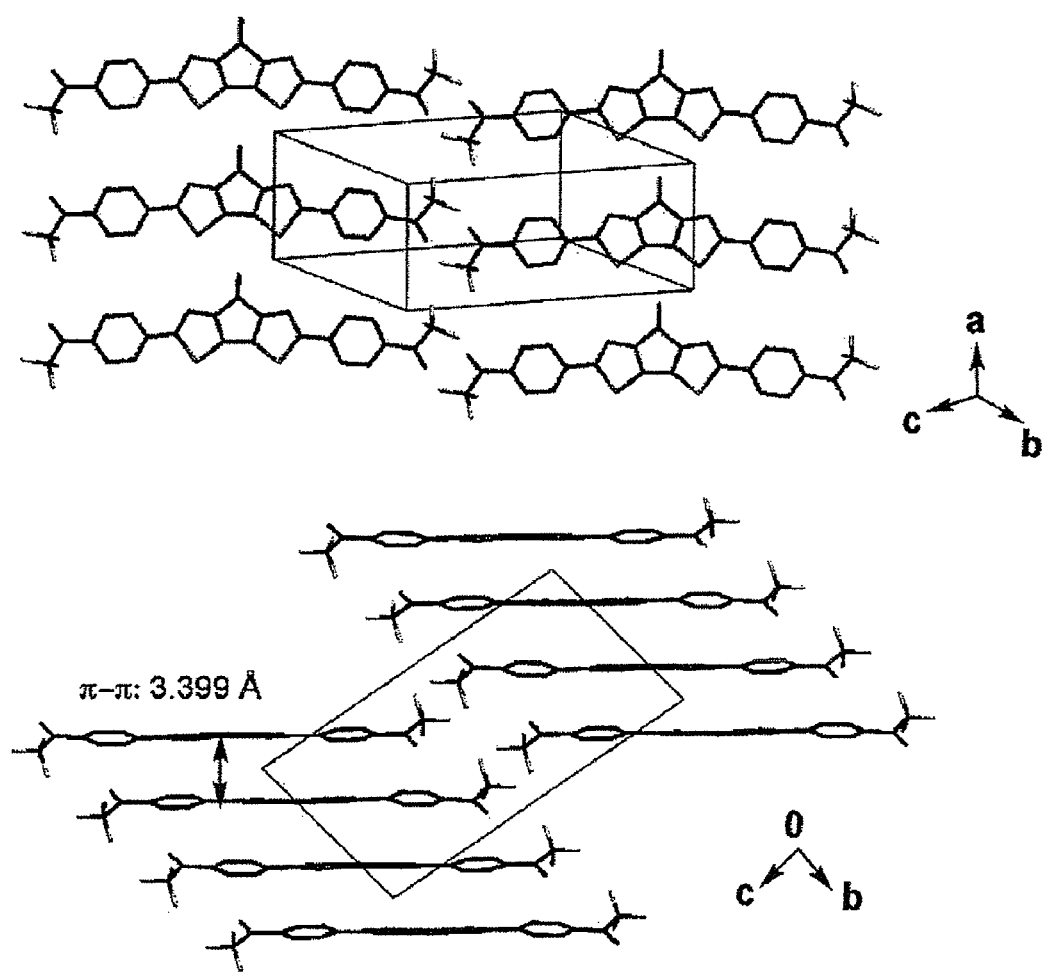
FIG. 14 is a drawing showing the crystal structure of compound α-I.

Compound α-I was subjected to X-ray structural analysis to measure the torsional angle between adjacently bonded molecular rings, by which highly planarity of 11-12 degrees was confirmed (FIG. 13). In addition, the molecular crystals exhibited a π-π stack structure with the π planes between adjacent molecules opposite each other, and a plane spacing of 0.34 nm was confirmed (FIG. 14).

Example α-3

Synthesis of Compound α-J

After placing compound α-H, 2-bromo-5,5-difluoro-4H-cyclopenta[b]thiophene-4,6(5H)-dione, tetrakis(triphenylphosphine)palladium(0) and toluene in a heat-dried stoppered test tube, the mixture was exchanged with nitrogen and refluxed. The product was reacted with acetic acid and concentrated hydrochloric acid at 100° C. to obtain compound α-J represented by the following formula (α-J) as the target substance.

[Chemical Formula 111]

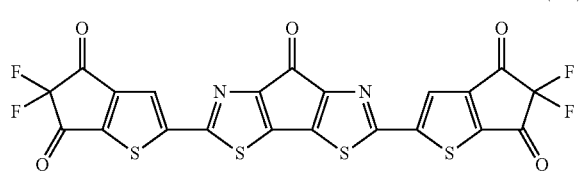

(α-J)

Example α-4

Synthesis of Compound α-K

After placing compound α-H, compound α-L represented by the following formula (α-L), tetrakis(triphenylphosphine)palladium(0) and toluene in a heat-dried stoppered test tube, the mixture was exchanged with nitrogen and refluxed. The product was reacted with acetic acid and concentrated hydrochloric acid at 100° C. to obtain compound α-K represented by the following formula (α-K) as the target substance.

[Chemical Formula 112]

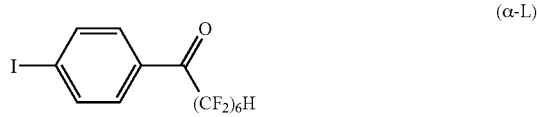

(α-L)

[Chemical Formula 113]

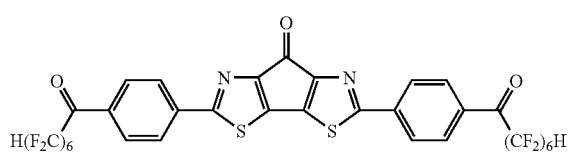

(α-K)

Example α-5

Fabrication of Organic Thin-Film Device 1 and Evaluation of Transistor Property

A substrate was prepared by forming a silicon oxide film as the insulating layer, by thermal oxidation to a thickness of 300 nm on the surface of a highly doped p-type silicon substrate as the gate electrode. The lift-off method was used to form on this substrate a comb-shaped source electrode and drain electrode with a channel width of 38 mm and a channel length of 5 μm. The electrode-formed substrate was subjected to ultrasonic cleaning for 10 minutes in acetone and for 10 minutes in isopropyl alcohol, after which it was irradiated with ozone UV for 30 minutes to clean the surface. An organic thin film of compound α-I was accumulated on the cleaned substrate to a film thickness of 10 mm using compound α-I synthesized in Example α-2, by vacuum vapor deposition at a substrate temperature of 110° C. and a deposition rate of 0.2 nm/min, to fabricate an organic thin-film device 1. The organic transistor property was measured by varying the gate voltage Vg from 0 to 120 V and the source-drain voltage Vsd from 0 to 100 V for the organic thin-film device 1 in a vacuum, and a satisfactory n-type semiconductor Id-Vg characteristic was obtained. The mobility during this time was $5.6 \times 10^{-2}$ cm$^2$/Vs, the threshold voltage was 20 V and the on/off ratio was satisfactory at $10^6$. This confirmed that the organic thin-film device 1 using compound α-I effectively functions as an n-type organic transistor, and that compound α-I can be utilized as an organic n-type semiconductor with an excellent electron transport property.

The organic transistor device 1 also exhibited a satisfactory transistor property when operated in air (approximately 20° C.), during which the mobility was $1.6 \times 10^{-3}$ cm$^2$/Vs.

Example α-6

Fabrication of Organic Thin-Film Device 2 and Evaluation of Transistor Property

A substrate was prepared by forming a silicon oxide film as the insulating layer, by thermal oxidation to a thickness of 300 nm on the surface of a highly doped p-type silicon substrate as the gate electrode. The substrate was subjected to ultrasonic cleaning for 10 minutes in acetone and for 10 minutes in isopropyl alcohol, after which it was irradiated with ozone UV for 30 minutes to clean the surface. An organic thin film of compound α-I was accumulated on the cleaned substrate to a film thickness of 10 nm by vacuum vapor deposition under conditions with a substrate temperature of 110° C. and a deposition rate of 0.2 angstrom/sec. Au was formed to a thickness of 20 nm on the organic thin film by vapor deposition through a shadow mask, to form a source electrode and drain electrode with a channel width of 5.0 mm and a channel length of 50 μm, thus fabricating an organic thin-film device 2. The transistor property was measured by varying the gate voltage Vg and the source-drain voltage Vsd for the obtained organic thin-film device 2 in a vacuum, and a satisfactory Id-Vg characteristic was obtained. The mobility during this time was $1.6 \times 10^{-2}$ cm$^2$/Vs, the threshold voltage was 41 V and the on/off ratio was satisfactory at $10^4$. This confirmed that the organic thin-film device 2 using compound α-I effectively functions as an n-type organic transistor and, as in Example α-5, that compound α-I can be utilized as an organic n-type semiconductor with an excellent electron transport property.

Also, when the organic transistor device 2 was annealed for 30 minutes at 130° C. in a vacuum, the transistor property was improved and the mobility was $2.6 \times 10^{-2}$ cm$^2$/Vs.

When the organic transistor device 2 was operated in air (approximately 28° C.), it also exhibited a satisfactory transistor property during which the mobility was $2.1 \times 10^{-2}$ cm$^2$/Vs. Even after standing in air (approximately 28° C.) for 24 hours, the organic transistor device 2 had a mobility of $1.3 \times 10^{-2}$ cm$^2$/Vs, thus confirming its stability in air.

Comparative Example α-1

Synthesis of Compound α-M

After placing 5,5'-dibromo-bithiophene (242 mg, 0.75 mmol), 4-acetylphenylboronic acid (366 mg, 2.23 mmol), tetrakis(triphenylphosphine)palladium(0) (40 mg, 0.05 mmol), NaHCO$_3$ (438 mg, 521 mmol) and a DME/water mixed solvent (7 mL) in a heat-dried stoppered test tube, it was exchanged with nitrogen and reaction was conducted at 100° C. After 14 hours, the mixture was concentrated under reduced pressure to obtain a solid. The obtained solid was rinsed with methanol and ether and then subjected to sublimation purification in a vacuum, to obtain compound α-M represented by the following formula (α-M) as the target product (205 mg, 83% yield), as a light yellow solid. The reduction potential of compound α-M was unmeasurable because the compound was insoluble.

TLC $R_f$=0.0 (chloroform): $^1$H-NMR (400 MHz, CDCl$_3$): δ 7.96 (m, 2H), 7.68 (m, 2H), 7.36 (m, 2H), 7.23 (m, 2H), 2.60 (s, 3H):GC-MS (DI):m/z 402 (M$^+$).

[Chemical Formula 114]

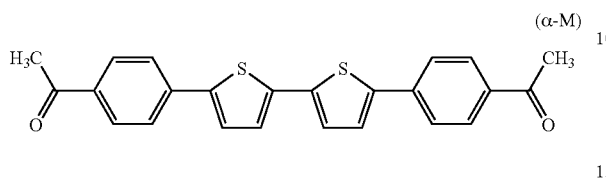

(α-M)

Comparative Example α-2

Fabrication of Organic Thin-Film Device 3 and Evaluation of Transistor Property

Organic thin-film device 3 was fabricated in the same manner as Example α-5, except that the organic thin film was formed of compound α-M synthesized in Comparative Example α-1 instead of compound α-I synthesized in Example α-2. The organic transistor property was measured by varying the gate voltage Vg from 0 to 100 V and the source-drain voltage Vsd from 0 to 100 V for the organic thin-film device 3 in a vacuum, to obtain the n-type semiconductor Id-Vg characteristic. The mobility during this time was $1.8 \times 10^{-5}$ cm$^2$/Vs, and the on/off ratio was low at $10^2$.

INDUSTRIAL APPLICABILITY

As explained above, according to the first invention group it is possible to provide novel conjugated compounds that can be used as organic n-type semiconductors with excellent electron transport properties. It is also possible to provide organic thin films containing the novel conjugated compounds, and organic thin-film devices comprising the organic thin films.

According to the second invention group, it is possible to provide novel nitrogen-containing fused-ring compounds and novel nitrogen-containing fused-ring polymers that can be used as organic n-type semiconductors with excellent electron transport properties. It is also possible to provide organic thin films containing the nitrogen-containing fused-ring compounds or nitrogen-containing fused-ring polymers, and organic thin-film devices comprising the organic thin films.

The invention claimed is:
1. A nitrogen-containing fused-ring compound represented by the following formula (α-I):

[Chemical Formula 8]

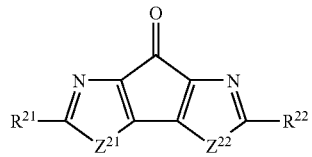

(α-I)

in formula (α-I), R$^{21}$ and R$^{22}$ each independently represent a hydrogen atom, a halogen atom or an optionally substituted monovalent group, and Z$^{21}$ and Z$^{22}$ each independently represent any one of the groups represented by the following formulas (α-i)-(α-ix);

[Chemical Formula 9]

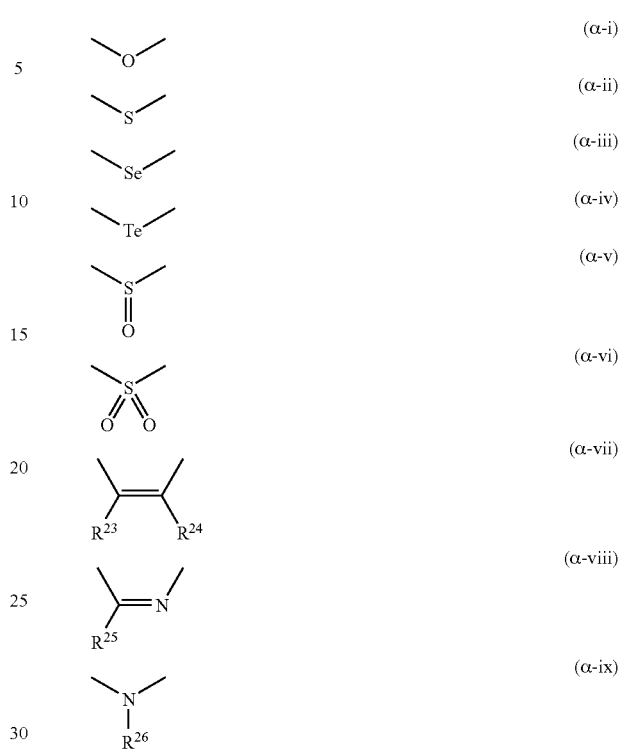

wherein R$^{23}$, R$^{24}$, R$^{25}$ and R$^{26}$ each independently represent a hydrogen atom, a halogen atom or a monovalent group, and R$^{23}$ and R$^{24}$ may bond together to form a ring, the left side and the right side of the group represented by formula (α-viii) may be interchanged.

2. The nitrogen-containing fused-ring compound according to claim 1, wherein Z$^{21}$ and Z$^{22}$ are groups represented by formula (α-ii).

3. The nitrogen-containing fused-ring compound according to claim 1 represented by the following formula (α-I-I):

[Chemical Formula 10]

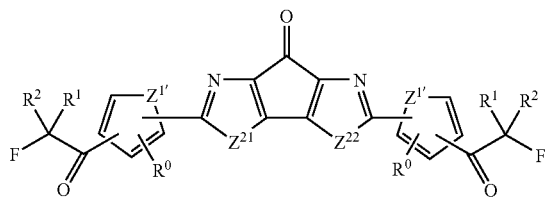

(α-I-I)

in formula (α-I-I), Z$^{21}$, Z$^{22}$ and L$^{1'}$ each independently represent any one of the groups represented by formulas (α-i)-(α-ix), R$^1$ and R$^2$ each independently represent a hydrogen atom, a halogen atom or a monovalent group, and each R$^0$ represents a hydrogen atom, a C1 to 20 alkyl group or a C1 to 20 alkoxy group; a plurality of the groups in R$^0$ may be the same or different.

4. The nitrogen-containing fused-ring compound according to claim 1, wherein at least one of R$^{21}$ and R$^{22}$ is a group represented by the following formula (IV):

[Chemical Formula 11]

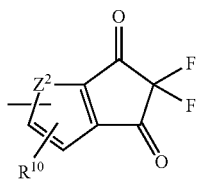
(IV)

wherein $R^{10}$ represents a hydrogen atom, a fluorine atom, a C1 to C20 alkyl group, a C1 to C20 fluoroalkyl group, a C1 to C20 alkoxy group or a C1 to C20 fluoroalkoxy group, $Z^2$ represents any one of the groups represented by the following formulas (xi)-(xix), $R^{13}$, $R^{14}$, $R^{15}$ and $R^{16}$ each independently represent a hydrogen atom, a halogen atom or a monovalent group, and $R^{13}$ and $R^{14}$ may bond together to form a ring.

[Chemical Formula 12]

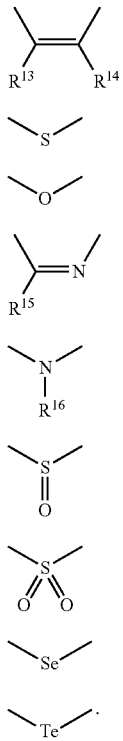

(xi)
(xii)
(xiii)
(xiv)
(xv)
(xvi)
(xvii)
(xviii)
(xix)

5. A nitrogen-containing fused-ring polymer having a repeating unit represented by the following formula (α-II):

[Chemical Formula 13]

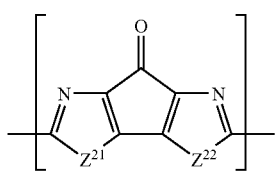
(α-II)

in formula (α-II), $Z^{21}$ and $Z^{22}$ each independently represent any one of the groups represented by the following formulas (α-i)-(α-ix);

[Chemical Formula 14]

 (α-i)

 (α-ii)

 (α-iii)

 (α-iv)

 (α-v)

 (α-vi)

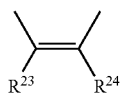 (α-vii)

 (α-viii)

(α-ix)

wherein $R^{23}$, $R^{24}$, $R^{25}$ and $R^{26}$ each independently represents a hydrogen atom, a halogen atom or a monovalent group, and $R^{23}$ and $R^{24}$ may bond together to form a ring; the left side and the right side of the group represented by formula (α-viii) may be interchanged.

6. The nitrogen-containing fused-ring polymer according to claim 5, wherein $Z^{21}$ and $Z^{22}$ are groups represented by formula (α-ii).

7. The nitrogen-containing fused-ring polymer according to claim 5 having at least one repeating unit represented by the formula (α-II) and at least one repeating unit represented by the following formula (α-III):

[Chemical Formula 15]

—(Ar²¹)— (α-III)

in formula (α-III), $Ar^{21}$ represents a divalent aromatic hydrocarbon or divalent heterocyclic group, which may have a substituent.

8. The nitrogen-containing fused-ring polymer according to claim 7, wherein $Ar^{21}$ is a group represented by the following formula (α-IV):

[Chemical Formula 16]

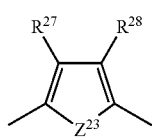
(α-IV)

in formula (α-IV), $R^{27}$ and $R^{28}$ each independently represent a hydrogen atom, a halogen atom or a monovalent group, and $Z^{23}$ represents any one of the groups represented by the following formulas (α-i)-(α-ix); $R^{27}$ and $R^{28}$ may bond together to form a ring;

[Chemical Formula 17]

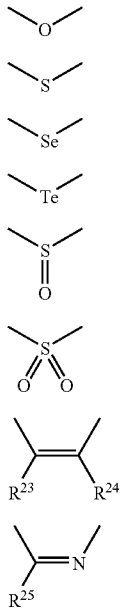

(α-i)
(α-ii)
(α-iii)
(α-iv)
(α-v)
(α-vi)
(α-vii)
(α-viii)

-continued

(α-ix)

wherein $R^{23}$, $R^{24}$, $R^{25}$ and $R^{26}$ each independently represent a hydrogen atom, a halogen atom or a monovalent group, and $R^{23}$ and $R^{24}$ may bond together to form a ring; the left side and the right side of the group represented by formula α-viii) may be interchanged.

9. The nitrogen-containing fused-ring polymer according to claim 8, wherein $Z^{23}$ is a group represented by formula (α-ii).

10. An organic thin film comprising the nitrogen-containing fused-ring compound according to claim 1.

11. An organic thin-film device comprising the organic thin film according to claim 10.

12. An organic thin-film transistor comprising the organic thin film according to claim 10.

13. An organic solar cell comprising the organic thin film according to claim 10.

14. An optical sensor comprising the organic thin film according to claim 10.

15. An organic thin film comprising the nitrogen-containing fused-ring polymer according to claim 5.

16. An organic thin-film device comprising the organic thin film according to claim 15.

17. An organic thin-film transistor comprising the organic thin film according to claim 15.

18. An organic solar cell comprising the organic thin film according to claim 15.

19. An optical sensor comprising the organic thin film according to claim 15.

* * * * *